US008673277B2

(12) United States Patent
Tamareselvy et al.

(10) Patent No.: US 8,673,277 B2
(45) Date of Patent: Mar. 18, 2014

(54) STRUCTURED ACRYLATE COPOLYMER THICKENERS

(75) Inventors: Krishnan Tamareselvy, Brecksville, OH (US); Deborah S. Filla, Twinsburg, OH (US); Steven J. Smith, Wakeman, OH (US); David L. Dashiell, Lakewood, OH (US); Gary Gray, Avon Lake, OH (US); Yi Yang, Bridgewater, NJ (US); John J. Mullay, Mentor, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 13/809,245

(22) PCT Filed: Jul. 7, 2011

(86) PCT No.: PCT/US2011/043151

§ 371 (c)(1), (2), (4) Date: Jan. 9, 2013

(87) PCT Pub. No.: WO2012/006402

PCT Pub. Date: Jan. 12, 2012

(65) Prior Publication Data

US 2013/0115185 A1 May 9, 2013

Related U.S. Application Data

(60) Provisional application No. 61/362,742, filed on Jul. 9, 2010.

(51) Int. Cl.
*C08L 33/14* (2006.01)

(52) U.S. Cl.
USPC .................... 424/70.16; 427/393.5; 428/515; 428/520; 510/441; 524/156; 524/516; 524/522

(58) Field of Classification Search
None
See application file for complete search history.

(56) References Cited

U.S. PATENT DOCUMENTS 5,840,789 A 11/1998 Verstrat et al.

FOREIGN PATENT DOCUMENTS

| | | | |
|---|---|---|---|
| EP | 0436960 | A1 | 7/1991 |
| EP | 0824914 | A1 | 2/1998 |
| EP | 0825200 | A1 | 2/1998 |
| WO | 98/06757 | A1 | 2/1998 |
| WO | 01/72909 | A2 | 10/2001 |

*Primary Examiner* — Robert A Wax
*Assistant Examiner* — Randeep Singh
(74) *Attorney, Agent, or Firm* — Thoburn T. Dunlap

(57) ABSTRACT

Disclosed are multi-staged acrylic based core-shell polymers comprising a linear core polymer and at least one subsequently polymerized shell polymers is crosslinked. The core-shell polymers surprisingly provide desirable rheological, clarity, and aesthetic properties in aqueous surfactant containing compositions, particularly at low pH.

42 Claims, 4 Drawing Sheets

STRUCTURED ACRYLATE COPOLYMER THICKENERS

CROSS REFERENCE TO RELATED APPLICATION

This application claims priority from PCT Application Serial No. PCT/US2011/043151 filed on Jul. 7, 2011, which claims the benefit of U.S. Provisional Application No. 61/362,742 filed on Jul. 9, 2010.

TECHNICAL FIELD

In one aspect, the present invention relates to acrylic based staged core-shell polymers comprising a linear core and at least one crosslinked outer shell. In another aspect, the invention relates to an acrylic based staged core-shell polymer thickener suitable for use in aqueous systems. A further aspect of the invention relates to the formation of stable, aqueous compositions containing a acrylic based staged core-shell polymer rheology modifier, a surfactant, and optionally various components that are substantially insoluble materials requiring suspension or stabilization. Additionally, a further aspect of the invention relates to the formation of clear, rheologically and phase stable surfactant compositions formulated at low pH ranges.

BACKGROUND OF THE INVENTION

Rheology modifiers, also referred to as thickeners or viscosifiers, are ubiquitous in surfactant containing personal care cleansing formulations. Rheological properties (e.g., viscosity and flow characteristics, foamability, spreadability, and the like), aesthetic properties (e.g., clarity, sensory effects, and the like), mildness (dermal and ocular irritation mitigation), and the ability to suspend and stabilize soluble and insoluble components within a surfactant based formulation are often modified by the addition of a thickener.

Often, thickeners are introduced into surfactant formulations in solid form and mixed under conditions effective to dissolve the thickener into the liquid surfactant composition in order to effect a viscosity enhancement. Frequently, the mixing must be conducted at elevated temperatures (hot processing) in order to promote the dissolution of the solid thickener and obtain the desired viscosity improvement. Additionally, solid thickeners (e.g., Carbomer powders) are known to resist “wet-out” upon contact with the surface of an aqueous based system. Consequently, Carbomers are supplied as finely divided powders and/or must be sifted to reduce particle size, which aids in dissolution by increasing the relative surface area of the particle. During processing, Carbomer powders can become electrostatically charged as they are transferred in and out of containers and tend to adhere to oppositely charged surfaces including airborne dust, necessitating specialized dust extraction equipment. This means that preparation of aqueous dispersions is messy and time-consuming unless special precautions and expensive equipment is employed. Formulators of compositions containing thickened surfactant constituents desire the ability to formulate their products at ambient temperatures (cold processing). Accordingly, formulators desire thickeners, which can be introduced to the liquid surfactant compositions in liquid form rather than as a solid. This provides the formulator with a greater degree of precision in introducing the thickener to the liquid surfactant composition, allows the ability to formulate products at ambient temperatures (cold processing), and better facilitates automated processing without the need for special safety and handling equipment.

One important class of liquid rheology modifier commonly employed to thicken aqueous based surfactant containing formulations is the alkali-swellable or alkali-soluble emulsion (ASE) polymers. ASE polymers are linear or crosslinked copolymers that are synthesized from (meth)acrylic acid and alkyl acrylates. The crosslinked polymers immediately thicken upon neutralization with an inorganic or an organic base. As liquid emulsions, ASE polymers are easily processed and formulated into liquid surfactant containing formulations by the product formulator. Examples of ASE polymer thickened surfactant based formulations are set forth in U.S. Pat. No. 6,635,702; International Published Application No. WO 01/19946; and European Patent No. 1 690 878 B1, which disclose the use of a polymeric thickener for aqueous compositions containing surfactants. Although these thickeners offer a good viscosity, suspension and clarity properties in surfactant containing formulations at pH values near neutral (pH≥6.0), they become hazy at acidic pH ranges, resulting in poor clarity.

Microbial contamination from bacteria, yeast, and/or fungus in cosmetics, toiletries and personal care products is very common and has been of great concern to the industry for many years. Present day surfactant containing products are typically formulated with a preservative to protect the product from decay, discoloration, or spoilage and to ensure that the product is safe for topical application to the skin, scalp, and hair in humans and animals. Three classes of preservative compounds that are commonly used in surfactant containing products are the formaldehyde donors such as diazolinyl urea, imidazolinyl urea, and DMDM Hydantoin; the halogenated compounds including 2,4-dichlorobenzyl-alcohol, Chloroxylenol (4-chloro-3,5-dimethyl-phenol), Bronopol (2-bromo-2-nitropropane-1,3-diol), and iodopropynyl butyl carbamate; and the paraben compounds including methyl-paraben, ethyl-paraben, propyl-paraben, butyl-paraben, iso-propyl-paraben, and benzyl-paraben.

While these preservatives have been successfully utilized in personal care products for many years, there are recent concerns by the scientific community and the public that some of these compounds may constitute health hazards. Accordingly, there is an interest in replacing the above-mentioned compounds in surfactant containing products that are topically applied to or come into contact with human skin, scalp or hair while maintaining good antimicrobial efficacy, mildness, and do not raise safety concerns.

Organic acids (e.g., sorbic, citric and benzoic), such as those used as preservatives in the food industry, have been increasingly looked at as the ideal replacement for foregoing preservative systems in surfactant containing formulations. The antimicrobial activity of the organic acids is connected to the associated or protonated species of the acid molecule. As the pH of an organic acid containing formulation increases, dissociation of the proton occurs forming acid salts. The dissociated form of the organic acids (acid salts) have no antimicrobial activity when used alone, effectively limiting the use of organic based acids to pH values below 6 (Weber, K. 2005. New alternatives to paraben-based preservative blends. *Cosmetics & Toiletries* 120(1): 57-62).

The literature has also suggested that formulating products in the natural pH range (between about 3-5) 1) reduces the amount of preservative required in a product by enhancing preservative efficacy, 2) stabilizes and increases the effectiveness of many cosmetic active ingredients, 3) is beneficial to the repair and maintenance of skin barrier tissue, and 4) supports the natural skin flora to the exclusion of over-colonization by deleterious microorganisms (Wiechers, J. W. 2008. Formulating at pH 4-5: How lower pH benefits the skin and formulations. *Cosmetics & Toiletries* 123(12): 61-70).

As the industry desires new thickened surfactant based products that are formulated in the acidic pH range, there is a developing need for a rheology modifier that, when used in combination with a surfactant, provides a high clarity formulation under acidic pH conditions while maintaining a good viscosity/rheology profile, suspension (yield value), and enhanced aesthetics.

SUMMARY OF THE INVENTION

In one aspect, embodiments of the present invention relate to acrylic based polymer compositions comprising staged, structured, or core-shell polymer morphologies.

In one aspect, an embodiment of the invention relates to a staged core-shell polymer comprising an acrylic based linear (non-crosslinked) core stage polymer and an acrylic based crosslinked shell stage polymer.

In one aspect, an embodiment of the invention relates to a multi-staged polymer comprising a core polymer stage comprising an acrylic based linear polymer and at least one other stage comprising an acrylic based crosslinked polymer stage.

In one aspect, an embodiment of the invention relates to a thickened aqueous composition comprising a staged core-shell polymer of the invention.

In one aspect, an embodiment of the invention relates to a thickened aqueous composition comprising an acrylic based staged core-shell polymer and a surfactant selected from anionic, cationic, amphoteric and nonionic surfactants, and mixtures thereof.

In one aspect of the invention, embodiments relate to low pH aqueous compositions which have good rheological and clarity properties comprising an acrylic based staged core-shell polymer, an anionic surfactant, an amphoteric surfactant, a pH adjusting agent, and an optional surfactant selected from a cationic surfactant, a non-ionic surfactant, and mixtures thereof.

In one aspect of the invention, embodiments relate to low pH aqueous compositions which have good rheological and clarity properties comprising an acrylic based staged core-shell polymer, an anionic surfactant, an amphoteric surfactant, a pH adjusting agent, an acid based preservative, and an optional surfactant selected from a cationic surfactant, a non-ionic surfactant, and mixtures thereof.

In one aspect, embodiments of the invention relate to low pH, stable, aqueous personal care, home care, health care, and institutional and industrial care compositions having good rheological and clarity properties comprising an acrylic based staged core-shell polymer, an anionic surfactant, an amphoteric surfactant, a pH adjusting agent, an optional acid based preservative, and an optional surfactant selected from a cationic surfactant, a non-ionic surfactant, and mixtures thereof.

In one aspect, embodiments of the invention relate to stable personal care, home care, health care, and institutional and industrial care compositions having good rheological and clarity properties comprising an acrylic based staged core-shell polymer, an anionic surfactant, an amphoteric surfactant, a pH adjusting agent, an insoluble component and/or a particulate material that is stabilized or suspended in the composition, an optional acid based preservative, and an optional surfactant selected from a cationic surfactant, a non-ionic surfactant, and mixtures thereof.

In one aspect, embodiments of the invention relate to an aqueous surfactant containing composition formulated to a low pH comprising a staged core-shell polymer, an anionic surfactant, an amphoteric surfactant, a pH adjusting agent, and an optional surfactant selected from a cationic surfactant, a non-ionic surfactant, and mixtures thereof which composition has a combination of superior clarity and yield value properties.

In still a further aspect, the invention relates to a personal care, home care, health care, and industrial and institutional care composition comprising the staged core-shell polymer of the invention in combination with a benefit agent, adjuvant, and/or additive, with or without a surfactant.

These stable compositions can maintain a smooth, acceptable rheology, without significant increases or decreases in viscosity, with no separation, settling, or creaming out, or loss of clarity over extended periods of time, such as for at least one month at 45° C.

DESCRIPTION OF EXEMPLARY EMBODIMENTS

Figure 1:
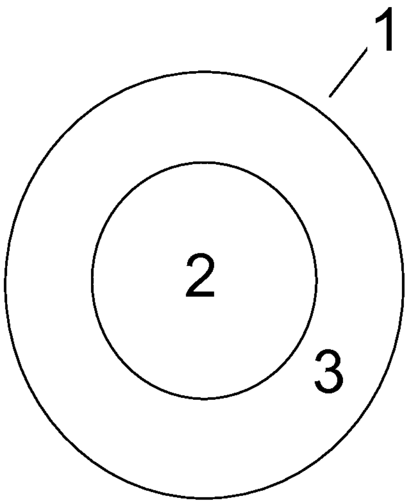
FIG. 1 represents a two stage core-shell polymer comprising a linear core polymer surrounded by or partially surrounded by a crosslinked shell polymer.

Exemplary embodiments in accordance with the present invention will be described. Various modifications, adaptations or variations of the exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

The polymers and compositions of the present invention may suitably comprise, consist of, or consist essentially of the components, elements, and process delineations described herein. The invention illustratively disclosed herein suitably may be practiced in the absence of any element which is not specifically disclosed herein.

Unless otherwise stated, all percentages, parts, and ratios expressed herein are based upon weight of the total compositions of the present invention.

As used herein and throughout the specification, the terms "core-shell morphology", "core-shell structure", "core-shell polymer", "structured polymer", "staged core-shell polymer" and "staged polymer" are used interchangeably and mean a polymer particle prepared by a sequential or staged polymerization process wherein each sequence or stage of monomer repeating units is polymerized to completion before the subsequent sequence or stage of repeating units are polymerized. These polymers have a structure in which a polymer(s) forming the core portion, sequence or stage and the polymer(s) forming the shell portion, sequence or stage are physically and/or chemically bonded and or attracted to each other. The structure and/or chemical composition (e.g., monomer composition and/or amount) of the copolymer particles of this invention changes from the inside to the outside of the particle and, as a result, these gradient zones can have different physical and chemical properties as well. These changes can be somewhat gradual, yielding a morphology having a gradient of polymeric structure or composition along any radius thereof. Alternatively, the change in polymeric structure or composition can be relatively well defined when moving outward along a radius of the particle from the center, yielding a morphology having a relatively distinct core portion comprising one polymeric composition, and a relatively distinct shell portion comprising a different polymeric composition. The staged core-shell morphology can comprise multiple layers or zones of differing polymeric composition as long as the core polymer defined herein is a linear polymer and at least one shell layer comprises a crosslinked polymer. The rate of change in the polymeric morphology of the particle is not particularly critical as long as the polymer exhibits the requisite properties described herein. Accordingly, as used herein, the terms "core" and "shell" refer to the polymeric content of the inside and the outside of the particle, respectively, and the use of said terms should not be construed as meaning that the polymer particles of this invention will necessarily exhibit a distinct interface between the polymers of the inside and the outside of the particle.

It is understood that the staged core-shell polymer particle can be not only a form in which the core portion is completely coated or encapsulated within the shell portion, but also a form in which the core portion is only partly coated or encapsulated. It is also to be understood that in describing the "core polymers" and the "shell polymers" of the staged core-shell polymers of the invention there can be a significant amount of interpenetration of the polymers residing in the core and shell of the polymer particles. Thus, the "core polymers" can extend somewhat into the shell of the particle forming a domain in the shell particle, and vice versa.

The terms "core polymers" and "shell polymers" and like terminology are employed herein to describe the polymeric material in the named portion of the polymeric particle in a general way without attempting to identify any particular polymers as strictly "shell" or strictly "core" polymers.

As used herein, the term "(meth)acrylic" acid is meant to include both acrylic acid and methacrylic acid. Similarly, the term "alkyl (meth)acrylate" as used herein is meant to include alkyl acrylate and alkyl methacrylate.

The term "low pH" refers to a pH value of 6 or below in one aspect, from about 0.5 to about 5.9 in another aspect, from about 2 to about 5.5 in a further aspect, and from about 3.5 to about 5 in a still further aspect.

The term "high clarity" means a turbidity value of ≤40 NTU in one aspect, ≤30 NTU in another aspect, and ≤20 NTU in a further aspect as measured in a thickened aqueous polymer/surfactant composition comprising 2.4% by weight polymer (active polymer solids) and 12.7% by weight of an anionic and amphoteric surfactant blend and the remainder water, wherein the anionic to amphoteric surfactant is present in a ratio of about 4.5:1 (calculated on a weight to weight basis of active surfactant), and wherein the pH of the thickened composition ranges from about 4.5. to about 5.

The term "personal care products" as used herein includes, without being limited thereto, cosmetics, toiletries, cosmeceuticals, beauty aids, insect repellents, personal hygiene and cleansing products applied to the body, including the skin, hair, scalp, and nails of humans and animals.

The term "home care products" as used herein includes, without being limited thereto, products employed in a domestic household for surface cleaning or maintaining sanitary conditions, such as in the kitchen and bathroom (e.g., hard surface cleaners, hand and automatic dish care, toilet bowl cleaners and disinfectants), and laundry products for fabric care and cleaning (e.g., detergents, fabric conditioners, pretreatment stain removers), and the like.

The term "health care products" as used herein includes, without being limited thereto, pharmaceuticals (controlled release pharmaceuticals), pharmacosmetics, oral care (mouth and teeth) products, such as oral suspensions, mouthwashes, toothpastes, dentifrices, and the like, and over-the-counter products and appliances (topical and transdermal), such as patches, plasters and the like, externally applied to the body, including the skin, scalp, nails and mucous membranes of humans and animals, for ameliorating a health-related or medical condition, for generally maintaining hygiene or well-being, and the like.

The term "institutional and industrial care" ("I&I") as used herein includes, without being limited thereto, products employed for surface cleaning or maintaining sanitary conditions in institutional and industrial environments, textile treatments (e.g., textile conditioners, carpet and upholstery cleaners), automobile care (e.g., hand and automatic car wash detergents, tire shines, leather conditioners, liquid car polishes, plastic polishes and conditioners), paints and coatings, and the like.

As used herein, the term "rheological properties" and grammatical variations thereof, includes, without limitation such properties as Brookfield viscosity, increase or decrease in viscosity in response to shear stress, flow characteristics, gel properties such as stiffness, resilience, flowability, and the like, foam properties such as foam stability, foam density, ability to hold a peak, and the like, suspension properties such as yield value, and aerosol properties such as ability to form aerosol droplets when dispensed from propellant based or mechanical pump type aerosol dispensers.

The term "aesthetic property" and grammatical variations thereof as applied to compositions refers to visual and tactile psychosensory product properties, such as color, clarity, smoothness, tack, lubricity, texture, conditioning and feel, and the like.

Here, as well as elsewhere in the specification and claims, individual numerical values (including carbon atom numerical values), or limits, can be combined to form additional non-disclosed and/or non-stated ranges.

The headings provided herein serve to illustrate, but not to limit the invention in any way or manner.

Core-Shell Polymer

Figure 2:
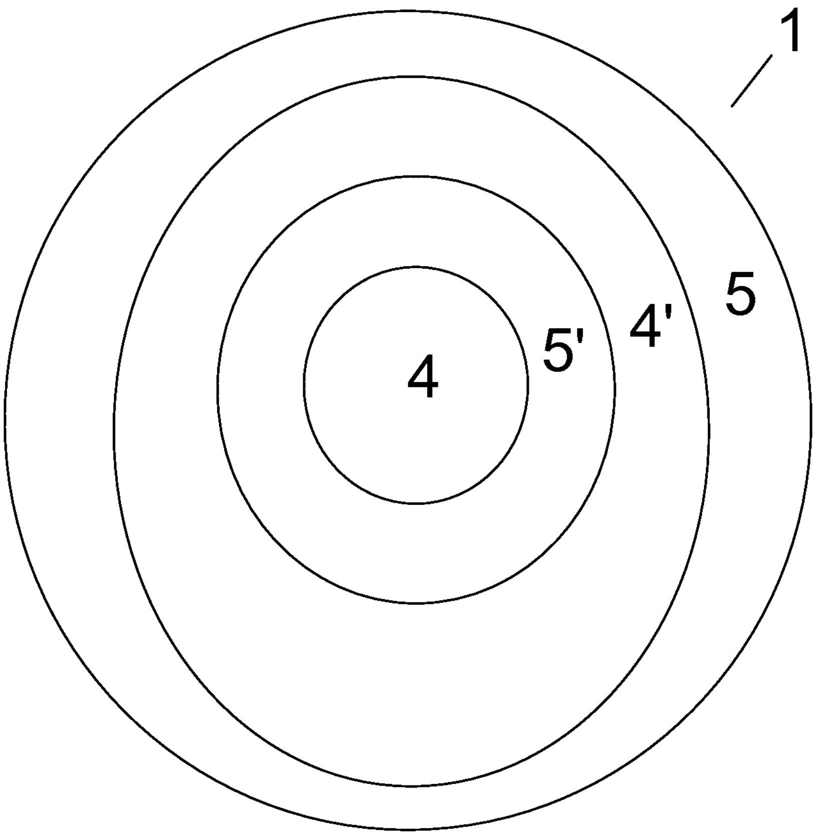
FIG. 2 represents a multi-staged core-shell polymer comprising an innermost linear polymer core and a crosslinked polymer shell. Contiguous polymeric stages are configured in alternating order of linear and crosslinked polymer types.
Figure 3:
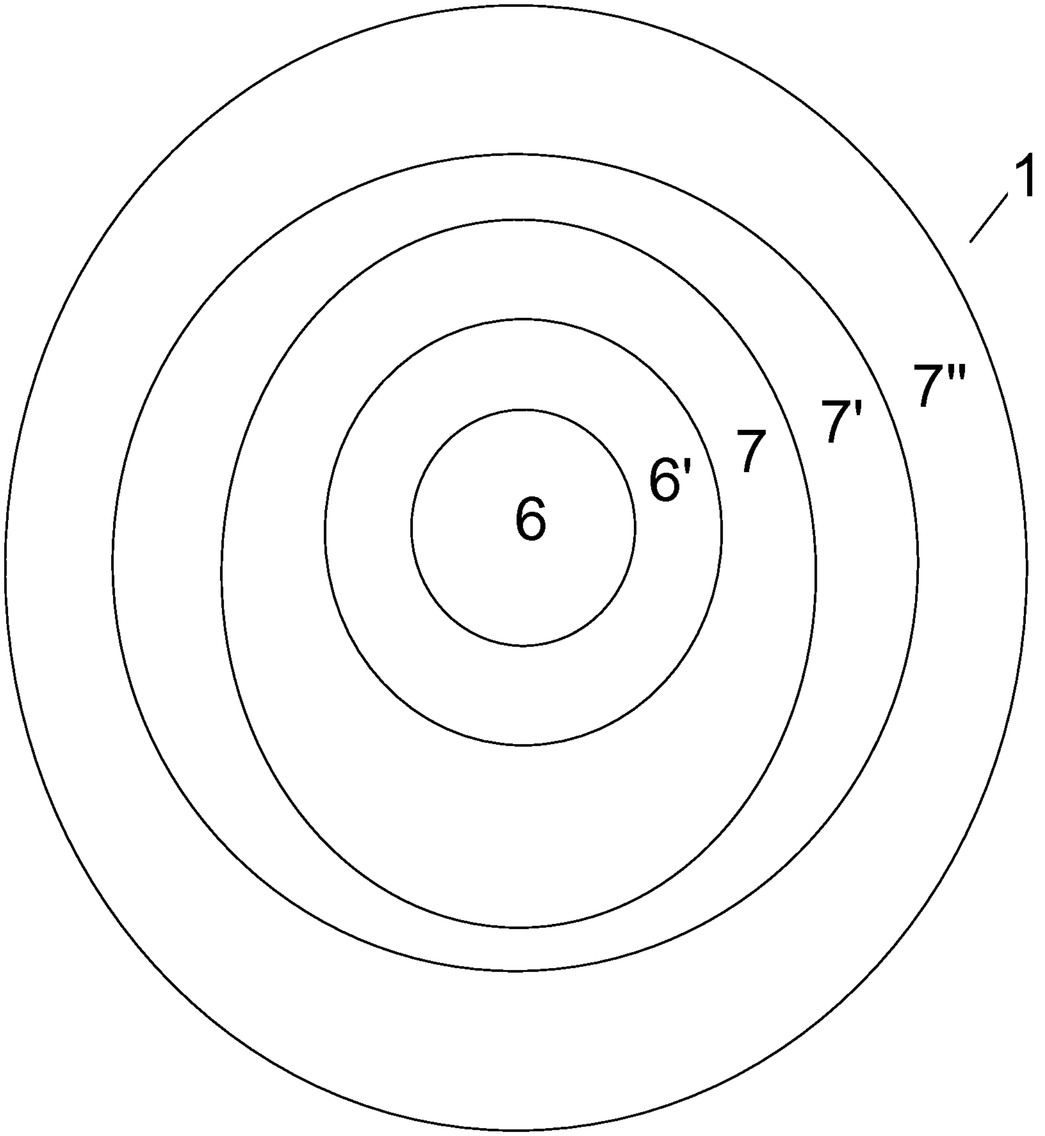
FIG. 3 represents a multi-stage core-shell polymer polymerized in random stage order. The polymer is configured to contain contiguous linear and crosslinked polymeric stages.

Staged core-shell polymers encompassed by the scope of the invention include, but are not limited, to those embodiments illustrated in the drawings. The staged core-shell polymers of the present invention are acrylic based copolymers comprising an linear core polymer and at least one crosslinked shell polymer. As represented in FIG. 1, the core-shell polymer 1 comprises at least two stages produced sequentially in emulsion, an innermost core or first stage 2 comprising a non-crosslinked or linear acrylic based copolymer and an outermost shell or last stage 3 comprising a crosslinked acrylic based copolymer. As shown in FIG. 2, a core-shell polymer 1 having intermediate stages of a linear polymer 4' and a crosslinked polymer 5' can be sequentially polymerized and situated between the innermost linear core stage polymer 4 and an outermost crosslinked shell stage polymer 5. Each linear and crosslinked polymer stage can be the same or different in terms of repeating unit composition and the relative amount monomeric repeating units in the backbone of the polymer. In a multiple staged core-shell polymer (a core-shell polymer comprising more than two stages), the configuration of the sequentially polymerized stages can be orderly, e.g., contiguous stages alternate between a linear polymer and a crosslinked polymer as in FIG. 2, or as illustrated in FIG. 3 the stage configuration of the core-shell polymer 1 of can be random, e.g., two or more contiguous stages can be linear 6, 6' or crosslinked 7, 7', 7", subject to the proviso that the innermost core stage 6 is a linear polymer (not crosslinked) and at least one of the outer shells, e.g., stage 7" is a crosslinked polymer.

In one aspect, the staged core-shell polymer comprises from about 5% to about 95% by weight of the acrylic based linear core polymer and from about 95% to about 5% by weight of the acrylic based crosslinked shell polymer, based on the total weight of the staged core-shell polymer. In another aspect, the staged core-shell polymer comprises from about 20% to about 80% by weight of the acrylic based linear core polymer and from about 80% to about 20% by weight of the acrylic based crosslinked shell polymer, based on the total weight of the staged core-shell polymer. In still another aspect, the staged core-shell polymer comprises from about 60% to about 40% by weight of the acrylic based linear core polymer and from about 40% to about 60% by weight of the acrylic based crosslinked shell polymer, based on the total weight of the staged core-shell polymer.

Core Polymer Component

The linear core polymer is an acrylic based linear polymer that is polymerized in the absence of a crosslinking monomer. In one embodiment, the core polymer is polymerized from a monomer mixture comprising a) a first monomeric component selected from one or more ethylenically unsaturated monomers containing at least one carboxylic acid group; b) a second ethylenically unsaturated monomeric component selected from at least one linear or branched $C_1$ to $C_5$ alkyl ester of (meth)acrylic acid, at least one $C_1$ to $C_5$ hydroxyalkyl ester of (meth)acrylic acid, and mixtures thereof; and c) optionally, at least one monomeric component selected from a monomer represented by the formulas:

$CH_2{=}C(R)C(O)OR^1$, i)

wherein R is selected from hydrogen or methyl; and $R^1$ is selected from $C_6$-$C_{10}$ alkyl, $C_6$ to $C_{10}$ hydroxyalkyl, $—(CH_2)_2OCH_2CH_3$, and $—(CH_2)_2C(O)OH$ and salts thereof;

$CH_2{=}C(R)X$, ii)

wherein R is hydrogen or methyl; and X is selected from $—C_6H_5$, $—CN$, $—C(O)NH_2$, $—NC_4H_6O$, $—C(O)NHC(CH_3)_3$, $—C(O)N(CH_3)_2$, $C(O)NHC(CH_3)_2(CH_2)_4CH_3$, and $—C(O)NHC(CH_3)_2CH_2S(O)(O)OH$ and salts thereof;

$CH_2{=}CHOC(O)R^1$, iii)

wherein $R^1$ is linear or branched $C_1$-$C_{18}$ alkyl; and $CH_2{=}C(R)C(O)OAOR^2$, iv)

wherein A is a divalent radical selected from $—CH_2CH(OH)CH_2—$ and $—CH_2CH(CH_2OH)—$, R is selected from hydrogen or methyl, and $R^2$ is an acyl residue of a linear or branched, saturated or unsaturated $C_{10}$ to $C_{22}$ fatty acid.

Exemplary ethylenically unsaturated monomers containing at least one carboxylic acid group which are set forth under monomeric component a) include (meth)acrylic acid, itaconic acid, citraconic acid, maleic acid, fumaric acid, crotonic acid, aconitic acid, and salts thereof, and mixtures thereof.

In one aspect of the invention, the amount of the at least one carboxylic acid group containing monomer set forth under first monomer component a) ranges from about 10% to 80% by weight, from about 20% to about 70% by weight in another aspect, and from about 35% to about 65% by weight in a further aspect based upon the total weight of the monomers.

Exemplary alkyl (meth)acrylate and hydroxyalkyl (meth) acrylate monomers set forth under monomeric component b) include methyl (meth)acrylate, ethyl (meth)acrylate, n-propyl (meth)acrylate, iso-propyl (meth)acrylate, n-butyl (meth) acrylate, isobutyl (meth)acrylate, t-butyl (meth)acrylate, n-amyl (meth)acrylate, iso-amyl (meth)acrylate, hydroxyethyl (meth)acrylate, hydroxypropyl (meth)acrylate, hydroxybutyl (meth)acrylate (butane diol mono(meth)acrylate), and mixtures thereof.

In one aspect of the invention, the alkyl and hydroxyalkyl (meth)acrylate monomers set forth under the second monomer component b) are utilized in an amount ranging from about 90% to about 20% by weight, from about 80% to about 25% by weight in another aspect, and from about 65% to about 35% by weight in still another aspect, based upon the total weight of the monomers.

Exemplary ethylenically unsaturated monomers set forth under formulas i) to iv) of optional monomeric component c) include ethyl diglycol (meth)acrylate, 2-carboxyethyl (meth) acrylate, n-hexyl (meth)acrylate, 2-ethylhexyl (meth)acrylate, octyl (meth)acrylate, decyl (meth)acrylate, 6-hydroxyhexyl (meth)acrylate, 10-hydroxydecyl (meth)acrylate, styrene, α-methyl styrene, acrylonitrile, methacrylonitrile, acrylamide, methacrylamide, N,N'-dimethylaminoacrylamide, t-butylacrylamide, t-octylacrylamide, N-vinyl pyrrolidone, 2-acrylamido-2-methylpropane sulfonic acid, vinyl acetate, vinyl propionate, vinyl butanoate, vinyl valerate, vinyl hexanoate, vinyl octanoate, vinyl nonanoate, vinyl decanoate, vinyl neodecanoate, vinyl laurate, ACE™ and (M)ACE™ monomer available from Hexion Specialty Chemicals, Inc., Columbus, Ohio; and mixtures thereof.

The foregoing monomers are commercially available and/or can be synthesized by procedures well known in the art.

The ACE monomer (CAS No. 94624-09-06) is the reaction product of glycidyl t-decanoate (CAS No. 71206-09-2) and acrylic acid. The (M)ACE Monomer is synthesized by reacting glycidyl t-decanoate and methacrylic acid.

Monomers set forth under formula iv) of optional monomer component c) can be synthesized via esterification by reacting glycidol with a $C_{10}$ to $C_{22}$ fatty acid to obtain the glycidyl ester of the respective fatty acid(s). The so-formed glycidyl ester in turn can be reacted through its epoxy functionality with the carboxyl moiety of (meth)acrylic acid to obtain a preformed monomer. Alternatively, the glycidyl ester of the fatty acid can be added to the polymerization mixture comprising the previously described monomers and reacted in situ with a portion of the one or more ethylenically unsaturated monomers containing at least one carboxylic acid group described under monomer component a), subject to the proviso that the reactant stoichiometry is designed such that only a portion of the carboxyl groups are reacted. In other words, sufficient acid functionality must be retained to serve the purpose of the present invention.

In one aspect of the invention, suitable glycidyl esters for forming the preformed and in situ formed monomer components described under formula iv) are disclosed in U.S. Pat. No. 5,179,157 (column 13). The relevant disclosure of which is herein incorporated by reference. A glycidyl ester of neodecanoic acid and isomers thereof is commercially available under the trade name Cardura™ E10P from Hexion Specialty Chemicals, Inc.

In one aspect of the invention, monomers set forth under formulas i) to iv) of optional monomer component c) are utilized in an amount ranging from about 0% to about 35% by weight, from about 1% to about 30% by weight in another aspect, from about 2% to about 15% by weight in still another aspect, and from about 5% to about 10% by weight in a further aspect, based upon the total weight of the monomers.

In another aspect of the invention, the non-crosslinked core polymer is polymerized from a monomer composition comprising:

a) from about 10% to about 80% by weight of at least one carboxylic acid monomer comprising acrylic acid, methacrylic acid, itaconic acid, fumaric acid, crotonic acid, aconitic acid, maleic acid, or combinations thereof;

b) from about 90% to about 20% by weight of at least one $C_1$ to $C_5$ alkyl ester and/or at least one $C_1$ to $C_5$ hydroxyalkyl ester of acrylic acid or methacrylic acid; and c) from about 0 to about 35 by weight of at least one α,β-ethylenically unsaturated monomer selected from a monomer represented by the formulas:

$$CH_2{=}C(R)C(O)OR^1, \qquad \text{i)}$$

wherein R is selected from hydrogen or methyl; and $R^1$ is selected from $C_6$-$C_{10}$ alkyl, $C_6$ to $C_{10}$ hydroxyalkyl, —$(CH_2)_2$ $OCH_2CH_3$, and —$(CH_2)_2C(O)OH$;

$$CH_2{=}C(R)X, \qquad \text{ii)}$$

wherein R is hydrogen or methyl; and X is selected from —$C_6H_5$, —CN, —$C(O)NH_2$, —$NC_4H_6O$, —C(O)NHC$(CH_3)_3$, —$C(O)N(CH_3)_2$, $C(O)NHC(CH_3)_2(CH_2)_4CH_3$, and —$C(O)NHC(CH_3)_2CH_2S(O)(O)OH$;

$$CH_2{=}CHOC(O)R^1, \qquad \text{iii)}$$

wherein $R^1$ is linear or branched $C_1$-$C_{18}$ alkyl; and $$CH_2{=}C(R)C(O)OAOR^2, \qquad \text{iv)}$$

wherein A is a divalent radical selected from —$CH_2CH(OH)CH_2$— and —$CH_2CH(CH_2OH)$—, R is selected from hydrogen or methyl, and $R^2$ is an acyl residue of a linear or branched, saturated or unsaturated $C_{10}$ to $C_{22}$ fatty acid.

In one aspect, the non-crosslinked linear polymer component has a viscosity value of greater than 500 mPa·s (Brookfield RVT, 20 rpm, spindle No. 1) measured as a 5 weight percent polymer solids concentration in deionized water and neutralized to pH 7 with a 18 weight percent NaOH solution.

In another aspect, the non-crosslinked, linear polymers of the core stage have a number average molecular weight ($M_n$) of greater than 100,000 daltons as measured by gel permeation chromatography (GPC) calibrated with a poly(methyl methacrylate) (PMMA) standard. In another aspect, the $M_n$ of the core polymer ranges from above about 100,000 daltons to about 500,000 daltons, from about 105,000 daltons to about 250,000 daltons in another aspect, from 110,000 daltons to about 200,000 daltons in still another aspect, and from 115,000 daltons to about 150,000 daltons in a further aspect.

Shell Polymer Component

The crosslinked shell polymer is an acrylic based crosslinked polymer that is polymerized from a monomer composition comprising a crosslinking monomer. In one embodiment, the shell polymer is polymerized from a monomer mixture comprising a1) a first monomeric component selected from one or more ethylenically unsaturated monomers containing at least one carboxylic acid group; b1) a second ethylenically unsaturated monomeric component selected from at least one linear or branched $C_1$ to $C_5$ alkyl ester of (meth)acrylic acid, at least one $C_1$ to $C_5$ hydroxyalkyl ester of (meth)acrylic acid, and mixtures thereof; c1) a third monomeric component selected from at least one compound having reactive groups capable of crosslinking the shell polymer, and optionally d1), at least one monomeric component selected from a monomer represented by the formulas:

$$CH_2{=}C(R)C(O)OR^1, \qquad \text{i)}$$

wherein R is selected from hydrogen or methyl; and $R^1$ is selected from $C_6$-$C_{10}$ alkyl, $C_6$ to $C_{10}$ hydroxyalkyl, —$(CH_2)_2$ $OCH_2CH_3$, and —$(CH_2)_2C(O)OH$ and salts thereof;

$$CH_2{=}C(R)X, \qquad \text{ii)}$$

wherein R is hydrogen or methyl; and X is selected from —$C_6H_5$, —CN, —$C(O)NH_2$, —$NC_4H_6O$, —C(O)NHC$(CH_3)_3$, —$C(O)N(CH_3)_2$, $C(O)NHC(CH_3)_2(CH_2)_4CH_3$, and —$C(O)NHC(CH_3)_2CH_2S(O)(O)OH$ and salts thereof;

$$CH_2{=}CHOC(O)R^1, \qquad \text{iii)}$$

wherein $R^1$ is linear or branched $C_1$-$C_{18}$ alkyl; and $$CH_2{=}C(R)C(O)OAOR^2, \qquad \text{iv)}$$

wherein A is a divalent radical selected from —$CH_2CH(OH)CH_2$— and —$CH_2CH(CH_2OH)$—, R is selected from hydrogen or methyl, and $R^2$ is an acyl residue of a linear or branched, saturated or unsaturated $C_{10}$ to $C_{22}$ fatty acid.

Exemplary ethylenically unsaturated monomers containing at least one carboxylic acid group which are set forth under monomeric component a1) include (meth)acrylic acid, itaconic acid, citraconic acid, maleic acid, fumaric acid, crotonic acid, aconitic acid, and salts thereof, and mixtures thereof.

In one aspect of the invention, the amount of the at least one carboxylic acid group containing monomer set forth under first monomer component a) ranges from about 10% to 80% by weight, from about 20% to about 70% by weight in another aspect, and from about 35% to about 65% by weight in a further aspect based upon the total weight of the monomers.

Exemplary alkyl (meth)acrylate and hydroxyalkyl (meth)acrylate monomers set forth under monomeric component b) include methyl (meth)acrylate, ethyl (meth)acrylate, n-propyl (meth)acrylate, iso-propyl (meth)acrylate, n-butyl (meth)acrylate, isobutyl (meth)acrylate, t-butyl (meth)acrylate, n-amyl (meth)acrylate, iso-amyl (meth)acrylate, hydroxyethyl (meth)acrylate, hydroxypropyl (meth)acrylate, hydroxybutyl (meth)acrylate (butane diol mono(meth)acrylate), and mixtures thereof.

In one aspect of the invention, the alkyl and hydroxyalkyl (meth)acrylate monomers set forth under the second monomer component b1) are utilized in an amount ranging from about 90% to about 15% by weight, from about 80% to about 25% by weight in another aspect, and from about 65% to about 35% by weight in still another aspect, based upon the total weight of the monomers.

In one aspect of the invention, the third monomeric component c1) is selected from at least one crosslinking monomer. A crosslinking monomer(s) is utilized to generate a polymer having either a partially or substantially-crosslinked three-dimensional network. In one aspect, the crosslinking monomer is a polyunsaturated compound. Exemplary polyunsaturated compounds include di(meth)acrylate compounds such as ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl)propane, 2,2'-bis(4-(acryloxydiethoxy-phenyl)propane, and zinc acrylate (i.e., $2(C_3H_3O_2)Zn^{++}$); tri(meth)acrylate compounds such as, trimethylolpropane tri(meth)acrylate, trimethylolethane tri(meth)acrylate, and tetramethylolmethane tri(meth)acrylate; tetra(meth)acrylate compounds such as ditrimethylolpropane tetra(meth)acrylate, tetramethylolmethane tetra(meth)acrylate, and pentaerythritol tetra(meth)acrylate; hexa(meth)acrylate compounds such as dipentaerythritol hexa(meth)

acrylate; allyl compounds such as allyl (meth)acrylate, diallylphthalate, diallyl itaconate, diallyl fumarate, and diallyl maleate; polyallyl ethers of sucrose having from 2 to 8 alkyl groups per molecule, polyallyl ethers of pentaerythritol such as pentaerythritol diallyl ether, pentaerythritol triallyl ether, and pentaerythritol tetraallyl ether; polyallyl ethers of trimethylolpropane such as trimethylolpropane diallyl ether and trimethylolpropane triallyl ether. Other suitable polyunsaturated compounds include divinyl glycol, divinyl benzene, and methylenebisacrylamide.

In another aspect, suitable polyunsaturated monomers can be synthesized via an esterification reaction of a polyol made from ethylene oxide or propylene oxide or combinations thereof with unsaturated anhydride such as maleic anhydride, citraconic anhydride, itaconic anhydride, or an addition reaction with unsaturated isocyanate such as 3-isopropenyl-α-α-dimethylbenzene isocyanate.

In addition, the following unsaturated compounds can be utilized as crosslinkers which are reactive with pendant carboxyl groups on the polymer backbone: polyhaloalkanols such as 1,3-dichloroisopropanol and 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin, and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers, bisphenol A-epichlorohydrin epoxy resins and mixtures of the foregoing. Mixtures of two or more of the foregoing polyunsaturated compounds can also be utilized to crosslink the shell polymer component of the present invention.

The crosslinking monomer component can be used in an amount ranging from about 0.01 to about 5% by weight in one aspect, from about 0.03 to about 3% by weight in another aspect, and from about 0.05 to about 1% by weight in a further aspect, based upon the total weight of all of the monomers forming the acrylate based shell polymer component.

Exemplary ethylenically unsaturated monomers set forth under formulas i) to iv) of optional monomeric component d1) include ethyl diglycol (meth)acrylate, 2-carboxyethyl (meth)acrylate, n-hexyl (meth)acrylate, 2-ethylhexyl (meth) acrylate, octyl (meth)acrylate, decyl (meth)acrylate, 6-hydroxyhexyl (meth)acrylate, 10-hydroxydecyl (meth)acrylate, styrene, α-methyl styrene, acrylonitrile, methacrylonitrile, acrylamide, methacrylamide, N,N'-dimethylaminoacrylamide, t-butylacrylamide, t-octylacrylamide, N-vinyl pyrrolidone, 2-acrylamido-2-methylpropane sulfonic acid, vinyl acetate, vinyl propionate, vinyl butanoate, vinyl valerate, vinyl hexanoate, vinyl octanoate, vinyl nonanoate, vinyl decanoate, vinyl neodecanoate, vinyl laurate, ACE™ and (M)ACE™ monomer available from Hexion Specialty Chemicals, Inc., Columbus, Ohio; and mixtures thereof.

The foregoing monomers are commercially available and/or can be synthesized by procedures well known in the art, or as described herein.

As previously disclosed for the monomers of formula c)(iv), monomers conforming to formula iv) of optional monomer component d1) can be synthesized by reacting glycidol with a $C_{10}$ to $C_{22}$ fatty acid to obtain a glycidyl ester intermediate which in turn can be reacted through its epoxy functionality with the carboxyl moiety of (meth)acrylic acid to obtain a preformed monomer. Alternatively, the glycidyl ester intermediate can be added to the polymerization mixture comprising the previously described monomers and reacted in situ with a portion of the one or more ethylenically unsaturated monomers containing at least one carboxylic acid group described under monomer component a), subject to the proviso that the reactant stoichiometry is designed such that only a portion of the carboxyl groups are reacted.

In one aspect of the invention, monomers set forth under formulas i) to iv) of optional monomer component d1) are utilized in an amount ranging from about 0% to about 35% by weight, from about 1% to about 30% by weight in another aspect, from about 2% to about 15% by weight in still another aspect, and from about 5% to about 10% by weight in a further aspect, based upon the total weight of the monomers.

None of the monomers used to polymerize the core and shell polymers of the present invention are associative monomers. Associative monomers are ethylenically polymerizable monomers that contain a polyalkoxide hydrophilic segment terminated with a hydrophobic group. The polyalkoxide segment usually consists of polyethylene oxide units or polypropylene oxide units or combinations thereof situated between the ethylenic unsaturation at one terminus of the molecule and a terminal hydrophobe situated at the other terminus. The hydrophobe can be selected from a long chain hydrocarbon group containing 8 to 30 carbon atoms. Polymers which incorporate associative monomers are referred to in the art as hydrophobically modified linear emulsion (HASE) polymers.

Core-Shell Polymer Preparation

The staged core-shell polymer of the invention comprises a linear core and a crosslinked shell attached and/or associated with said core. Upon neutralizing the core polymer with a base, the core polymer remains attached or associated with the shell polymer. The staged core-shell polymer of the invention comprises at least two polymeric stages synthesized sequentially via staged free radical emulsion polymerization techniques known to the art.

The core polymer or stage is synthesized in a first emulsion polymerization stage from a monomer mixture emulsified in an aqueous phase comprising core monomers a), b), and optionally c) as disclosed above. The mixture of monomers for formation of the core is devoid of crosslinking monomers. The emulsified core monomers are polymerized in the presence of a suitable free radical forming initiator to provide an emulsion of a non-crosslinked linear core stage polymer. Correspondingly, a shell stage polymer is formed in a second emulsion polymerization stage. In this second stage, an emulsified monomer mixture comprising shell monomers a1), b1), crosslinking monomer c1), and optional monomer d1) (as previously disclosed) is polymerized in the presence of the previously prepared first stage latex of the core stage polymer and additional free radical forming initiator. The end-product is a two stage polymer comprising a linear non-crosslinked core surrounded or partially surrounded with a crosslinked shell. Alternatively, a preformed liner seed emulsion polymer can be utilized as the core polymer followed by the formation of the shell polymer in a second stage as described above.

In another aspect of the invention, the core polymer can be synthesized via successive free radical emulsion polymerization stages to obtain a multi-layered or multi-staged core polymer. The core monomer mixture utilized to polymerize each successive layer or stage may be the same or different than utilized in the polymerization layer or stage immediately preceding it. Similarly, the shell polymer can be synthesized via successive free radical emulsion polymerization stages to obtain a multi-layered or multi-staged shell polymer. As with the core monomer mixture, the shell monomer mixture utilized to polymerize successive shell layers or stages may be the same or different than utilized in the polymerization layer or stage immediately preceding it.

Alternatively, successive free radical emulsion polymerization stages can be run to obtain multi-stage polymer morphologies such that successive polymer stages differ by polymer type (i.e., linear or crosslinked), subject to the proviso that the core or first stage polymer must be linear and at least one of the shell polymer stages must be crosslinked. In a stage where it is desired to have a linear polymer, the emulsion polymerizable monomer mixture will be devoid of crosslinking monomer, and in a stage where it is desired to have a crosslinked polymer the emulsion polymerizable monomer mixture will comprise a crosslinking monomer.

Each stage of the core-shell polymers of the invention can be prepared from a monomer mixture comprising one or more chain transfer agents. The chain transfer agent can be any chain transfer agent which reduces the molecular weight of the staged polymers of the invention. Suitable chain transfer agents include, but are not limited to, thio and disulfide containing compounds, such as $C_1$-$C_{18}$ alkyl mercaptans, mercaptocarboxylic acids, mercaptocarboxylic esters, thioesters, $C_1$-$C_{18}$ alkyl disulfides, aryldisulfides, polyfunctional thiols such as trimethylolpropane-tris-(3-mercaptopropionate), pentaerythritol-tetra-(3-mercaptopropionate), pentaerythritol-tetra-(thioglycolate), and pentaerythritol-tetra-(thiolactate), dipentaerythritol-hexa-(thioglycolate), and the like; phosphites and hypophosphites; haloalkyl compounds, such as carbon tetrachloride, bromotrichloromethane, and the like; and catalytic chain transfer agents such as, for example, cobalt complexes (e.g., cobalt (II) chelates).

In one aspect of the invention, the chain transfer agent is selected from octyl mercaptan, n-dodecyl mercaptan, t-dodecyl mercaptan, hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, and dodecyl thioglycolate.

When utilized, the chain transfer agent can be present in an amount ranging from about 0.1% to 10% by weight, based on the total monomer mixture weight.

The emulsion polymerization can be carried out in a staged batch process, in a staged metered monomer addition process, or the polymerization can be initiated as a batch process and then the bulk of the monomers can be continuously staged into the reactor (seed process). Typically, the polymerization process is carried out at a reaction temperature in the range of about 20 to about 99° C., however, higher or lower temperatures can be used. To facilitate emulsification of the monomer mixture, the emulsion polymerization is carried out in the presence of at least one surfactant. In one embodiment, the emulsion polymerization is carried out in the presence of surfactant ranging in the amount of about 1% to about 10% by weight in one aspect, from about 3% to about 8% in another aspect, and from about 3.5% to about 7% by weight in a further aspect, based on a total emulsion weight basis. The emulsion polymerization reaction mixture also includes one or more free radical initiators which are present in an amount ranging from about 0.01% to about 3% by weight based on total monomer weight. The polymerization can be performed in an aqueous or aqueous alcohol medium.

Surfactants for facilitating emulsion polymerizations include anionic, nonionic, amphoteric, and cationic surfactants, as well as mixtures thereof. Most commonly, anionic and nonionic surfactants can be utilized as well as mixtures thereof.

Suitable anionic surfactants for facilitating emulsion polymerizations are well known in the art and include, but are not limited to, sodium lauryl sulfate, sodium dodecyl benzene sulfonate, sodium ($C_6$-$C_{16}$) alkyl phenoxy benzene sulfonate, disodium ($C_6$-$C_{16}$) alkyl phenoxy benzene sulfonate, disodium ($C_6$-$C_{16}$) di-alkyl phenoxy benzene sulfonate, disodium laureth-3 sulfosuccinate, sodium dioctyl sulfosuccinate, sodium di-sec-butyl naphthalene sulfonate, disodium dodecyl diphenyl ether sulfonate, disodium n-octadecyl sulfosuccinate, phosphate esters of branched alcohol ethoxylates, and the like.

Nonionic surfactants suitable for facilitating emulsion polymerizations are well known in the polymer art, and include, without limitation, linear or branched $C_8$-$C_{30}$ fatty alcohol ethoxylates, such as capryl alcohol ethoxylate, lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and, behenyl alcohol ethoxylate; alkylphenol alkoxylates, such as octylphenol ethoxylates; and polyoxyethylene polyoxypropylene block copolymers, and the like. Additional fatty alcohol ethoxylates suitable as non-ionic surfactants are described below. Other useful nonionic surfactants include $C_8$-$C_{22}$ fatty acid esters of polyoxyethylene glycol, ethoxylated mono- and diglycerides, sorbitan esters and ethoxylated sorbitan esters, $C_8$-$C_{22}$ fatty acid glycol esters, block copolymers of ethylene oxide and propylene oxide, and combinations thereof. The number of ethylene oxide units in each of the foregoing ethoxylates can range from 2 and above in one aspect, and from 2 to about 150 in another aspect.

Exemplary free radical initiators include, but are not limited to, water-soluble inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid; and oil soluble, free radical producing agents, such as 2,2'-azobisisobutyronitrile, and the like, and mixtures thereof. Peroxides and peracids can optionally be activated with reducing agents, such as sodium bisulfite, sodium formaldehyde, or ascorbic acid, transition metals, hydrazine, and the like. Particularly suitable free-radical polymerization initiators include water soluble azo polymerization initiators, such as 2,2'-azobis(tert-alkyl) compounds having a water solubilizing substituent on the alkyl group. Preferred azo polymerization catalysts include the Vazo® free-radical polymerization initiators, available from DuPont, such as Vazo® 44 (2,2'-azobis(2-(4,5-dihydroimidazolyl)propane), Vazo® 56 (2,2'-azobis(2-methylpropionamidine)dihydrochloride), and Vazo® 68 (4,4'-azobis(4-cyanovaleric acid)).

Optionally, other emulsion polymerization additives and processing aids which are well known in the emulsion polymerization art, such as auxiliary emulsifiers, solvents, buffering agents, chelating agents, inorganic electrolytes, polymeric stabilizers, and pH adjusting agents can be included in the polymerization system.

In one aspect, an auxiliary emulsifying aid selected from an ethoxylated $C_{10}$ to $C_{22}$ fatty alcohol (or their mixtures) can be added to the polymerization medium. In one aspect, the fatty alcohol contains from about 5 to about 250 moles of ethoxylation, from about 8 to 100 moles in another aspect, and from about 10 to 50 moles in a further aspect. Exemplary ethoxylated fatty alcohols include lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and behenyl alcohol ethoxylate. In another aspect, suitable ethoxylated fatty alcohols include Ceteth-20, Ceteareth-20, and Steareth-20, Behenth-25, and mixtures thereof.

If employed, the amount of ethoxylated fatty alcohol can range from about 0.1% to 10% by weight in one aspect, from about 0.5% to about 8% by weight in another aspect, and from about 1% to about 5% by weight in a further aspect, based on the total weight percent of the monomers present in the polymerization medium.

In a typical two-stage polymerization, a mixture of core stage monomers is added to a first reactor under inert atmosphere to a solution of emulsifying surfactant (e.g., anionic surfactant) in water. Optional processing aids can be added as desired (e.g., auxiliary emulsifier(s)). The contents of the reactor are agitated to prepare a monomer emulsion. To a second reactor equipped with an agitator, an inert gas inlet, and feed pumps are added under inert atmosphere a desired amount of water and additional anionic surfactant and optional processing aids. The contents of the second reactor are heated with mixing agitation. After the contents of the second reactor reaches a temperature in the range of about 55 to 98° C., a free radical initiator is injected into the so formed aqueous surfactant solution in the second reactor, and a portion of the monomer emulsion from the first reactor is gradually metered into the second reactor over a period typically ranging from about one half to about four hours. The reaction temperature is controlled in the range of about 45 to about 95° C. After completion of the core monomer addition, an additional quantity of free radical initiator can optionally be added to the second reactor, if desired, and the resulting reaction mixture is typically held at a temperature of about 45 to 95° C. for a time period sufficient to complete the polymerization reaction and obtain a first stage core polymer particle emulsion.

To the first reactor containing the remaining emulsion of core stage monomers a polyunsaturated crosslinking monomer is added and emulsified therewith to form a shell stage or second stage monomer emulsion. Additional shell stage monomers can be emulsified into the mixture if desired. Alternatively, a shell stage monomer emulsion containing a desired complement of shell stage monomers, including a polyunsaturated crosslinking monomer, can be formed in a separate reactor following the same procedures as outlined for formulating the core stage emulsion of monomers. The shell stage or second stage monomers with crosslinker are metered into the second reactor at a constant rate and mixed with the core polymer emulsion. Simultaneous with the shell stage monomer feed, a free radical initiator in an amount sufficient to initiate polymerization is metered into the reaction mixture where the shell stage or second stage monomers are polymerized in the presence of the core stage or first stage polymer. The temperature is maintained at about 85° C. for about 2.5 hours or until polymerization is complete. Unreacted monomer can be eliminated by addition of more initiator, as is well known in the emulsion polymerization art. Typically, the staged core-shell polymer or staged polymer emulsion product has a total polymer solids content in the range of about 10 to about 45 weight percent. While the polymer is synthesized in an emulsion, it should be recognized that the staged core-shell polymer can be supplied in dried powder form if desired.

While a typical two-stage polymer process is generally described immediately above, multi-staged or multi-layered polymers can be formed through the sequential emulsion polymerization of monomer charges in the presence of polymer particles of a previously formed emulsion polymer.

Surfactants

In one aspect, an embodiment of the present invention relates to stable, aqueous compositions comprising a staged core-shell acrylic based rheology modifier and a surfactant(s). Suitable surfactants include anionic, cationic, amphoteric, and nonionic surfactants, as well as mixtures thereof. Such compositions are useful in personal care cleansing compositions that contain various components such as substantially insoluble materials requiring suspension or stabilization (e.g., a silicone, an oily material, a pearlescent material, aesthetic and cosmeceutical beads and particles, gaseous bubbles, exfoliants, and the like). The invention further relates to the incorporation of an acidic materials before or after the addition of an alkaline material to reduce the pH of the composition without negatively impacting the viscosity, rheological, and clarity properties of the composition.

The anionic surfactant can be any of the anionic surfactants known or previously used in the art of aqueous surfactant compositions. Suitable anionic surfactants include but are not limited to alkyl sulfates, alkyl ether sulfates, alkyl sulphonates, alkaryl sulfonates, α-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants contain from about 6 to about 24 carbon atoms in one aspect, from 8 to 22 carbon atoms in another aspect and from about 12 to 18 carbon atoms in a further aspect and may be unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from about 8 to about 22 carbon atoms.

The cationic surfactants can be any of the cationic surfactants known or previously used in the art of aqueous surfactant compositions. Suitable classes of cationic surfactants include but are not limited to alkyl amines, alkyl imidazolines, ethoxylated amines, quaternary compounds, and quaternized esters. In addition, alkyl amine oxides can function as a cationic surfactant at a low pH.

Alkylamine surfactants can be salts of primary, secondary and tertiary fatty $C_{12}$-$C_{22}$ alkylamines, substituted or unsubstituted, and substances sometimes referred to as "amidoamines". Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane).

Non-limiting examples of amidoamines and salts thereof include stearamido propyl dimethyl amine, stearamidopropyl dimethylamine citrate, palmitamidopropyl diethylamine, and cocamidopropyl dimethylamine lactate.

Non-limiting examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Non-limiting examples of ethyoxylated amines include PEG-cocopolyamine, PEG-15 tallow amine, quaternium-52, and the like.

Among the quaternary ammonium compounds useful as cationic surfactants, some correspond to the general formula: $(R^5R^6R^7R^8N^+)\ E^-$, wherein $R^5$, $R^6$, $R^7$, and $R^8$ are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g., chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated. In one aspect, the aryl groups are selected from phenyl and benzyl.

Exemplary quaternary ammonium surfactants include, but are not limited to cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride, benzalkonium chloride, benzethonium chloride, and di(coconutalkyl)dimethyl ammonium chloride, ditallowedimethyl ammonium chloride, di(hydrogenated tallow)dimethyl ammonium chloride, di(hydrogenated tallow)dimethyl ammonium acetate, ditallowedimethyl ammonium methyl sulfate, ditallow dipropyl ammonium phosphate, and ditallow dimethyl ammonium nitrate.

At low pH, amine oxides can protonate and behave similarly to N-alkyl amines. Examples include, but are not limited to, dimethyl-dodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl C12-15 alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

Amphoteric or zwitterionic surfactants are molecules that contain acidic and basic moieties and have the capacity of behaving either as an acid or a base. Suitable surfactants can be any of the amphoteric surfactants known or previously used in the art of aqueous surfactant compositions. Exemplary amphoteric surfactant classes include but are not limited to amino acids (e.g., N-alkyl amino acids and N-acyl amino acids), betaines, sultaines, and alkyl amphocarboxylates.

Amino acid based surfactants suitable in the practice of the present invention include surfactants represented by the formula:

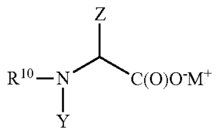

wherein $R^{10}$ represents a saturated or unsaturated hydrocarbon group having 10 to 22 carbon atoms or an acyl group containing a saturated or unsaturated hydrocarbon group having 9 to 22 carbon atoms, Y is hydrogen or methyl, Z is selected from hydrogen, $—CH_3$, $—CH(CH_3)_2$, $—CH_2CH(CH_3)_2$, $—CH(CH_3)CH_2CH_3$, $—CH_2C_6H_5$, $—CH_2C_6H_4OH$, $—CH_2OH$, $—CH(OH)CH_3$, $—(CH_2)_4NH_2$, $—(CH_2)_3NHC(NH)NH_2$, $—CH_2C(O)O^-M^+$, $—(CH_2)_2C(O)O^-M^+$. M is a salt forming cation. In one aspect, $R^{10}$ represents a radical selected from a linear or branched $C_{10}$ to $C_{22}$ alkyl group, a linear or branched $C_{10}$ to $C_{22}$ alkenyl group, an acyl group represented by $R^{11}C(O)—$, wherein $R^{11}$ is selected from a linear or branched $C_9$ to $C_{22}$ alkyl group, a linear or branched $C_9$ to $C_{22}$ alkenyl group. In one aspect, $M^+$ is selected from sodium, potassium, ammonium, and triethanolamine (TEA).

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants are, but not limited to the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

The betaines and sultaines useful in the present invention are selected from alkyl betaines, alkylamino betaines, and alkylamido betaines, as well as the corresponding sulfobetaines (sultaines) represented by the formulas:

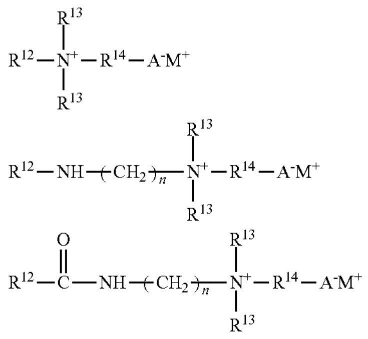

wherein $R^{12}$ is a $C_7$-$C_{22}$ alkyl or alkenyl group, each $R^{13}$ independently is a $C_1$-$C_4$ alkyl group, $R^{14}$ is a $C_1$-$C_5$ alkylene group or a hydroxy substituted $C_1$-$C_5$ alkylene group, n is an integer from 2 to 6, A is a carboxylate or sulfonate group, and M is a salt forming cation. In one aspect, $R^{12}$ is a $C_{11}$-$C_{18}$ alkyl group or a $C_{11}$-$C_{18}$ alkenyl group. In one aspect, $R^{13}$ is methyl. In one aspect, $R^{14}$ is methylene, ethylene or hydroxy propylene. In one aspect, n is 3. In a further aspect, M is selected from sodium, potassium, magnesium, ammonium, and mono-, di- and triethanolamine cations.

Examples of suitable betaines include, but are not limited to, lauryl betaine, coco betaine, oleyl betaine, cocohexadecyl dimethylbetaine, lauryl amidopropyl betaine, cocoamidopropyl betaine, and cocamidopropyl hydroxysultaine.

The alkylamphocarboxylates such as the alkylamphoacetates and alkylamphopropionates (mono- and disubstituted carboxylates) can be represented by the formula:

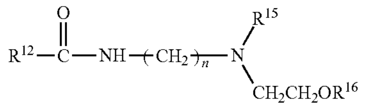

wherein $R^{12}$ is a $C_7$-$C_{22}$ alkyl or alkenyl group, $R^{15}$ is $—CH_2C(O)O^-M^+$, $—CH_2CH_2C(O)O^-M^+$, or $—CH_2CH(OH)CH_2SO_3^-M^+$, $R^{16}$ is a hydrogen or $—CH_2C(O)O^-M^+$, and M is a cation selected from sodium, potassium, magnesium, ammonium, and mono-, di- and triethanolamine.

Exemplary alkylamphocarboxylates include, but are not limited to, sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

The nonionic surfactant can be any of the nonionic surfactants known or previously used in the art of aqueous surfactant compositions. Suitable nonionic surfactants include, but are not limited to, aliphatic ($C_6$-$C_{18}$) primary or secondary linear or branched chain acids, alcohols or phenols; alkyl ethoxylates; alkyl phenol alkoxylates (especially ethoxylates and mixed ethoxy/propoxy moieties); block alkylene oxide condensates of alkyl phenols; alkylene oxide condensates of alkanols; and ethylene oxide/propylene oxide block copolymers. Other suitable nonionic surfactants include mono- or dialkyl alkanolamides; alkyl polyglucosides (APGs); sorbitan fatty acid esters; polyoxyethylene sorbitan fatty acid esters; polyoxyethylene sorbitol esters; polyoxyethylene acids, and polyoxyethylene alcohols. Other examples of suitable nonionic surfactants include coco mono- or diethanolamide, coco glucoside, decyl diglucoside, lauryl diglucoside, coco diglucoside, polysorbate 20, 40, 60, and 80, ethoxylated linear alcohols, cetearyl alcohol, lanolin alcohol, stearic acid, glyceryl stearate, PEG-100 stearate, laureth 7, and oleth 20.

In another embodiment, non-ionic surfactants include, but are not limited to, alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357, the disclosures of which are hereby incorporated by reference in their entirety.

Other surfactants which can be utilized in the present invention are set forth in more detail in WO 99/21530, U.S. Pat. No. 3,929,678, U.S. Pat. No. 4,565,647, U.S. Pat. No. 5,720,964, and U.S. Pat. No. 5,858,948. In addition, suitable surfactants are also described in *McCutcheon's Emulsifiers and Detergents* (North American and International Editions, by Schwartz, Perry and Berch) which is hereby fully incorporated by reference.

While the amounts of the surfactant utilized in a composition comprising the staged core-shell polymer of the invention can vary widely depending on a desired application, the amounts which are often utilized generally range from about 1% to about 80% by weight in one aspect, from about 3% to about 65% weight in another aspect, from about 5% to about 30% by weight in a still another aspect, from about 6% to about 20% by weight in a further aspect, and from about 8% to about 16% by weight, based upon the total weight of the personal care, home care, heath care, and institutional and industrial care composition in which it is included.

In one aspect of the invention, the personal care, home care, health care and I&I care compositions of the invention comprise a staged core-shell polymer in combination with at least one anionic surfactant. In another aspect of the invention, the compositions comprise a staged core-shell polymer with at least one anionic surfactant and at least one amphoteric surfactant. In one aspect, the anionic surfactant is selected from alkyl sulfates, alkyl ether sulfates, alkyl sulphonates, alkaryl sulfonates, alkarylpolyether sulphates, and mixtures thereof wherein the alkyl group contains 10 to 18 carbon atoms, the aryl group is a phenyl, and the ether group contains 1 to 10 moles of ethylene oxide. Representative anionic surfactants include, but are not limited to, sodium and ammonium lauryl ether sulfate (ethoxylated with 1, 2, and 3 moles of ethylene oxide), sodium, ammonium, and triethanolamine lauryl sulfate.

In one aspect, the amphoteric surfactant is selected from an alkyl betaine, an alkylamino betaine, an alkylamido betaines, and mixtures thereof. Representative betaines include but are not limited to lauryl betaine, coco betaine, cocohexadecyl dimethylbetaine, cocoamidopropyl betaine, cocoamidopropylhyrdoxy sultaine, and mixtures thereof.

The personal care, home care, health care and I&I care compositions comprising the staged core-shell polymer of the invention can be formulated at pH ranges from about 0.5 to about 12. The desired pH for the compositions of the present invention is obviously dependent upon the specific end product applications. Generally, personal care applications have a desired pH range of about 3 to about 7.5 in one aspect, and from about 3.5 to about 6 in another aspect. Surprisingly, the staged core-shell/surfactant compositions of the invention when formulated at low pH values give a clear formulation while maintaining desirable rheology properties (e.g., viscosity and yield values). In another aspect, the staged core-shell polymer/surfactant compositions of the invention when formulated at pH values of about 6 and below give a clear formulation while maintaining desirable rheology properties of the compositions in which they are included. In still another aspect, the staged core-shell/surfactant compositions of the invention when formulated at pH values of about 5.0 and below give a clear formulation while maintaining desirable rheology properties of the compositions in which they are included. In a further aspect, the staged core-shell/surfactant compositions of the invention when formulated at pH values of from about 3.5 to about 4.5 give a clear formulation while maintaining desirable rheology properties of the compositions in which they are included.

Generally, home care applications have a desired pH range of about 1 to about 12 in one aspect, and from about 3 to about 10 in another aspect, depending on the desired end-use application.

The pH of the compositions of the present invention can be adjusted with any combination of acidic and/or basic pH adjusting agents known to the art. The staged core-shell polymeric rheology modifiers of the present invention are generally supplied in their acidic form. These polymers modify the rheology of a formulation through the neutralization of the carboxyl groups on the polymer with an alkaline material. Without wishing to be bound by theory, this causes ionic repulsion between like charged moieties along the backbone of the polymer and a three dimensional expansion of the polymer network, resulting in an increase in viscosity and other rheological properties. This is phenomenon is referred to in the literature as a "space filling" mechanism as compared to an associative thickening mechanism of the HASE polymers.

In one embodiment, compositions comprising the staged core-shell polymers of the invention can be acidified (pH reduction) without neutralizing the polymer. In another embodiment, compositions comprising the staged core-shell polymer can be neutralized with an alkaline material. In a further embodiment, compositions comprising the core-shell polymer can be neutralized subsequent to being acidified. In a still further embodiment, compositions comprising the staged core-shell polymers can be acidified subsequent to neutralization.

An alkaline material is incorporated to neutralize the polymer and can be referred to as a neutralizing agent or pH adjusting agent. Many types of neutralizing agents can be used in the present invention, including inorganic and organic bases, and combinations thereof. Examples of inorganic bases include but are not limited to the alkali metal hydroxides (especially sodium, potassium, and ammonium), and alkali metal salts of inorganic acids, such as sodium borate (borax), sodium phosphate, sodium pyrophosphate, and the like; and mixtures thereof. Examples of organic bases include but are not limited to triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, tromethamine(2-amino 2-hydroxymethyl-1,3-propanediol), and PEG-15 cocamine. Alternatively, other alkaline materials can be used alone or in combination with the above mentioned inorganic and organic bases. Such materials include surfactants, surfactant mixtures, pre-neutralized surfactants or materials that when combined in a composition containing the staged core-shell polymer of the invention is capable of neutralizing or partially neutralizing the carboxyl groups on the staged core-shell polymer backbone. Any material capable of increasing the pH of the composition is suitable.

Various acidic materials can be utilized as a pH adjusting agent in the present invention. Such acidic materials include organic acids and inorganic acids, for example, acetic acid, citric acid, tartaric acid, alpha-hydroxy acids, beta-hydroxy acids, salicylic acid, lactic acid, glycolic acid, and natural fruit acids, or inorganic acids, for example, hydrochloric acid, nitric acid, sulfuric acid, sulfamic acid, phosphoric acid, and combinations thereof. As discussed above, the addition of the acidic pH adjusting agent can be incorporated before or after the addition of the basic pH adjusting agent in a desired composition. The addition of the acidic material after the addition of the alkaline neutralizing agents yields significantly improved rheological properties. This is discussed in greater detail under the "back acid" formulation technique below.

As with the alkaline pH adjusting agents, other acidic materials can be used alone or in combination with the above mentioned inorganic and organic acids. Such materials include materials which when combined in a composition containing the staged core-shell polymer of the invention are capable of reducing the pH of the composition. It will be recognized by the skilled artisan that the acidic pH adjusting agents can serve more than one function. For example, acidic preservative compounds and acid based cosmeceutical compounds (e.g., alpha- and beta-hydroxy acids) not only serve their primary preservative and cosmeceutical functions, respectively, they can also be utilized to reduce or maintain the pH of a desired formulation.

Buffering agents can be used in the compositions of the invention. Suitable buffering agents include, but are not limited to, alkali or alkali earth metal carbonates, phosphates, bicarbonates, citrates, borates, acetates, acid anhydrides, succinates, and the like, such as sodium phosphate, sodium citrate, sodium acetate, sodium bicarbonate, and sodium carbonate.

The pH adjusting agent and/or buffering agent is utilized in any amount necessary to obtain and/or maintain a desired pH value in the composition.

Back Acid Formulation

The polymeric rheology modifiers of the present invention do not start to build substantial viscosity until a pH of about 5 or 6 is achieved. There are some Home and Personal Care applications, however, that require a pH of less than 6 for optimal and desired performance. This has limited the use of such polymers in such compositions. Additionally, it is difficult to even formulate stable applications at this lower pH range.

It has been found that if these compositions are raised to a near neutral or even alkaline pH and then subsequently reduced in pH, the viscosity and yield value generally remain unchanged or often actually increase. This formulating technique will be herein referred to as "Back Acid" thickening or "Back Acid Addition". This formulating technique broadens the scope of application of the present polymers and now allows for formulation in the acidic pH regime. Additionally, the process of "Back Acid" thickening can also be used to further increase the viscosity and stability of compositions formulated in the slightly acidic and in the alkaline pH regime.

The one or more staged core-shell polymers of the invention can be formulated into a desired composition in any order during the formulation procedure. An alkaline material is added and mixed to increase the pH of the composition to at least about 5 in one aspect, to at least about 6 in another aspect, and most to at least about 6.5 in a further aspect. The alkaline material can be any compound that can neutralize the staged core-shell polymer to a specified pH. In one aspect, the alkaline material is selected from any of the alkaline pH adjusting agents described above, such as, for example, sodium hydroxide, potassium hydroxide, triethanolamine, or another fatty acid amine neutralizing agent commonly used in said applications. Alternatively, other alkaline materials can be used, such as surfactants. In one aspect, the pH can be adjusted to at least about 0.5, 1, 1.5 or 2 pH units above the final target pH of the composition. In another aspect, the pH can be adjusted to at least 3, 4, or even 5 pH units above the final target pH of the composition. Subsequent to the pH adjustment with the alkaline material, an acidic material is added to reduce the pH of the composition to the desired target pH for the composition. In one aspect of the invention, the target pH ranges from about 3.5 to about 6, from about 4 to about 5.5 in another aspect, and from about 4.5 to 5 in a further aspect.

The material used to decrease the pH of the composition can be any acidic material. In one aspect, the acidic material is selected from any of the acidic pH adjusting agents described above, such as, for example, an organic acid, such as citric acid, acetic acid, alpha-hydroxy acid, beta-hydroxy acid, salicylic acid, lactic acid, glycolic acid, natural fruit acids, or combinations thereof. In addition, inorganic acids, for example, hydrochloric acid, nitric acid, sulfuric acid, sulfamic acid, phosphoric acid, and combinations thereof can be utilized. Mixtures of organic acids and inorganic acids are also contemplated.

The staged core-shell polymer of the present invention can be formulated with or without at least one surfactant. Such compositions can comprise any combination of optional additives, adjuvants, and benefit agents suitable for a desired personal care, home care, health care, and institutional and industrial care product known in the art. The choice and amount of each optional component employed will vary with the purpose and character of the end product, and can be readily determined by one skilled in the formulation art and from the literature. It is recognized that various additive, adjuvant, and benefit agents and components set forth herein can serve more than one function in a composition, such as, for example, surfactants, emulsifiers, solubilizers, conditioners, emollients, humectants, lubricants, pH adjusting agents, and acid based preservatives.

While overlapping weight ranges for the various components and ingredients that can be contained in the compositions of the invention have been expressed for selected embodiments and aspects of the invention, it should be readily apparent that the specific amount of each component in the disclosed personal care, home care, health care, and I&I care compositions will be selected from its disclosed range such that the amount of each component is adjusted such that the sum of all components in the composition will total 100 weight percent The amounts employed will vary with the purpose and character of the desired product and can be readily determined by one skilled in the formulation art and from the literature.

Optional additives and adjuvants include, but are not limited to insoluble materials, pharmaceutical and cosmeceutical actives, chelators, conditioners, diluents, solvents, fragrances, humectants, lubricants, solubilizers, emollients, opacifiers, colorants, anti-dandruff agents, preservatives, spreading aids, emulsifiers, sunscreens, fixative polymers, botanicals, viscosity modifiers, and the like, as well as the numerous other optional components for enhancing and maintaining the properties of a desired personal care, home care, health care, and I&I care composition.

Insoluble Material

The materials or compounds which require stabilization and/or suspension can be soluble or insoluble in water. Such compounds include insoluble silicones, silicone gums and resins, volatile and nonvolatile silicone oils, natural and synthetic waxes and oils and fatty acids, pearlescent materials, particulates, and other types of compounds and/or components set forth hereinbelow.

Silicones

In one aspect, silicones are utilized as conditioning agents which are commonly used in rinse off hair conditioner products and in shampoo products, such as the so-called "two-in-one" combination cleansing/conditioning shampoos. In one aspect, the conditioning agent is an insoluble silicone conditioning agent. Typically, the conditioning agent will be mixed in the shampoo composition to form a separate, discontinuous phase of dispersed, insoluble particles (also referred to as droplets). The silicone hair conditioning agent phase can be a silicone fluid and can also comprise other ingredients, such as a silicone resin, to improve silicone fluid deposition efficiency or enhance the glossiness of the hair especially when high refractive index (e.g., above about 1.6) silicone conditioning agents are used. The optional silicone hair conditioning agent phase may comprise volatile silicone, nonvolatile silicone, or combinations thereof. The silicone conditioning agent particles may comprise volatile silicone, non-volatile silicone, or combinations thereof. In one aspect, non-volatile silicone conditioning agents are utilized. If volatile silicones are present, they will typically be incidental to their use as a solvent or carrier for commercially available forms of non-volatile silicone materials ingredients, such as silicone gums and resins. The silicone hair conditioning agents for use in the present invention have a viscosity of from about 0.5 to about 50,000,000 centistokes (1 centistokes equals $1\times10^{-6}$ $m^2/s$) in one aspect, from about 10 to about 30,000,000 centistokes in another aspect, from about 100 to about 2,000,000 in a further aspect, and from about 1,000 to about 1,500,000 centistokes in a still further aspect, as measured at 25° C.

In one embodiment, the silicone conditioning agent particles can have a volume average particle diameter ranging from about 0.01 μm to about 500 μm. For small particle application to hair, the volume average particle diameters range from about 0.01 μm to about 4 μm in one aspect, from about 0.01 μm to about 2 μm in another aspect, and from about 0.01 μm to about 0.5 μm in still another aspect. For larger particle application to hair, the volume average particle diameters typically range from about 5 μm to about 125 μm in one aspect, from about 10 μm to about 90 μm in another aspect, from about 15 μm to about 70 μm in still another aspect, and from about 20 μm to about 50 μm in a further aspect.

Background material on silicones including sections discussing silicone fluids, gums, and resins, as well as manufacture of silicones, are found in Encyclopedia of Polymer Science and Engineering, vol. 15, 2d ed., pp 204-308, John Wiley & Sons, Inc. (1989), incorporated herein by reference. Silicone fluids are generally described as alkylsiloxane polymers. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference.

Silicone oils include polyalkyl, polyaryl siloxanes, or polyalkylaryl siloxanes which conform to the following formula:

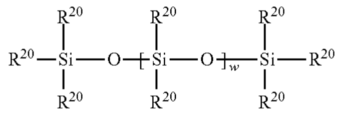

wherein $R^{20}$ is an aliphatic group, independently selected from alkyl, alkenyl, and aryl, $R^{20}$ can be substituted or unsubstituted, and w is an integer from 1 to about 8,000. Suitable unsubstituted $R^{20}$ groups for use in the present invention include, but are not limited to alkoxy, aryloxy, alkaryl, arylalkyl, arylalkenyl, alkamino, and ether-substituted, hydroxyl-substituted, and halogen-substituted aliphatic and aryl groups. Suitable $R^{20}$ groups also include amines, cationic amines and quaternary ammonium groups.

In one aspect of the invention, exemplary $R^{20}$ alkyl and alkenyl substituents include $C_1$-$C_5$ alkyl and $C_1$-$C_5$ alkenyl groups. In another aspect, $R^{20}$ is methyl. The aliphatic portions of other alkyl- and alkenyl-containing groups (such as alkoxy, alkaryl, and alkamino) can be straight or branched chains, and contain from $C_1$-$C_5$ in one aspect, from $C_1$-$C_4$ in another aspect, and from $C_1$-$C_2$ in a further aspect. As discussed above, the $R^{20}$ substituents can also contain amino functionalities (e.g., alkamino groups), which can be primary, secondary or tertiary amines or quaternary ammonium. These include mono-, di- and tri-alkylamino and alkoxyamino groups, wherein the aliphatic portion chain length is as described above. Exemplary aryl groups in the foregoing embodiments include phenyl and benzyl.

Exemplary siloxanes are polydimethyl siloxane, polydiethylsiloxane, and polymethylphenylsiloxane. These siloxanes are available, for example, from Momentive Performance Materials in their Viscasil R and SF 96 series, and from Dow Corning marketed under the Dow Corning 200 series. Exemplary polyalkylaryl siloxane fluids that may be used, include, for example, polymethylphenylsiloxanes. These siloxanes are available, for example, from Momentive Performance Materials as SF 1075 methyl phenyl fluid or from Dow Corning as 556 Cosmetic Grade Fluid, or from Wacker Chemical Corporation, Adrian, Mich., under the trade name Wacker-Belsil® PDM series of phenyl modified silicones (e.g., PDM 20, PDM 350 and PDM 1000).

Cationic silicone fluids are also suitable for use with the compositions of the invention. The cationic silicone fluids can be represented, but are not limited, to the general formula):

$$(R^{21})_e G_{3-f}\text{-Si—}(OSiG_2)_g\text{-}(OSiG_f(R_1)_{(2-f)})_h\text{—O—}SiG_{3-e}(R^{21})_f$$

wherein G is hydrogen, phenyl, hydroxy, or $C_1$-$C_8$ alkyl (e.g., methyl or phenyl); e is 0 or an integer having of from 1 to 3; f is 0 or 1; g is a number from 0 to 1,999; h is an integer from 1 to 2,000 in one aspect, and from 1 to 10 in another aspect; the sum of g and h is a number from 1 to 2,000 in one aspect, and from 50 to 500 in another aspect of the invention; $R^{21}$ is a monovalent radical conforming to the general formula $C_qH_{2q}L$, wherein q is an integer having a value from 2 to 8 and L is selected from the following groups:

a) $—N(R^{22})CH_2CH_2N(R^{22})_2$ b) $—N(R^{22})_2$ c) $—N^+(R^{22})_3CA^-$ d) $—N(R^{22})CH_2CH_2N^+H_2R^{22}CA^-$ wherein $R^{22}$ is independently selected from hydrogen, $C_1$-$C_{20}$ alkyl, phenyl, benzyl; and $CA^-$ is a halide counter ion selected from chloride, bromide, fluoride, and iodide.

In another aspect, a cationic silicone useful in the staged core-shell compositions of the invention can be represented by the formula:

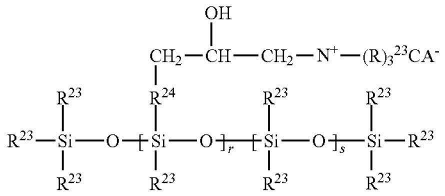

wherein $R^{23}$ represents a radical selected from a $C_1$-$C_{18}$ alkyl and $C_1$-$C_m$ alkenyl group; $R^{24}$ independently represents a radical selected from a $C_1$-$C_{18}$ alkylene radical or a $C_1$-$C_{18}$ alkyleneoxy radical; CA is a halide ion; r represents an integer ranging from 2 to 20 in one aspect, and from 2 to 8 in another aspect; s represents an integer ranging from 20 to 200 in one aspect, and from 20 to 50 in another aspect. In one aspect, $R^{23}$ is methyl. In another aspect, Q is a chloride ion. An example of a quaternary silicone polymer useful in the present invention is Abil® T Quat 60, available from Evonik Goldschmidt Corporation, Hopewell, Va.

Another class of suitable silicone fluids is the insoluble silicone gums. These gums are polysiloxane materials having a viscosity at 25° C. of greater than or equal to 1,000,000 centistokes. Silicone gums are described in U.S. Pat. No. 4,152,416; Noll and Walter, Chemistry and Technology of Silicones, New York: Academic Press 1968; and in General Electric Silicone Rubber Product Data Sheets SE 30, SE 33, SE 54, and SE 76, all of which are incorporated herein by reference. The silicone gums typically have a mass molecule weight in excess of about 200,000 daltons, generally between about 200,000 to about 1,000,000 daltons, specific examples of which include polydimethylsiloxane, polydimethylsiloxane/methylvinylsiloxane copolymer, polydimethylsiloxane/diphenyl siloxane/methylvinylsiloxane) copolymer, and mixtures thereof.

Another category of nonvolatile, insoluble silicone fluid conditioning agents are the high refractive index polysiloxanes, having a refractive index of at least about 1.46 in one aspect, at least about 1.48 in another aspect, at least about 1.52 in a further aspect, and at least about 1.55 in a still further aspect. The refractive index of the polysiloxane fluid will generally be less than about 1.70, typically less than about 1.60. In this context, polysiloxane "fluid" includes oils, resins, and gums.

The high refractive index polysiloxane fluid includes those represented by the general formula set forth for the polyalkyl, polyaryl, and polyalkylaryl siloxanes described above, as well as cyclic polysiloxanes (cyclomethicones) represented by the formula:

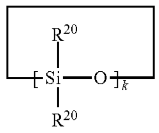

wherein the substituent $R^{20}$ is as defined above, and the number of repeat units, k, ranges from about 3 to about 7 in one aspect, and from 3 to 5 in another aspect. The high refractive index polysiloxane fluids can contain an amount of aryl containing $R^{20}$ substituents sufficient to increase the refractive index to a desired level, which is described above. Additionally, $R^{20}$ and k must be selected so that the material is non-volatile. Aryl containing substituents include those which contain alicyclic and heterocyclic five and six member aryl rings and those which contain fused five or six member rings. The aryl rings can be substituted or unsubstituted. Substituents include aliphatic substituents, and can also include alkoxy substituents, acyl substituents, ketones, halogens (e.g., Cl and Br), amines, etc. Exemplary aryl containing groups include substituted and unsubstituted arenes, such as phenyl, and phenyl derivatives such as phenyls with $C_1$-$C_5$ alkyl or alkenyl substituents, e.g., allylphenyl, methyl phenyl and ethyl phenyl, vinyl phenyls such as styrenyl, and phenyl alkynes (e.g., phenyl $C_2$-$C_4$ alkynes). Heterocyclic aryl groups include substituents derived from furan, imidazole, pyrrole, pyridine, etc. Fused aryl ring substituents include, for example, naphthalene, coumarin, and purine.

The high refractive index polysiloxane fluids can have a degree of aryl containing substituents of at least about 15% by weight in one aspect, at least about 20% by weight in another aspect, at least about 25% by weight in a further aspect, at least about 35% by weight in still further aspect, and at least about 50% by weight in an additional aspect, based on the weight of the polysiloxane fluid. Typically, the degree of aryl substitution will be less than about 90% by weight, more typically less than about 85% by weight, and can generally range from about 55% to about 80% by weight of the polysiloxane fluid.

In another aspect, the high refractive index polysiloxane fluids have a combination of phenyl or substituted phenyl derivatives. The substituents can be selected from $C_1$-$C_4$ alkyl (e.g., methyl), hydroxy, and $C_1$-$C_4$ alkylamino.

When high refractive index silicones (silicone resins, silicone waxes, and phenyl modified silicones) are used in the compositions of the present invention, they optionally can be used in solution with a spreading agent, such as a silicone resin or a suitable surfactant, to reduce the surface tension by a sufficient amount to enhance spreading and thereby augment the glossiness (subsequent to drying) of hair treated with such compositions. Silicone fluids suitable for use in the compositions of the present invention are disclosed in U.S. Pat. Nos. 2,826,551; 3,964,500; 4,364,837, and British Patent No. 849,433, all of which are incorporated herein by reference. High refractive index polysiloxanes and polyaryl siloxanes (trimethyl pentaphenyl trisiloxane, available under the trade name DC PH-1555 HRI) are offered from Dow Corning Corporation (Midland, Mich.), Huls America (Piscataway, N.J.), and Momentive Performance Materials Inc. (Albany, N.Y.). Examples of silicone waxes include SF 1632 (INCI Name: Ceteryl Methicone) and SF1642 (INCI Name: C30-45 Alkyl Dimethicone), also available from Momentive Performance Materials, Inc.

Silicone resins and resin gels can be included as a silicone conditioning agent suitable for use in the compositions of the present invention. These resins are crosslinked polysiloxanes. The crosslinking is introduced through the incorporation of trifunctional and tetra-functional silanes with monofunctional and/or difunctional silanes during manufacture of the silicone resin.

As is well understood in the art, the degree of crosslinking that is required in order to result in a silicone resin will vary according to the specific silane units incorporated into the silicone resin. In general, silicone materials which have a sufficient level of trifunctional and tetra-functional siloxane monomer units (and hence, a sufficient level of crosslinking) such that they form a rigid or hard film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. In one aspect, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and terachlorosilane, with the methyl-substituted silanes being most commonly utilized. In one aspect, suitable silicone resins are SS4230 (INCI Name: Cyclopetasiloxane (and) Trimethylsiloxysilicate) and SS4267 (INCI Name: Dimethicone (and) Trimethylsiloxysilicate) available from Momentive Performance Materials, Inc. Suitable silicone resin gels include RG100 (INCI Name: Cyclopetasiloxane (and) Dimethicone/vinyltrimethylsiloxysilicate crosspolymer) from Wacker Chemical Corporation.

Silicone materials and silicone resins can be identified according to a shorthand nomenclature system known to those of ordinary skill in the art as "MDTQ" nomenclature. Under this naming system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence. Typical alternate substituents include groups such as vinyl, phenyls, amines, hydroxyls, etc. The molar ratios of the various units, either in terms of subscripts to the symbol indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

Exemplary silicone resins for use in the compositions of the present invention include, but are not limited to MQ, MT, MTQ, MDT and MDTQ resins. In one aspect, methyl is the silicone resin substituent. In another aspect, the silicone resin is selected from a MQ resins, wherein the M:Q ratio is from about 0.5:1.0 to about 1.5:1.0 and the average molecular weight of the silicone resin is from about 1000 to about 10,000 daltons.

When employed with non-volatile silicone fluids having a refractive index below 1.46, the weight ratio of the non-volatile silicone fluid to the silicone resin component, ranges from about 4:1 to about 400:1 in one aspect, from about 9:1 to about 200:1 in another aspect, from about 19:1 to about 100:1 in a further aspect, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e., the conditioning active, the sum of the fluid and resin should be included in determining the level of silicone conditioning agent in the composition.

The volatile silicones described above include cyclic and linear polydimethylsiloxanes, and the like. As described previously in the formula for cyclic polysiloxanes (cyclomethicones), they typically contain about 3 to about 7 silicon atoms, alternating with oxygen atoms, in a cyclic ring structure. However, each $R^{20}$ substituent and repeating unit, k, in the formula is selected so that the compound is non-volatile. Typically, the $R^{20}$ substituent is substituted with two alkyl groups (e.g., methyl groups). The linear volatile silicones are silicone fluids, as described above, having viscosities of not more than about 25 mPa·s. "Volatile" means that the silicone has a measurable vapor pressure, or a vapor pressure of at least 2 mm of Hg at 20° C. Non-volatile silicones have a vapor pressure of less than 2 mm Hg at 20° C. A description of cyclic and linear volatile silicones is found in Todd and Byers, "Volatile Silicone Fluids for Cosmetics", Cosmetics and Toiletries, Vol. 91(1), pp. 27-32 (1976), and in Kasprzak, "Volatile Silicones", Soap/Cosmetics/Chemical Specialities, pp. 40-43 (December 1986), each incorporated herein by reference.

Exemplary volatile cyclomethicones are D4 cyclomethicone (octamethylcyclotetrasiloxane), D5 cyclomethicone (decamethylcyclopentasiloxane), D6 cyclomethicone (dodecamethylcyclohexasiloxane), and blends thereof (e.g., D4/D5 and D5/D6). Volatile cyclomethicones and cyclomethicone blends are commercially available from Momentive Performance Materials Inc as SF1202, SF 1214, SF1256, and SF1258, Dow Corning, Midland, Mich. under the Xiameter® cyclomethicone fluid product designations PMX-0244, PMX-245, PMX-246, PMX-345, and Dow Corning® 1401 fluid. Blends of volatile cyclomethicones and volatile linear dimethicones are also contemplated within the scope of the invention.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning as Xiameter® PMX-200 silicone fluids (e.g., product designations 0.65 CS, 1 CS, 1.5 CS, and 2 CS) and Xiameter® PMX 2-1184 silicone fluid.

Emulsified silicones are also suitable for use in the compositions of the invention. In one aspect, suitable emulsified silicones are emulsions of dimethicone with at least one emulsifier selected from nonionic, anionic, amphoteric, cationic surfactant, and/or cationic polymer and mixtures thereof. In one aspect, useful silicone emulsions have an average silicone particle size in the composition of less than 30 μm, less than 20 μm in another aspect, and less than 10 μm in a further aspect. In another aspect of the invention, the average silicone particle size of the emulsified silicone in the composition is less than 2 μm, and in another it ranges from 0.01 to 1 μm. Silicone emulsions having an average silicone particle size of <0.15 μm are generally termed micro-emulsions. Particle size may be measured by means of a laser light scattering technique, using a 2600D Particle Sizer from Malvern Instruments. Suitable silicone emulsions for use in the invention are also commercially available in a pre-emulsified form. Examples of suitable pre-formed commercially available emulsions include Dow Corning® emulsions MEM-1664, 2-1352, MEM-1764, MEM-1784, HMW 2220, 2-1865, MEM-1310, MEM-1491, and 5-7137. These are emulsions/microemulsions of dimethiconol. Preformed emulsions of amino functional silicone are also available from suppliers of silicone oils such as Dow Corning (CE-8170, 5-7113, 2-8194, 949, and CE 8401) and Momentive Performance Materials. Particularly suitable are emulsions of amino functional silicone oils with non ionic and/or cationic surfactant. Examples include Dow Corning® 939 cationic emulsion, 949 cationic emulsion, 2-8194 cationic microemulsion, and 2-8299 cationic emulsion, and 2-8177 nonionic emulsion; as well as SM2115 and SME253, nonionic microemulsions supplied by Momentive Performance Materials. Mixtures of any of the above types of silicone may also be used. Other examples of amino functional silicones are the aminosilicone oils. Suitable commercially available aminosilicone oils include Dow Corning® Q2-8166, Q2-8220, and 2-8566; and SF 1708, (Momentive Performance Materials).

Other suitable silicone oils include the dimethicone copolyols, which are linear or branched copolymers of dimethylsiloxane (dimethicone) modified with alkylene oxide units. The alkylene oxide units can be arranged as random or block copolymers. A generally useful class of dimethicone polyols are block copolymers having terminal and/or pendent blocks of polydimethylsiloxane and blocks of polyalkylene oxide, such as blocks of polyethylene oxide, polypropylene oxide, or both. Dimethicone copolyols can be water soluble or insoluble depending on the amount of polyalkylene oxide present in the dimethicone polymer and can be anionic, cationic, or nonionic in character.

Water soluble or water dispersible silicones can also be used in the compositions of the invention. Such water soluble silicones contain suitable anionic functionality, cationic functionality, and/or nonionic functionality to render the silicone water soluble or water dispersible. In one aspect, the water soluble silicones contain a polysiloxane main chain to which is grafted at least one anionic moiety. The anionic moiety can be grafted to a terminal end of the polysiloxane backbone, or be grafted as a pendant side group, or both. By anionic group is meant any hydrocarbon moiety that contains at least one anionic group or at least one group that can be ionized to an anionic group following neutralization by a base. As discussed previously, the quantity of the hydrocarbon groups of anionic character which are grafted onto the silicone chain are chosen so that the corresponding silicone derivative is water-soluble or water-dispersible after neutralization of the ionizable groups with a base. The anionic silicone derivatives can be selected from existing commercial products or can be synthesized by any means known in the art. The nonionic silicones contain alkylene oxide terminal and/or pendant side chain units (e.g., the dimethicone copolyols discussed above). Another example of nonionic silicones is the silicone polyglucosides from Wacker (e.g., Wacker-Belsil® SPG 128 VP, SPG 130 VP, and VSR 100 VP).

Silicones with anionic groups can be synthesized by reaction between (i) a polysiloxane containing a silinic hydrogen and (ii) a compound containing olefinic unsaturation that also contains an anionic functional group. Exemplary of such a reaction is the hydrosilylation reaction between poly(dimethylsiloxanes) containing a Si—H group(s) and an olefin, $CH_2$═$CHR^{27}$, wherein $R^{27}$ represents a moiety containing an anionic group. The olefin can be monomeric, oligomeric or polymeric. Polysiloxane compounds that contain a pendant reactive thio (—SH) group(s) are also suitable for grafting an unsaturated anionic group containing compound to the poly (siloxane) backbone.

According to one aspect of the present invention, the anionic monomers containing ethylenic unsaturation are used alone or in combination and are selected from linear or branched, unsaturated carboxylic acids. Exemplary unsaturated carboxylic acids are acrylic acid, methacrylic acid, maleic acid, maleic anhydride, itaconic acid, fumaric acid and crotonic acid. The monomers can optionally be partially or completely neutralized by base to form an alkali, alkaline earth metal, and ammonium salt. Suitable bases include but are not limited to the alkali, alkaline earth (e.g., sodium, potassium, lithium, magnesium, calcium) and ammonium hydroxides. It will be noted that, similarly, the oligomeric and polymeric graft segments formed from the forgoing monomers can be post-neutralized with a base (sodium hydroxide, aqueous ammonia, etc.) to form a salt. Examples of such silicone derivatives which are suitable for use in the present invention are described in European Patent Application No. EP 0 582 152 and International Patent Application Publication No. WO 93/23009. An exemplary class of silicone polymers are the polysiloxanes containing repeat units represented by the following structure:

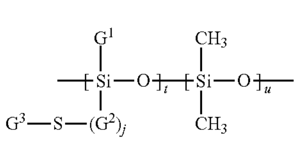

wherein $G^1$ represents hydrogen, $C_1$-$C_{10}$ alkyl and phenyl radical; $G^2$ represents $C_1$-$C_{10}$ alkylene; $G^3$ represents an anionic polymeric residue obtained from the polymerization of at least one anionic monomer containing ethylenic unsaturation; j is 0 or 1; t is an integer ranging from 1 to 50; and u is an integer from 10 to 350. In one embodiment of the invention, $G^1$ is methyl; j is 1; and $G_2$ is propylene radical; $G^3$ represents a polymeric radical obtained from the polymerization of at least one unsaturated monomer containing a carboxylic acid group (e.g., acrylic acid, methacrylic acid, itaconic acid, fumaric acid, crotonic acid, maleic acid, or aconitic acid, and the like).

In one aspect, the carboxylate group content in the final polymer ranges from 1 mole of carboxylate per 200 g of polymer to 1 mole of carboxylate per 5000 g of polymer. In one aspect, the number average molecular weight of the silicone polymer ranges from about 10,000 to about 1,000,000 daltons, and from 10,000 to 100,000 daltons in another aspect. Exemplary unsaturated monomers containing carboxylic acid groups are acrylic acid and methacrylic acid. In addition, to the carboxylic acid group containing monomers, $C_1$-$C_{20}$ alkyl esters of acrylic acid and methacrylic acid can be copolymerized into the polymeric backbone. Exemplary esters include but are not limited to the ethyl and butyl esters of acrylic and methacrylic acid. A commercially available silicone-acrylate polymer is marketed by the 3M Company under the trademark Silicones "Plus" Polymer 9857C (VS80 Dry). These polymers contain a polydimethylsiloxane (PDMS) backbone onto which is grafted (through a thiopropylene group) random repeating units of poly(meth)acrylic acid and the butyl ester of poly(meth)acrylate. These products can be obtained conventionally by radical copolymerization between thiopropyl functionalized polydimethylsiloxane and a mixture of monomers comprising (meth)acrylic acid and of butyl(meth)acrylate.

In another aspect, the water soluble silicone copolyol useful in the practice of the present invention are silicone copolyol carboxylates represented by the formula:

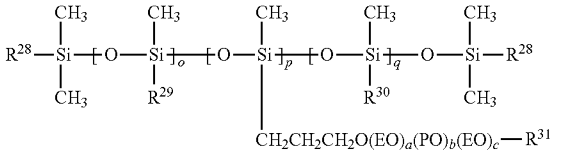

wherein $R^{28}$ and $R^{29}$ are independently selected from $C_1$-$C_{30}$ alkyl, $C_6$-$C_{14}$ aryl, $C_7$-$C_{15}$ aralkyl, $C_1$-$C_{15}$ alkaryl, or an alkenyl group of 1 to 40 carbons, hydroxyl, —$R^{32}$-G' or —$(CH_2)_3$ $O(EO)_a(PO)_b(EO)_c$-G', with the proviso that both $R^{28}$ and $R^{29}$ are not methyl; $R^{30}$ is selected from $C_1$-$C_5$ alkyl or phenyl; in this formula a, b, and c are integers independently ranging from 0 to 100; EO is ethylene oxide, —$(CH_2CH_2O)$—; PO is propylene oxide, —$(CH_2CH(CH_3)O)$—; in this formula o is an integer ranging from 1 to 200, p is an integer ranging from 0 to 200, and q is an integer ranging from 0 to 1000; $R^{31}$ is hydrogen, $C_1$-$C_{30}$ alkyl, aryl, $C_7$-$C_{15}$ aralkyl, $C_7$-$C_{15}$ alkaryl, or alkenyl group of 1 to 40 carbons or —C(O)—X wherein X is $C_1$-$C_{30}$ alkyl, $C_6$-$C_{14}$ aryl, $C_7$-$C_{15}$ aralkyl, $C_1$-$C_{15}$alkaryl, or an alkenyl group of 1 to 40 carbons, or a mixture thereof; $R^{32}$ is a divalent group selected from alkylene radical of 1 to 40 carbon atoms which may be interrupted with arylene group of 6 to 18 carbons or an alkylene group containing unsaturation of 2 to 8 carbons; and G' is independently selected from a moiety represented by the formula:

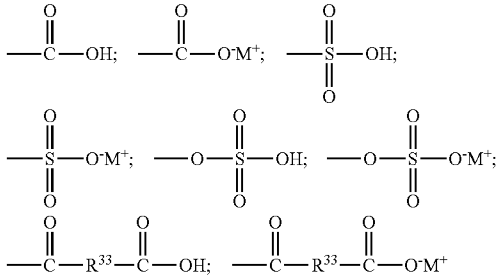

wherein $R^{33}$ is a divalent group selected from alkylene of 1 to 40 carbons, an unsaturated group containing 2 to 5 carbon atoms, or an arylene group of 6 to 12 carbon atoms; where M is a cation selected from Na, K, $L_1$, $NH_4$, or an amine containing at least one $C_1$-$C_{10}$ alkyl, $C_6$-$C_{14}$ aryl (e.g., phenyl, naphthyl), $C_2$-$C_{10}$ alkenyl, $C_1$-$C_{10}$ hydroxyalkyl, $C_7$-$C_{24}$ arylalkyl or $C_7$-$C_{24}$ alkaryl groups. Representative $R^{33}$ radicals are: —$CH_2CH_2$—, —CH═CH—, —CH═$CHCH_2$—, and phenylene.

In another embodiment, the water soluble silicones useful in the practice of the present invention can be represented an anionic silicone copolyol represented by the formula:

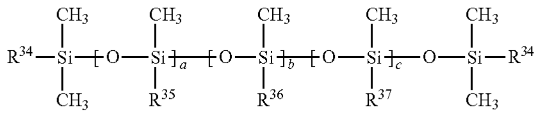

wherein is $R^{34}$ is methyl or hydroxyl; $R^{35}$ is selected from $C_1$-$C_8$ alkyl or phenyl; $R^{36}$ represents the radical —$(CH_2)_3O(EO)_x(PO)_y(EO)_z$—$SO_3^-M^+$; where M is a cation selected from Na, K, Li, or $NH_4$; in this formula x, y and z are integers independently ranging from 0 to 100; $R^{37}$ represents the radical —$(CH_2)_3O(EO)_x(PO)_y(EO)_z$—H; in this formula a and c independently represent integers ranging from 0 to 50, and b is an integer ranging from 1 to 50; EO is ethylene oxide, e.g., —$(CH_2CH_2O)$—; PO is propylene oxide, e.g., —$(CH_2CH(CH_3)O)$—.

In still another embodiment, the water soluble silicones useful in the practice of the present invention can be represented an anionic silicone copolyol represented by the formula:

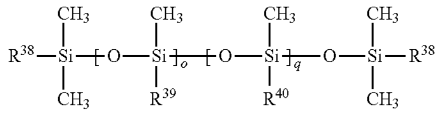

wherein $R^{38}$ and $R^{39}$ independently are —$CH_3$ or a radical represented by: —$(CH_2)_3O(EO)_a(PO)_b(EO)_c$—C(O)—$R^{41}$—C(O)OH, subject to the proviso that both $R^{38}$ and $R^{39}$ are not —$CH_3$ at the same time; $R^{41}$ is selected from the divalent radical —$CH_2CH_2$, —CH═CH—, and phenylene; $R^{40}$ is selected from $C_1$-$C_5$ alkyl or phenyl; in this formula a, b and c are integers independently ranging from 0 to 20; EO is an ethylene oxide residue, e.g., —$(CH_2CH_2O)$—; PO is a propylene oxide residue, e.g., —$(CH_2CH(CH_3)O)$—; in this formula o is an integer ranging from 1 to 200 and q is an integer ranging from 0 to 500.

Other water soluble silicones useful in the invention are quaternized silicone copolyol polymers. These polymers have a pendant quaternary nitrogen functional group present and are represented by the formula:

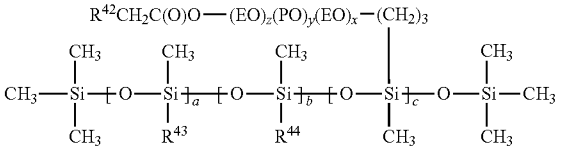

wherein $R^{42}$ represents a quaternary substituent —$N^+R^{45}R^{46}R^{47}CA^-$, wherein $R^{45}$ and $R^{46}$, and $R^{47}$, independently, are selected from hydrogen and linear and branched $C_1$-$C_{24}$ alkyl, and $CA^-$ represents an counter anion suitable to balance the cationic charge on the nitrogen atom; $R^{43}$ is selected from $C_1$-$C_{10}$ alkyl and phenyl; $R^{44}$ is —$(CH_2)_3O(EO))_x(PO)_y(EO)_z$—H, where EO is an ethylene oxide residue, e.g., —$(CH_2CH_2O)$—; PO is a propylene oxide residue, e.g., —$(CH_2CH(CH_3)O)$—; in this formula a is an integer from 0 to 200, b is an integer from 0 to 200, and c is an integer from 1 to 200; in this formula x, y and z are integers and are independently selected from 0 to 20. In one aspect, the counter anion $CA^-$ represents an anion selected from chloride, bromide, iodide, sulfate, methylsulfate, sulfonate, nitrate, phosphate, and acetate.

Other suitable water soluble silicones are amine substituted silicone copolyols represented by the formula:

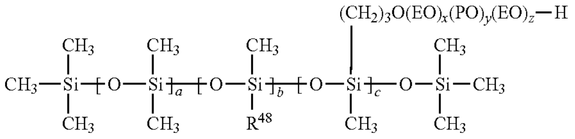

wherein $R^{48}$ is selected from —$NH(CH_2)_nNH_2$ or —$(CH_2)_nNH_2$; in this formula n is an integer from 2 to 6; and x, is n integer from 0 to 20; where EO is an ethylene oxide residue, e.g., —$(CH_2CH_2O)$—; PO is a propylene oxide residue, e.g., —$(CH_2CH(CH_3)O)$—; in this formula a is an integer from 0 to 200, b is an integer from 0 to 200, and c is an integer from 1 to 200; in this formula x, y and z are integers and are independently selected from 0 to 20.

Still other water soluble silicones can be selected from nonionic silicone copolyols (dimethicone copolyols) represented by the formula:

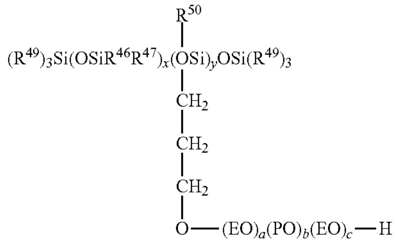

wherein $R^{49}$, independently, represents a radical selected from $C_1$-$C_{30}$ alkyl, $C_6$-$C_{14}$ aryl, and $C_2$-$C_{20}$ alkenyl; $R^{50}$ represents a radical selected from $C_1$-$C_{30}$ alkyl, $C_6$-$C_{14}$ aryl, and $C_2$-$C_{20}$ alkenyl; EO is an ethylene oxide residue, e.g., —$(CH_2CH_2O)$—; PO is a propylene oxide residue, e.g., —$(CH_2CH(CH_3)O)$—; in this formula a, b, and c are, independently, 0 to 100; in this formula x is 0 to 200; and y is 1 to 200.

In another embodiment, water soluble silicones can be selected from nonionic silicone copolyols represented by the formula:

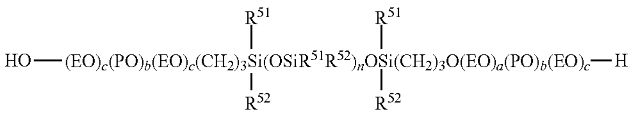

wherein $R^{51}$ and $R^{52}$, independently, represent a radical selected from $C_1$-$C_{30}$ alkyl, $C_6$-$C_{14}$ aryl, and $C_2$-$C_{20}$ alkenyl; EO is an ethylene oxide residue, e.g., —$(CH_2CH_2O)$—; PO is a propylene oxide residue, e.g., —$(CH_2CH(CH_3)O)$—; in this formula a, b, and c are independently 0 to 100; and in this formula n is 0 to 200.

In the formulas set forth above, the EO and PO residues can be arranged in random, in nonrandom, or in blocky sequences.

Water soluble silicones are disclosed in U.S. Pat. Nos. 5,136,063 and 5,180,843, the disclosures of which are incorporated herein by reference. Such silicones are commercially available under the Silsoft® and Silwet® trade names from Momentive Performance Materials. Specific product designations include, but are not limited to, Silsoft product designations 430, 440, 475, 805, 810, 840, 870, 875, 880, 895, 900, and 910; Silwet product designation L-7604. Other commercially available products include Dow Corning® 5103 and 5329; Abil® product designations B 88183, B 8843, Evonik Goldschmidt, and Silsense™ dimethicone copolyols, such as Silsense Copolyol-1 and Silsense Copolyol-7, available from Lubrizol Advanced Materials, Inc, Cleveland, Ohio.

The concentration of the silicone agents described above can range from about 0.01% to about 10%, by weight of the composition in which it is included. In another aspect, the amount of silicone agent ranges from about 0.1% to about 8%, from about 0.1% to about 5% in still another aspect, and from about 0.2% to about 3% by weight in a further aspect, all based on the total weight of the composition.

Natural and Synthetic Waxes, Oils, Fatty Acids and Alcohols

In one aspect, the natural and synthetic waxes, oils, fatty acids, fatty alcohols, as well as their derivatives are useful in the compositions of the present invention as a benefit agent, and can be useful, for example, as conditioners, emollients, and humectants for the hair and skin.

The natural and synthetic wax agents that can suitably be employed in the compositions of the invention, include, but are not limited to, carnauba wax, hydrolyzed carnauba wax, carnauba acid wax, ethoxylated carnauba wax (e.g., PEG-12 carnauba wax), candelila wax, hydrolyzed candelilla wax, hydrogenated castor wax, bayberry wax, alfa wax, paraffin wax, ozokerite wax, olive wax, ouricury wax, palm kernel wax, rice wax, hydrogenated jojoba wax, bees wax, modified bees wax, e.g., oxidized beeswax, ethoxylated beeswax (e.g., PEG-6 beeswax, PEG-8 beeswax, PEG-12 beeswax, PEG-20 beeswax), dimethicone copolyol beeswax esters and dimethiconol beeswax ester (e.g. Bis-Hydroxyethoxypropyl Dimethicone Beeswax Esters, Dimethicone PEG-8 Beeswax, and Dimethiconol Beeswax available from Lubrizol Advanced Materials, Inc. under the Ultrabee® trademark), cerabellina wax, marine waxes, lanolin and derivatives thereof, and polyolefin waxes, e.g., polyethylene wax; and mixtures thereof.

Lanolin and lanolin derivatives are selected from lanolin, lanolin wax, lanolin oil, lanolin alcohols, lanolin fatty acids, esters of lanolin fatty acids such as the isopropyl esters of lanolin fatty acid (e.g., isopropyl lanolates), alkoxylated lanolin, acetylated lanolin alcohols, and combinations thereof. Lanolin and lanolin derivatives are commercially available from Lubrizol Advanced Materials, Inc. under the trade names Lanolin LP 108 USP, Lanolin USP AAA, Acetulan™ Ceralan™, Lanocerin™, Lanogel™ (product designations 21 and 41), Lanogene™, Modulan™, Ohlan™, Solulan™ (product designations 16, 75, L-575, 98, and C-24), and Vilvanolin™ (product designations C, CAB, L-101, and P).

Suitable oily agents for use in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils typically contain about 12 to 19 carbon atoms. Branched chain hydrocarbon oils, including hydrocarbon polymers, typically will contain more than 19 carbon atoms. Specific non-limiting examples of these hydrocarbon oils include paraffin oil, mineral oil, petrolatums, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-octamethyl-10-methylundecane and 2,2,4,4,6,6-hexamethyl-8-methylnonane, available from Permethyl Corporation. Hydrocarbon polymers such as polybutene and polydecene are also useful.

Mineral oils and petrolatums include cosmetic, USP and NF grades and are commercially available from Penreco under the Drakeol® and Penreco® trade names. Mineral oil includes hexadecane and paraffin oil.

Liquid polyolefin oils can be used in the compositions of the present invention. The liquid polyolefin agents are typically poly-α-olefins that have been hydrogenated. Polyolefins for use herein can be prepared by the polymerization of $C_4$ to about $C_{14}$ olefinic monomers. Non-limiting examples of olefinic monomers for use in preparing the polyolefin liquids herein include ethylene, propylene, 1-butene, 1-pentene, 1-hexene, 1-octene, 1-decene, 1-dodecene, 1-tetradecene, and 1-hexadecene, branched isomers such as isobutylene, 4-methyl-1-pentene, and mixtures thereof. In one aspect, a suitable hydrogenated polyolefin is the copolymer of isobutylene and butene. A commercially available material of this type is Panalane® L-14E (INCI Name: Hydrogenated Polyisobutene) marketed by Lipo Chemicals Inc, Patterson, N.J.

Fluorinated and perfluorinated oils are also contemplated within the scope of the present invention. Fluorinated oils include perfluoropolyethers described in European Patent No. EP 0 486 135 and the fluorohydrocarbon compounds described in International Patent Application Publication No. WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers.

Natural oils that are useful in the practice of this invention include, but are not limited to, peanut, sesame, avocado, coconut, cocoa butter, canola, babassu, almond, corn, grape seed, cottonseed, sesame seed, walnut, castor, olive, jojoba, palm, palm kernel, soybean, wheat germ, linseed, safflower, shea nut, sunflower seed, eucalyptus, lavender, vetiver, litsea, cubeba, lemon, sandalwood, rosemary, chamomile, savory, nutmeg, cinnamon, hyssop, caraway, orange, geranium, cade, and bergamot oils, fish oils, as well as glycerides (mono- di- and triglycerides) derived from plant oils, vegetable oils, and animal fats (e.g., tallow and lard); and mixtures thereof.

Oils as benefit agents can be in the form of organogel particles (oil and wax) as described in U.S. Pat. No. 6,737,394.

Suitable glycerides (mono-, di-, and triglycerides) can be derived through the esterification of glycerol, a monoglyceride, or a diglyceride with a fatty acid(s) by techniques well known in the art, or by glycerolysis of animal fats and vegetable oils in the presence of a base at elevated temperature and under an inert atmosphere (See RSC Green Chemistry Book Series, The Royal Society of Chemistry, *The Future of Glycerol: New Uses Of A Versatile Material*, Chapter 7, Mario Pagliaro and Michele Rossi,© 2008). Fatty acids suitable for use in the esterification reaction include saturated and unsaturated $C_8$-$C_{30}$ fatty acids.

Also useful in the compositions of the present invention are the free fatty acids and their derivatives. Suitable fatty acids include saturated and unsaturated $C_8$ to $C_{30}$ fatty acids. Exemplary fatty acids include, but are not limited to, caprylic acid, capric acid, lauric acid, myristic acid, palmitic acid, palmitoleic acid, stearic acid, oleic acid, ricinoleic acid, vaccenic acid, linoleic acid, α-linolenic acid, γ-linolenic acid, arachidic acid, gadoleic acid, arachidonic acid, EPA (5,8,11, 14,17-eicosapentaenoic acid), behenic acid, erucic acid, DHA (4,7,10,13,16,19-docosahexaenoic acid), lignoceric acid, and mixtures thereof.

Alkoxylated fatty acids are also useful herein and can be formed by esterifying a fatty acid with an ethylene oxide and/or propylene oxide or with a pre-formed polymeric ether (e.g., polyethylene glycol or polypropylene glycol). The product is a polyethylene oxide ester, polypropylene oxide ester, or a polyethylene/polypropylene oxide ester of the respective fatty acid. In one aspect, an ethoxylated fatty acid can be represented by the formula: R'—C(O)O($CH_2CH_2O$)$_{n'}$—H, wherein R' represents the aliphatic residue of a fatty acid and n' represents the number of ethylene oxide units. In another aspect, n' is an integer ranging from about 2 to about 50, from about 3 to about 25 in another aspect, and from about 3 to about 10 in a further aspect. In still another aspect of the invention, R' is derived from a saturated or unsaturated fatty acid containing 8 to 30 carbon atoms. In another aspect, diesters can be formed by reacting two moles of the fatty acid with one mole of polyethylene or polypropylene glycol. The diesters can be represented by the formula: R'—C(O)O($CH_2CH_2O$)$_{n'}$(O)CR' where R' and n' are as defined immediately above.

Exemplary alkoxylated fatty acids include, but are not limited to, capric acid ethoxylate, lauric acid ethoxylate, myristic acid ethoxylate, stearic acid ethoxylate, oleic acid ethoxylate, coconut fatty acid ethoxylate, and the like, wherein the number of ethylene oxide units in each of the foregoing ethoxylates can range from 2 and above in one aspect, and from 2 to about 50 in another aspect. More specific examples of ethoxylated fatty acids are PEG-8 stearate (the 8 meaning the number of repeating ethylene oxide units), PEG-8 distearate, PEG-8 oleate, PEG-8 behenate, PEG-8 caprate, PEG-8 caprylate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates, PEG-distearates, PEG-ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Another fatty acid derivative that can be suitably employed in the compositions of the invention is a fatty acid ester. Fatty acids can be esterified by alcohols in the presence of a suitable acid catalyst to give a desired fatty acid ester. In one aspect, any of the saturated and unsaturated $C_8$ to $C_{30}$ fatty acids disclosed above can be esterified by a saturated or unsaturated $C_1$ to $C_{22}$ alcohol to give the respective fatty acid ester. In another aspect, longer chain fatty acid esters can be derived from the esterification of the above mentioned fatty acids by a saturated or unsaturated $C_8$ to $C_{30}$ fatty alcohol and can be represented by the formula: R"C(O)OR" wherein R" independently represents a saturated and unsaturated, linear and branched alkyl group containing 1 to 24 carbon atoms. Suitable fatty alcohols include the fatty alcohols that are disclosed below.

Exemplary fatty acid esters include, but are not limited to, methyl laurate, hexyl laurate, isohexyl laurate, decyl oleate, methyl cocoate, isopropyl stearate, isopropyl isostearate, butyl stearate, decyl stearate, octyl stearate, cetyl stearate, stearyl stearate, oleyl stearate, myristyl myristate, octyldodecyl stearoyl stearate, octylhydroxystearate, isopropyl myristate, oleyl myristate, isopropyl palmitate, ethyl hexyl palmitate, cetyl palmitate, decyl oleate, isodecyl oleate, oleyl oleate, isodecyl neopentanoate, diisopropyl sebacate, isostearyl lactate, lauryl lactate, cetearyl octanoate, and mixtures thereof.

Still other fatty esters suitable for use in the compositions of the present invention are mono-, di- and tri-alkyl and alkenyl esters of carboxylic acids, such as esters of $C_2$ to $C_8$ monocarboxylic acids, $C_4$ to $C_{10}$ dicarboxylic acids, $C_6$ to $C_{10}$ tricarboxylic acids (e.g., $C_1$ to $C_{22}$ esters of acetic acid, lactic acid, succinic acid, glutaric acid, adipic acid, citric acid, trimelletic acid, trimesic acid, and 1,3,5-pentane tricarboxylic acid). Specific non-limiting examples of mono-, di- and tri-alkyl and alkenyl esters of carboxylic acids include lauryl acetate, cetyl propionate, lauryl lactate, myristyl lactate, cetyl lactate, diisopropyl adipate, dihexyldecyl adipate, dioleyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono- and di-fatty acid esters, diethylene glycol mono- and di-fatty acid esters, polyethylene glycol mono- and di-fatty acid esters, propylene glycol mono- and di-fatty acid esters, polypropylene glycol mono- and di-fatty acid esters, and sorbitol mono- and di-fatty esters, wherein the acyl portion of the fatty acid ester is derived from a saturated or unsaturated $C_8$ to $C_{22}$ fatty acid. These esters can be optionally ethoxylated. Representative polyhydric alcohol fatty acid esters include, but are not limited to, polypropylene glycol monooleate, polypropylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Other polyhydric alcohol esters include the partial esters of polyglycerols. These esters contain 2 to 10 glycerol units and are esterified with 1 to 4 saturated or unsaturated, linear or branched, optionally hydroxylated $C_8$ to $C_{30}$ fatty acid residues. Representative partial esters of polyglycerols include, but are not limited to, diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, decaglycerol trihydroxystearate, and mixtures thereof.

The fatty alcohols suitable for use in the compositions of the invention include, but are not limited to, the saturated and unsaturated $C_8$-$C_{30}$ fatty alcohols. Exemplary fatty alcohols include capryl alcohol, pelargonic alcohol, capric alcohol, decyl alcohol, undecyl alcohol, lauryl alcohol, myristyl alcohol, cetyl alcohol, isocetyl alcohol, stearyl alcohol, isostearyl alcohol, cetearyl alcohol, palmitoleyl alcohol, elaidyl alcohol, sterol, oleyl alcohol, linoleyl alcohol, elaidolinoleyl alcohol, linolenyl alcohol, ricinoleyl alcohol, arachidyl alcohol, icocenyl alcohol, behenyl alcohol, erucyl alcohol, lignoceryl alcohol, ceryl alcohol, montanyl alcohol, myricyl alcohol, and mixtures thereof. Fatty alcohols are widely available and can be obtained through the hydrogenation of esterified vegetable and animal oils and fats.

Alkoxylated fatty alcohol compounds are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect of the invention, the ethoxylated fatty alcohols can be represented by the formula R'"—$(OCH_2CH_2)_{n''}$—OH, wherein R'"represents the aliphatic residue of the parent fatty alcohol and n" represents the number of ethylene oxide units. In another aspect of the invention, R'" is derived from a fatty alcohol containing 8 to 30 carbon atoms. In one aspect, n" is an integer ranging from 2 to 50, 3 to 25 in another aspect, and 3 to 10 in a further aspect. In a still further aspect, R'" is derived from a fatty alcohol set forth immediately in the paragraph above. Exemplary ethoxylated fatty alcohols are but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and mixed ethoxylated/propoxylated adducts of the foregoing fatty alcohols are also contemplated within the scope of the invention. The ethylene oxide and propylene oxide units of the ethoxylated/propoxylated fatty alcohols can be arranged in random or in blocky order.

Exemplary ethoxylated sterols include ethoxylated vegetable oil sterols such as, for example, soya sterols. The degree of ethoxylation is greater than about 5 in one aspect, and at least about 10 in another aspect. Suitable ethoxylated sterols are PEG-10 Soy Sterol, PEG-16 Soy Sterol and PEG-25 Soy Sterol.

Additional examples of ethoxylated alcohols are but are not limited to Beheneth 5-30 (the 5-30 meaning the range of repeating ethylene oxide units), Ceteareth 2-100, Ceteth 1-45, Cetoleth 24-25, Choleth 10-24, Coceth 3-10, C9-11 Pareth 3-8, C11-15 Pareth 5-40, C11-21 Pareth 3-10, C12-13 Pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, and Trideceth 2-10.

Specific examples of propoxylated alcohols are but are not limited to PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols are but are not limited to PPG-1 Beheneth-15, PPG-12 Capryleth-18, PPG-2-Ceteareth-9, PPG-4-Ceteareth-12, PPG-10-Ceteareth-20, PPG-1-Ceteth-1, PPG-1-Ceteth-5, PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2 C12-13 Pareth-8, PPG-2 C12-15 Pareth-6, PPG-4 C13-15 Pareth-15, PPG-5 C9-15 Pareth-6, PPG-6 C9-11 Pareth-5, PPG-6 C12-15 Pareth-12, PPG-6 C12-18 Pareth-11, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradeceth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4-Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Myreth-11, PPG-20-PEG-20 Hydrogenated Lanolin, PPG-2-PEG-11 Hydrogenated Lauryl Alcohol Ether, PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4, PPG-34-Steareth-3, PPG-38 Steareth-6, PPG-1 Trideceth-6, PPG-4 Trideceth-6, and PPG-6 Trideceth-8.

Guerbet esters are also suitable in the compositions of the invention. Guerbet esters can be formed from the esterification of a mono- or polyfunctional carboxylic acid by a Guerbet alcohol. Alternatively, the ester can be formed by reacting a Guerbet acid with a mono- or polyfunctional alcohol. For a review of Guerbet chemistry, see O'Lenick, A. J., Jr. 2001. Guerbet chemistry. *Journal of Surfactants and Detergents* 4: 311-315. Guerbet esters are commercially available from Lubrizol Advanced Materials, Inc. under product designations G-20, G-36, G-38, and G-66.

In addition to the foregoing benefit agents, other benefit agents for the hair and skin include, allantoin, urea, pyrrolidone carboxylic acid and its salts, hyaluronic acid and its salts, sorbic acid and its salts, amino acids (e.g., lysine, arginine, cystine, guanidine), $C_3$ to $C_6$ polyhydroxy alcohols such as glycerin, propylene glycol, hexylene glycol, hexanetriol, ethoxydiglycol, and sorbitol, and the esters thereof, polyethylene glycols (e.g., Polyox WSR-25, Polyox WSR-N-60K, and Polyox WSR-N-750, available from Dow Chemical), sugars and starches, sugar and starch derivatives (e.g., alkoxylated glucose), panthenols such as dl-panthenol, lactamide monoethanolamine, acetamide monoethanolamine, and the like, and mixtures thereof.

The natural and synthetic waxes, oils, fatty acids and alcohols, as well as the other benefit agents described above can be utilized in an amount ranging from about 0.1% to about 30% by weight in one aspect, from about 0.5% to 25% by weight in another aspect, from about 3% to 20% by weight in a further aspect, and from 5% to about 10% by weight in a still further aspect, based on the total weight of the composition in which it is included.

Pharmaceutical and Cosmeceutical Actives

The compositions of the present invention can be formulated with a pharmaceutical and/or a cosmeceutical active to deliver a desired effect. Examples of such active ingredients include, but are not limited to, caffeine, vitamin C, vitamin D, vitamin E, anti-stretch mark compounds, astringents (e.g., alum, oatmeal, yarrow, witch hazel, bayberry, and isopropyl alcohol), draining compounds, depilatories (e.g., calcium and sodium hydroxide, calcium or sodium thioglycolate, or mixtures thereof), hair growth promoting compounds (e.g., monoxidil), skin and hair nourishing compounds, skin and hair protecting compounds, self-tanning compounds (e.g., mono- or polycarbonyl compounds such as, for example, isatin, alloxan, ninhydrin, glyceraldehyde, mesotartaric aldehyde, glutaraldehyde, erythrulose, tyrosine, tyrosine esters, and dihydroxyacetone), UV absorbers (e.g., ethylhexyl methoxy cinnamate, octinoxate, octisalate, oxybenzone), skin lighteners (e.g., kojic acid, hydroquinone, arbutin, fruital, vegetal or plant extracts, such as lemon peel extract, chamomile, green tea, paper mulberry extract, and the like, ascorbyl acid derivatives, such as ascorbyl palmitate, ascorbyl stearate, magnesium ascorbyl phosphate, and the like), lip plumping compounds, anti-aging, anti-cellulite, and anti-acne compounds (e.g., acidic agents such as alpha-hydroxy acids (ANAs), beta-hydroxy acids (BHAs), alpha amino-acids, alpha-keto acids (AKAs), acetic acid, azelaic acid, and mixtures thereof), anti-inflammatory compounds (e.g., aspirin, ibuprofen, and naproxen), analgesics (e.g., acetaminophen), antioxidant compounds, antiperspirant compounds (e.g., aluminum halides, aluminum hydroxyhalides, aluminum sulfate, zirconium (zirconyl) oxyhalides, zirconium (zirconyl)hydroxyhalides, and mixtures or complexes thereof), deodorant compounds (e.g., 2-amino-2-methyl-1-propanol (AMP), ammonium phenolsulfonate; benzalkonium chloride; benzethonium chloride, bromochlorophene, cetyltrimethylammonium bromide, cetyl pyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarban, triclosan, zinc phenolsulfonate, zinc ricinoleate, and mixtures thereof); and suitable mixtures of any of the above.

Opacifying/Pearlescent Materials

Some formulations are often opacified by deliberately incorporating pearlescent materials therein to achieve a cosmetically attractive pearl-like appearance, known as pearlescence. An opacifier often is included in a composition to mask an undesirable aesthetic property, such as to improve the color of a composition that is darkened due to the presence of a particular ingredient, or to mask the presence of particulate matter in the composition. Opacifiers also are included in aqueous compositions to improve the aesthetics and consumer acceptance of an otherwise esthetically unpleasing composition. For example, an opacifier can impart a pearlescent appearance to a clear composition, thereby communicating an appearance of creaminess, mildness and body to the consumer. Persons skilled in the art are aware of problems faced by formulators in consistently preparing a stable pearlescent formulation. A detailed discussion is found in the article "Opacifiers and pearling agents in shampoos" by Hunting, *Cosmetic and Toiletries*, Vol. 96, pages 65-78 (July 1981), incorporated herein by reference.

The opacifying or pearlescent material includes ethylene glycol mono-stearate, ethylene glycol distearate, polyethylene glycol distearate, stearic alcohol, bismuth oxychloride coated mica, mica coated metal oxides (e.g., titanium dioxide, chromium oxide, iron oxides), myristyl myristate, guanine, glitter (polyester or metallic), and mixtures thereof. Other pearlescent materials can be found in U.S. Pat. No. 4,654,207, U.S. Pat. No. 5,019,376, and U.S. Pat. No. 5,384,114, which are herein incorporated by reference.

In one aspect, the amount of the pearlescent material can be used in amounts ranging from about 0.05% to about 10% by weight, and from about 0.1% to about 3% by weight in another aspect, based upon the total weight of the stabilized composition.

Opacifiers

An opacifier is an ingredient included in a composition to reduce or eliminate the clear or transparent appearance of the composition. In addition, an opacifier also can impart other advantageous properties to a composition, such as thickening, suspending and emulsifying properties.

An opacifier can be selected from a number of different chemical classes including inorganic compounds, e.g., various aluminum and magnesium salts, and organic compounds, like fatty alcohols, fatty esters and various polymers and copolymers. A representative listing of opacifiers is found in the CTFA Cosmetic Ingredient Handbook, J. Nikitakis, ed., The Cosmetic, Toiletry and Fragrance Association, Inc., Washington, D.C., 1988, at page 75.

Particulates

Numerous other substantially insoluble compounds and components which require stabilization and/or suspension can be utilized in the compositions of the invention. Examples of such other insoluble compounds include pigments, exfoliants, and anti-dandruff agents.

Exemplary pigments are metal compounds or semi-metallic compounds and may be used in ionic, nonionic or oxidized form. The pigments can be in this form either individually or in admixture or as individual mixed oxides or mixtures thereof, including mixtures of mixed oxides and pure oxides. Examples are the titanium oxides (e.g., $TiO_2$), zinc oxides (e.g., ZnO), aluminum oxides (for example, $Al_2O_3$), iron oxides (for example, $Fe_2O_3$), manganese oxides (e.g., MnO), silicon oxides (e.g., $SiO_2$), silicates, cerium oxide, zirconium oxides (e.g., $ZrO_2$), barium sulfate ($BaSO_4$), and mixtures thereof.

Other examples of pigments include D&C Red No. 30, D&C Red No. 36, D&C Orange No. 17, Green 3 Lake, Ext. Yellow 7 Lake, Orange 4 Lake, Red 28 Lake, the calcium lakes of D&C Red Nos. 7, 11, 31 and 34, the barium lake of D&C Red No. 12, the strontium lake D&C Red No. 13, the aluminum lakes of FD&C Yellow No. 5 and No. 6, the aluminum lakes of FD&C No. 40, the aluminum lakes of D&C Red Nos. 21, 22, 27, and 28, the aluminum lakes of FD&C Blue No. 1, the aluminum lakes of D&C Orange No. 5, the aluminum lakes of D&C Yellow No. 10; the zirconium lake of D&C Red No. 33, iron oxides, thermochromic dyes that change color with temperature, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide nanoparticles, barium oxide, ultramarine blue, bismuth citrate, hydroxyapatite, zirconium silicate, carbon black particles and the like. Other suitable particulates include various optical modifiers as described in U.S. Pat. No. 7,202,199.

Numerous cosmetically useful particulate exfoliating agents are known in the art, and the selection and amount is determined by the exfoliating effect desired from the use of the composition, as recognized by those skilled in the cosmetic arts. Useful exfoliating agents include, but are not limited to, natural abrasives, inorganic abrasives, synthetic polymers, and the like, and mixtures thereof. Representative exfoliants include, but are not limited to, ground or powdered pumice, stone, zeolites, nut shells (e.g., almond, pecan, walnut, coconut, and the like), nut meals (e.g., almond, and the like), fruit pits (e.g., apricot, avocado, olive, peach, and the like), hulls, seed and kernel (e.g., oat bran, corn meal, rice bran, grape seed, kiwi seed, wheat, jojoba seed, loofah seed, rose hip seed, and the like), plant matter (e.g., tea tree leaves, corn cob, fruit fibers, seaweed, loofah sponge, microcrystalline cellulose, and the like), bivalve shells (oyster shell, and the like), calcium carbonate, dicalcium pyrophosphate, chalk, silica, kaolin clay, silicic acid, aluminum oxide, stannic oxide, sea salt (e.g., Dead Sea salt), talc, sugars (e.g., table, brown, and the like), polyethylene, polystyrene, microcrystalline polyamides (nylons), microcrystalline polyesters, polycarbonates, and stainless steel fibers. The foregoing exfoliants can be used in the form of granules, powders, flours, and fibers.

Other generally insoluble components suitable for use in the present compositions include clay, swellable clay, laponite, gas bubbles, liposomes, microsponges, cosmetic beads and flakes. Cosmetic beads, flakes and capsules can be included in a composition for aesthetic appearance or can function as micro- and macro-encapsulants for the delivery of benefit agents to the skin and hair. Exemplary bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.).

Any suitable anti-dandruff agent can be employed in the compositions of the present invention. Exemplary anti-dandruff agents include, but are not limited to, sulfur, zinc pyrithione, zinc omadine, miconazole nitrate, selenium sulfide, piroctone olamine, N,N-bis(2-hydroxyethyl)undecenamide, cade oil, pine tar, *Allium cepa* extract *Picea abies* extract, and Undecyleneth-6, and the like, and mixtures thereof.

In one aspect of the invention, the amount of particulate component can range from about 0.1% to about 10% by weight based on the total weight of the composition.

Botanicals

Optionally, the compositions of the invention can contain botanical material extracts. Extracted botanical materials can include any water soluble or oil soluble material extracted from a particular plant, fruit, nut, or seed. In one aspect of the invention, the antiperspirant compositions the botanical actives are present in an amount ranging from about 0.1% to about 10% by weight, from about 0.5% to about 8% by weight in another aspect, and from about 1% to about 5% by weight in a further aspect, based of the total weight of the composition.

Suitable botanical agents can include, for example, extracts from *Echinacea* (e.g., sp. *angustifolia, purpurea, pallida*), yucca glauca, willow herb, basil leaves, Turkish oregano, carrot root, grapefruit, fennel seed, rosemary, tumeric, thyme, blueberry, bell pepper, blackberry, spirulina, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, and witch hazel. Botanical extracts include, for example, chlorogenic acid, glutathione, glycrrhizin, neohesperidin, quercetin, rutin, morin, myricetin, absinthe, and chamomile.

Cationic Polymers and Compounds

Cationic polymers and compounds are useful in the compositions of the invention. Those of ordinary skill in the art will recognize that many of these cationic agents serve multiple functions. Typically, these agents are useful as conditioners (e.g., hair and skin), antistatic agents, fabric softening, and as antimicrobial agents. Cationic polymers can be synthetically derived or obtained by modifying natural polymers such as the cationically modified polysaccharides and polygalactomannans.

Representative cationic polymers include but are not limited to homopolymers and copolymers derived from free radically polymerizable acrylic or methacrylic ester or amide monomers. The copolymers can contain one or more units derived from acrylamides, methacrylamides, diacetone acrylamides, acrylic or methacrylic acids or their esters, vinyllactams such as vinyl pyrrolidone or vinyl caprolactam, and vinyl esters. Exemplary polymers include copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name GAFQUAT™ by International Specialty Products Inc., Wayne, N.J.; the dimethyl amino ethyl methacrylate/vinyl caprolactam/vinyl pyrrolidone terpolymers, such as the product sold under the trade name GAFFIX™ VC 713 by International Specialty Products Inc.; the vinyl pyrrolidone/methacrylamidopropyl dimethylamine copolymer, marketed under the trade name STYLEZE™ CC 10 available from International Specialty Products Inc.; and the vinyl pyrrolidone/quaternized dimethyl amino propyl methacrylamide copolymers such as the product sold under the trade name GAFQUAT™ HS 100 by International Specialty Products, Inc.

Cationic agents can also be selected from the quaternary polymers of vinyl pyrrolidone and vinyl imidazole such as the products sold under the trade name Luviquat® (product designation FC 370 and FC 550) by BASF. Other cationic polymer agents that can be used in the compositions of the invention include polyalkyleneimines such as polyethyleneimines, polymers containing vinyl pyridine or vinyl pyridinium units, condensates of polyamines and epichlorhydrins, quaternary polysaccharides, quaternary polyurethanes, quaternary silicones, and quaternary derivatives of chitin.

Other non-limiting examples of quaternary ammonium compounds (monomeric and polymeric) useful as cationic agents in the present invention include acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, Quaternium-22, Quaternium-26, Quaternium-27, Quaternium-52, Quaternium-53, Quaternium-63, Quaternium-70, Quaternium-72, Quaternium-76, hydrolyzed collagen, PEG-2-cocomonium chloride, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, Polyquaternium-1, Polyquaternium-4, Polyquaternium-6, Polyquaternium-7, Polyquaternium-10, Polyquaternium-11, Polyquaternium-15, Polyquarternium-16, Polyquaternium-22, Polyquaternium-24, Polyquaternium-28, Polyquaternium-29, Polyquaternium-32, Polyquaternium-33, Polyquaternium-35, Polyquaternium-37, Polyquaternium-39, Polyquaternium-44, Polyquaternium-46, Polyquaternium-47, Polyquaternium-52, Polyquaternium-53, Polyquarternium-55, Polyquaternium-59, Polyquaternium-61, Polyquaternium-64, Polyquaternium-65, Polyquaternium-67, Polyquaternium-69, Polyquaternium-70, Polyquaternium-71, Polyquaternium-72, Polyquaternium-73, Polyquaternium-74, Polyquaternium-76, Polyquaternium-77, Polyquaternium-78, Polyquaternium-79, Polyquaternium-80, Polyquaternium-81, Polyquaternium-82, Polyquaternium-84, Polyquaternium-85, Polyquaternium-87, PEG-2-cocomonium chloride; and mixtures thereof.

Other useful cationic polymers include the cationic polygalactomannans (e.g., quaternized derivatives of guar and cassia, such as, guar hydroxypropyl trimmonium chloride, hydroxypropyl guar hydroxypropyl trimmonium chloride, and *cassia* hydroxypropyl trimmonium chloride).

Cationic agents useful in the invention also include, but are not limited to, proteins and protein derivatives, amines, protonated amine oxides, betaines, and the like. Protein derivatives include cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl hydrolyzed silk amino acids, hydroxypropyl trimonium hydrolyzed collagen, hydroxypropyl trimonium hydrolyzed keratin, hydroxypropyl trimonium hydrolyzed silk, hydroxypropyl trimonium hydrolyzed rice bran, hydroxypropyl trimonium hydrolyzed soy protein, hydroxypropyl trimonium hydrolyzed vegetable protein, hydroxypropyl trimonium hydrolyzed wheat protein, hydrolyzed wheat protein, hydrolyzed sweet almond protein, hydrolyzed rice protein, hydrolyzed soy protein, hydrolyzed milk protein, hydrolyzed vegetable protein, hydrolyzed keratin, hydrolyzed collagen, hydrolyzed wheat gluten, potassium cocoyl hydrolyzed collagen, hydroxypropyl trimonium hydrolyzed collagen, cocodimonium hydroxypropyl hydrolyzed milk protein, lauryldimonium hydroxypropyl hydrolyzed wheat protein, lauryldimonium hydroxypropyl hydrolyzed collagen, keratin amino acids, collagen amino acids, soyethyldimonium ethosulfate, soyethyl morpholinium ethosulfate, and the like.

The monomeric quaternary ammonium compounds include, for example, alkylbenzyldimethyl ammonium salts, betaines, heterocyclic ammonium salts, and tetraalkylammonium salts. Long-chain (fatty) alkylbenzyldimethyl ammonium salts are utilized as conditioners, as antistatic agents, and as fabric softeners, discussed in more detail below.

Non-limiting examples of alkylbenzyldimethylammonium salts include, but are not limited to, stearalkonium chloride, benzalkonium chloride, Quaternium-63, olealkonium chloride, didecyldimonium chloride, and the like. The betaine compounds include the alkylamidopropyl betaines and the alkylamidopropyl hydroxysultaines, as described in the formulas set forth previously above. Non-limiting examples of alkyl betaine compounds include oleyl betaine, coco-betaine, cocoamidopropyl betaine, coco-hydroxy sultaine, coco/oleamidopropyl betaine, coco-sultaine, cocoamidopropylhydroxy sultaine, and sodium lauramidopropyl hydroxyphostaine.

The heterocyclic ammonium salts include the alkylethyl morpholinium ethosulfates, isostearyl ethylimidonium ethosulfate, and the alkylpyridinium chlorides. Non-limiting examples of heterocyclic ammonium salts include, but are not limited to, cetylpyridinium chloride, isostearylethylimidonium ethosulfate, and the like.

Non-limiting examples of tetraalkylammonium salts include cocamidopropyl ethyldimonium ethosulfate, hydroxyethyl cetyldimonium chloride, Quaternium-18, and cocodimonium hyroxypropyl hydrolyzed protein, such as hair keratin, and the like.

A number of quaternary ammonium compounds are used as antistatic agents for fabric conditioning and fabric care. They include long-chain alkylated quaternary ammonium compounds such as dialkyldimethyl quaternary ammonium compounds, imidazoline quaternary compounds, amidoamine quaternary compounds, dialkyl ester quat derivatives of dihydroxypropyl ammonium compounds; dialkyl ester quat derivatives of methyltriethanol ammonium compounds, ester amide amine compounds, and diester quat derivatives of dimethyldiethanol ammonium chloride, as described in the review article by Whalley, "Fabric Conditioning Agents", HAPPI, pp. 55-58 (February 1995), incorporated herein by reference.

Non-limiting examples of dialkyldimethyl quaternary ammonium compounds, include N,N-dioleyl-N,N-dimethylammonium chloride, N,N-ditallowyl-N,N-dimethylammonium ethosulfate, N,N-di(hydrogenated-tallowyl)-N,N-dimethylammonium chloride, and the like. Non-limiting examples of imidazoline quaternary compounds include 1-N-methyl-3-N-tallowamidoethylimidazolium chloride, 3-methyl-1-tallowylamidoethyl-2-tallowylimidazolinium methylsulfate, and the like. Non-limiting examples of amidoamine quaternary compounds include N-alkyl-N-methyl-N,N-bis (2-tallowamidoethyl)ammonium salts where the alkyl group can be methyl, ethyl, hydroxyethyl, and the like. Non-limiting examples of dialkyl ester quat derivatives of dihydroxypropyl ammonium compounds include 1,2-ditallowoyloxy-3-N,N,N-trimethylammoniopropane chloride, 1,2-dicanoloyloxy-3-N,N,N-trimethylammoniopropane chloride, and the like.

In addition, other types of long chain (e.g., natural oil and fatty acid-derived) alkylated quaternary ammonium compounds are suitable fabric softening agents. In one aspect, the long-chain alkyl groups are derived from tallow, canola oil, or from palm oil, however, other alkyl groups derived from soybean oil and coconut oil, for example, are also suitable, as are lauryl, oleyl, ricinoleyl, stearyl, and palmityl groups. Representative compounds include, but not limited, to N,N-di (alkyloxyethyl)-N,N-dimethylammonium salts such as N,N-di(tallowyloxyethyl)-N,N-dimethylammonium chloride, N,N-di(canolyloxyethyl)-N,N-dimethylammonium chloride, and the like; N,N-di(alkyloxyethyl)-N-methyl-N-(2-hydroxyethyl)ammonium salts such as N,N-di(tallowyloxyethyl)-N-methyl-N-(2-hydroxyethyl)ammonium chloride, N,N-di(canolyloxyethyl)-N-methyl-N-(2-hydroxyethyl)ammonium chloride, and the like; N,N-di(2-alkyloxy-2-oxoethyl)-N,N-dimethylammonium salts, such as N,N-di(2-tallowyloxy-2-oxoethyl)-N,N-dimethylammonium chloride, N,N-di(2-canolyloxy-2-oxoethyl)-N,N-dimethylammonium chloride, and the like; N,N-di(2-alkyloxyethylcarbonyloxyethyl)-N,N-dimethylammonium salts, such as N,N-di(2-tallowyloxyethylcarbonyloxyethyl)-N,N-dimethylammonium chloride, N,N-di(2-canolyloxyethylcarbonyloxyethyl)-N,N-dimethylammonium chloride, and the like; N-(2-alkanoyloxy-2-ethyl)-N-(2-alkyloxy-2-oxoethyl)-N,N-dimethyl ammonium salts, such as N-(2-tallowoyloxy-2-ethyl)-N-(2-tallowyloxy-2-oxoethyl)-N,N-dimethyl ammonium chloride, N-(2-canoloyloxy-2-ethyl)-N-(2-canolyloxy-2-oxoethyl)-N,N-dimethyl ammonium chloride, and the like; N,N,N-tri(alkyloxyethyl)-N-methyl ammonium salts, such as N,N,N-tri(tallowyloxyethyl)-N-methylammonium chloride, N,N,N-tri(canolyloxyethyl)-N-methylammonium chloride, and the like; N-(2-alkyloxy-2-oxoethyl)-N-alkyl-N,N-dimethyl ammonium salts, such as N-(2-tallowyloxy-2-oxoethyl)-N-tallowyl-N,N-dimethyl ammonium chloride, N-(2-canolyloxy-2-oxoethyl)-N-canolyl-N,N-dimethyl ammonium chloride, and the like.

In another aspect, quaternary ammonium fabric softening compounds include N-methyl-N,N-bis(tallowamidoethyl)-N-(2-hydroxyethyl)ammonium methylsulfate and N-methyl-N,N-bis(hydrogenated-tallowamidoethyl)-N-(2-hydroxyethyl)ammonium methylsulfate, dialkyl esterquat derivatives of methyltriethanol ammonium salts such as the bis(acyloxyethyl)hydroxyethylmethylammonium methosulfate esterquats, and the like; and N,N-di(tallowoyloxyethyl)-N,N-dimethylammonium chloride, where the tallow chains are at least partially unsaturated.

In a further aspect, fabric softening agents include the well-known dialkyldimethyl ammonium salts such as N,N-ditallowyl-N,N-dimethyl ammonium methylsulfate, N,N-di(hydrogenated-tallowyl)-N,N-dimethyl ammonium chloride, N,N-distearyl-N,N-dimethyl ammonium chloride, N,N-dibehenyl-N,N-dimethylammonium chloride, N,N-di(hydrogenated tallow)-N,N-dimethyl ammonium chloride, N,N-ditallowyl-N,N-dimethyl ammonium chloride, N,N-distearyl-N,N-dimethyl ammonium chloride, N,N-dibehenyl-N,N-dimethyl ammonium chloride, and N,N-dimethyl-N-stearyl-N-benzylammonium chloride.

The foregoing monomeric and polymeric quaternary ammonium salt compounds can have any anionic group as a counter-ion, for example, chloride, bromide, methosulfate (i.e., methylsulfate), acetate, formate, sulfate, nitrate, and the like.

For fabric softening applications, any suitable quaternary ammonium agent can be utilized in combination with the staged core-shell polymer surfactant compositions of the present invention. For ester-containing fabric softening agents, the pH of the compositions can influence the stability of the fabric softening agents, especially in prolonged storage conditions. The pH, as defined in the present context, is measured in the neat compositions at about 20° C. In one aspect, the pH of the composition is less than about 6. In another aspect, the pH is in the range of from about 2 to about 5, and from about 2.5 to about 3.5 in a further aspect.

In one aspect, the cationic agent(s) can be employed in amounts ranging from about 0.05% to 15% by weight, from about 0.1% to about 10% by weight in another aspect, and from about 0.5% to about 3% by weight in a further aspect, based on the weight of the final composition, but is not limited thereto.

Preservatives

In one aspect, any preservative suitable for use in personal care, home care, health care, and institutional and industrial care products, can be used in the compositions of the present invention. Suitable preservatives include polymethoxy bicyclic oxazolidine, methyl paraben, propyl paraben, ethyl paraben, butyl paraben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, and suitable polyquaternium compounds disclosed above (e.g., Polyquaternium-1).

In another aspect, acid based preservatives are useful in the compositions of the present invention. The use of acid based preservatives facilitates the formulation of products in the low pH range. Lowering the pH of a formulation inherently provides an inhospitable environment for microbial growth. Moreover, formulating at low pH enhances the efficacy of acid based preservatives, and affords a personal care product which maintains an acidic pH balance on the skin as discussed by Wiechers, 2008, supra. Surprisingly, it has been discovered that the staged core-shell polymers of the invention can be used to thicken surfactant compositions formulated at low pH while maintaining excellent clarity and rheological properties such as viscosity and yield value.

Any acid based preservative that is useful in personal care, home care, health care, and institutional and industrial care products can be used in the compositions of the present invention. In one aspect the acid preservative is a carboxylic acid compound represented by the formula: $R^{53}C(O)OH$, wherein $R^{53}$ represents hydrogen, a saturated and unsaturated hydrocarbyl group containing 1 to 8 carbon atoms or $C_6$ to $C_{10}$ aryl. In another aspect, $R^{53}$ is selected from a hydrogen, a $C_1$ to $C_8$ alkyl group, a $C_2$ to $C_8$ alkenyl group, or phenyl. Exemplary acids are, but are not limited to, formic acid, acetic acid, propionic acid, sorbic acid, caprylic acid, and benzoic acid, and mixtures thereof.

In another aspect, suitable acids include but are not limited to, oxalic acid, succinic acid, glutaric acid, adipic acid, azelaic acid, maleic acid, fumaric acid, lactic acid, glyceric acid, tartronic acid malic acid, tartaric acid, gluconic acid, citric acid, ascorbic acid, salicylic acid, phthalic acid, mandelic acid, benzilic acid, and mixtures thereof.

Salts of the foregoing acids are also useful as long as they retain efficacy at low pH values. Suitable salts include the alkali metal (e.g., sodium, potassium, calcium) and ammonium salts of the acids enumerated above.

The acid based preservatives and/or their salts can be used alone or in combination with non-acidic preservatives typically employed in personal care, home care, health care, and institutional and industrial care products.

The preservatives typically comprise from about 0.01% to about 3.0% by weight in one aspect, from about 0.1% to about 1% by weight in another aspect, and from about 0.3% to about 1% by weight in a further aspect, of the total weight of the personal care compositions of the present invention.

Auxiliary Rheology Modifier

In another aspect of the invention, the compositions of the invention can be formulated in combination with one or more auxiliary rheology modifiers and thickeners. Suitable rheology modifiers and thickeners include synthetic and semi-synthetic rheology modifiers. Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule, wherein in one aspect the substituent is independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. No. 5,087,445; U.S. Pat. No. 4,509,949; and U.S. Pat. No. 2,798,053 herein incorporated by reference.

In one aspect, the AST rheology modifier or thickener is a crosslinked homopolymer polymerized from acrylic acid or methacrylic acid and is generally referred to under the INCI name of Carbomer. Commercially available Carbomers include Carbopol® polymers 934, 940, 941, 956, 980 and 996 available from Lubrizol Advanced Materials, Inc. In a further aspect, the rheology modifier is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect, the monomers can be polymerized in the presence of a steric stabilizer such as disclosed in U.S. Pat. No. 5,288,814, which is herein incorporated by reference. Some of the forgoing polymers are designated under INCI nomenclature as Acrylates/C10-30 Alkyl Acrylate Crosspolymer and are commercially available under the trade names Carbopol® 1342 and 1382, Carbopol® Ultrez 20 and 21, Carbopol® ETD 2020 and Pemulen® TR-1 and TR-2 from Lubrizol Advanced Materials, Inc.

In another aspect, the auxiliary rheology modifier can be a crosslinked, linear poly(vinyl amide/acrylic acid) copolymer as disclosed in U.S. Pat. No. 7,205,271, the disclosure of which is herein incorporated by reference.

Another class of optional synthetic rheology modifiers and thickeners suitable for use in the present invention includes the hydrophobically modified ASTs, commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an “associative monomer”, and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843, which are herein incorporated by reference. In addition, an extensive review of HASE polymers is found in Gregory D. Shay, Chapter 25, “Alkali-Swellable and Alkali-Soluble Thickener Technology A Review”, Polymers in Aqueous Media—Performance Through Association, Advances in Chemistry Series 223, J. Edward Glass (ed.), ACS, pp. 457-494, Division Polymeric Materials, Washington, D.C. (1989), the relevant disclosures of which are incorporated herein by reference. Commercially available HASE polymers are sold under the trade names, Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer) from Rohm & Haas, and Novethix™ L-10 (INCI Name: Acrylates/Beheneth-25 Methacrylate Copolymer) from Lubrizol Advanced Materials, Inc.

In another embodiment, acid swellable associative polymers can be used with the hydrophobically modified, cationic polymers of the present invention. Such polymers generally have cationic and associative characteristics. These polymers are free radical addition polymers polymerized from a monomer mixture comprising an acid sensitive amino substituted hydrophilic monomer (e.g., dialkylamino alkyl (meth)acrylates or (meth)acrylamides), an associative monomer (defined hereinabove), a lower alkyl (meth)acrylate or other free radically polymerizable comonomers selected from hydroxyalkyl esters of (meth)acrylic acid, vinyl and/or allyl ethers of polyethylene glycol, vinyl and/or allyl ethers of polypropylene glycol, vinyl and/or allyl ethers of polyethylene glycol/polypropylene glycol, polyethylene glycol esters of (meth) acrylic acid, polypropylene glycol esters of (meth)acrylic acid, polyethylene glycol/polypropylene glycol esters of (meth)acrylic acid), and combinations thereof. These polymers can optionally be crosslinked. By acid sensitive is meant that the amino substituent becomes cationic at low pH values, typically ranging from about 0.5 to about 6.5. Exemplary acid swellable associative polymers are commercially available under the trade name Structure® Plus (INCI Name: Acrylates/Aminoacrylates/C10-C30 Alkyl PEG-20 Itaconate) from Akzo Nobel, and Carbopol® Aqua CC (INCI Name: Polyacrylates-1 Crosspolymer) from Lubrizol Advanced Materials, Inc. In one aspect, the acid swellable polymer is a copolymer of one or more $C_1$-$C_5$ alkyl esters of (meth)acrylic acid, $C_1$-$C_4$ dialkylamino $C_1$-$C_6$ alkyl methacrylate, PEG/

PPG-30/5 alkyl ether, PEG 20-25 $C_{10}$-$C_{30}$ alkyl ether methacrylate, hydroxy $C_2$-$C_6$ alkyl methacrylate crosslinked with ethylene glycol dimethacrylate. Other useful acid swellable associative polymers are disclosed in U.S. Pat. No. 7,378,479, the disclosure of which is herein incorporated by reference.

Hydrophobically modified alkoxylated methyl glucoside, such as, for example, PEG-120 Methyl Glucose Dioleate, PEG-120 Methyl Glucose Trioleate, and PEG-20 Methyl Glucose Sesquistearate, available from Lubrizol Advanced Materials, Inc., under the trade names, Glucamate® DOE-120, Glucamate™ LT, and Gucanlate™ SSE-20, respectively, are also suitable as auxiliary rheology modifiers.

Polysaccharides obtained from tree and shrub exudates, such as gum Arabic, gum gahatti, and gum tragacanth, as well as pectin; seaweed extracts, such as alginates and carrageenans (e.g., lambda, kappa, iota, and salts thereof); algae extracts, such as agar; microbial polysaccharides, such as xanthan, gellan, and wellan; cellulose ethers, such as ethylhexylethylcellulose, hydroxybutylmethylcellulose, hydroxyethylmethylcellulose, hydroxypropylmethylcellulose, methylcellulose, carboxymethylcellulose, hydroxyethylcellulose, and hydroxypropylcellulose; polygalactomannans, such as fenugreek gum, cassia gum, locust bean gum, tara gum, and guar gum; starches, such as corn starch, tapioca starch, rice starch, wheat starch, potato starch and sorghum starch can also be employed in the compositions herein as suitable auxiliary thickeners and rheology modifiers.

The auxiliary rheology modifiers, when employed, can be used alone or in combination and typically are used in an amount ranging from about 0.1 wt. % to about 8 wt. % in one aspect, from about 0.3 wt. % to about 3 wt. % in another aspect, and from about 0.5 wt. % to about 2 wt. % in further aspect, based on the total weight of the personal care compositions of the present invention.

Emulsifier

Emulsifiers when employed in the compositions of the present invention include, but are not limited to, the $C_{12}$-$C_{22}$ fatty alcohols, $C_{12}$-$C_{22}$ alkoxylated alcohols, $C_{12}$-$C_{22}$ fatty acids, $C_{12}$-$C_{22}$ alkoxylated fatty acids (the alkoxylates each having 10 to 80 units of ethylene oxide, propylene oxide, and combinations of ethylene oxide/propylene oxide present in the molecule), $C_8$-$C_{22}$ APGs, ethoxylated sterols (wherein the number of ethylene oxide units ranges from 2 to about 150), partial esters of polyglycerols, esters and partial esters of polyols having 2 to 6 carbon atoms, partial esters of polyglycerols, and organosiloxanes, and combinations thereof.

The $C_8$-$C_{22}$ alkyl APG emulsifiers are prepared by reacting glucose or an oligosaccharide with primary fatty alcohols having 8 to 22 carbon atoms, and comprise a glucosidically bonded $C_8$-$C_{16}$ alkyl group on an oligoglucoside residue whose average degree of oligomerization is 1 to 2. In addition to the APGs described as surfactants above, APGs are available under the trademark Plantacare® (Cognis Corporation, Cincinnati, Ohio). Exemplary alkyl glucosides and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Emulsifiers based on the esters and partial esters of polyols having 2 to 6 carbon atoms are condensed with linear saturated and unsaturated fatty acids having 12 to 30 carbon atoms are, for example, the monoesters and diesters of glycerol or ethylene glycol or the monoesters of propylene glycol with saturated and unsaturated $C_{12}$-$C_{30}$ fatty acids.

Exemplary fatty alcohols and fatty acids, as well as their alkoxylates, the partial esters of polyglycerols, as well as the organosiloxanes are described above.

Chelating Agents

Chelating agents can be employed to stabilize the personal care, home care, health care, and institutional care compositions of the invention against the deleterious effects of metal ions. When utilized, suitable chelating agents include EDTA (ethylene diamine tetraacetic acid) and salts thereof such as disodium EDTA, citric acid and salts thereof, cyclodextrins, and the like, and mixtures thereof. Such suitable chelators typically comprise about 0.001 wt. % to about 3 wt. %, preferably about 0.01 wt. % to about 2 wt. %, and more preferably about 0.01 wt. % to about 1 wt. % of the total weight of the personal care compositions of the present invention.

Auxiliary Solvents and Diluents

The personal care, home care, health care, and institutional care compositions containing the thickened surfactant compositions of the present invention in combination with one or more of the foregoing active ingredients and/or with the one or more additives and/or adjuvants, conventionally or popularly included in personal care, health care, home care, and institutional care products discussed above can be prepared as water-free or water-based formulations, and formulations containing water-miscible auxiliary solvents and/or diluents, but are not limited thereto. Useful solvents commonly employed are typically liquids, such as water (deionized, distilled or purified), alcohols, fatty alcohols, polyols, and the like, and mixtures thereof. Non-aqueous or hydrophobic auxiliary solvents are commonly employed in substantially water-free products, such as nail lacquers, aerosol propellant sprays, or for specific functions, such as removal of oily soils, sebum, make-up, or for dissolving dyes, fragrances, and the like, or are incorporated in the oily phase of an emulsion. Non-limiting examples of auxiliary solvents, other than water, include linear and branched alcohols, such as ethanol, propanol, isopropanol, hexanol, and the like; aromatic alcohols, such as benzyl alcohol, cyclohexanol, and the like; saturated $C_{12}$ to $C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$ to $C_4$ alkoxylated alcohols and $C_2$ to $C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents or diluents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, $C_7$ to $C_{40}$ isoparaffins, alkyl carboxylic esters, such as ethyl acetate, amyl acetate, ethyl lactate, and the like, jojoba oil, shark liver oil, and the like. Some of the foregoing non-aqueous auxiliary solvents or diluents may also be conditioners and emulsifiers.

Propellants

Where desired, any known aerosol propellant can be utilized to deliver the personal care, home care, health care, and institutional care compositions containing staged core-shell polymers of the present invention in combination with one or more of the foregoing active ingredients and/or with the one or more additives and/or adjuvants, conventionally or popularly included in such products. Exemplary propellants include, but are not limited to, lower boiling hydrocarbons such as $C_3$-$C_6$ straight and branched chain hydrocarbons. Exemplary hydrocarbon propellants include propane, butane, isobutene, and mixtures thereof. Other suitable propellants include ethers, such as, dimethyl ether, hydrofluorocarbons, such as, 1,1-difluoroethane, and compressed gasses, such as air and carbon dioxide.

In one aspect, these compositions can contain from about 0.1% to about 60% by weight of a propellant, and from about 0.5 to about 35% by weight in another aspect, based on the total weight of the composition.

The staged core-shell polymers of the invention can be utilized in any personal care, home care, health care, and institutional and industrial care composition requiring rheology and/or aesthetic property modification. In a given composition or application, the staged core-shell polymers of this invention can, but need not, serve more than one function, such as a thickener, stabilizer, emulsifier, film former, carrier a deposition aid, and the like. The amount of staged core-shell polymer that can be employed depends upon the purpose for which they are included in a formulation and can be determined by person skilled in the formulation arts. Thus, as long as the physicochemical and functional properties of a desired product are achieved, a useful amount of staged core-shell polymer on a total composition weight basis, typically can vary in the range of from about 0.01% to about 25% by weight in one aspect, from about 0.1% to about 15% by weight in another aspect, from about 0.5% to about 10% by weight in a further aspect, and from about 1% to about 5% by weight in a still further aspect, but is not limited thereto.

The personal care, home care, health care, and institutional and industrial care compositions comprising the staged core-shell polymers of the invention can be packaged and dispensed from containers such as jars, tubes, sprays, wipes, roll-ons, sticks and the like, without limitation. There is no limitation as to the form of the product in which these polymers can be incorporated, so long as the purpose for which the product is used is achieved. For example, personal and health care products containing the staged core-shell polymers can be applied to the skin, hair, scalp, and nails, without limitation in the form of gels, sprays (liquid or foams), emulsions (creams, lotions, pastes), liquids (rinses, shampoos), bars, ointments, suppositories, and the like.

In one personal care aspect, the staged core-shell polymers of this invention are suitable for preparation of personal care (cosmetics, toiletries, cosmeceuticals), including, without limitation, hair care products (shampoos, combination shampoos, such as "two-in-one" conditioning shampoos), post-shampoo rinses, setting and style maintenance agents (including setting aids, such as gels and sprays, grooming aids such as pomades, conditioners, perms, relaxers, hair smoothing products, and the like), skin care products (facial, body, hands, scalp and feet), such as creams, lotions and cleansing products, antiacne products, antiaging products (exfoliant, keratolytic, anticellulite, antiwrinkle, and the like), skin protectants (sun care products, such as sunscreens, sunblock, barrier creams, oils, silicones and the like), skin color products (whiteners, lighteners, sunless tanning accelerators and the like), hair colorants (hair dyes, hair color rinses, highlighters, bleaches and the like), pigmented skin colorants (face and body make-ups, foundation creams, mascara, rouge, lip products, and the like) bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softness, and the like).

Toiletries and beauty aids containing the polymers of the invention can include, without limitation, hair-removal products (shaving creams and lotions, epilators, after-shaving skin conditioner, and the like), hair growth promoting products, deodorants and antiperspirants, oral care products (mouth, teeth, gums), such as mouth wash, dentifrice, such as toothpaste, tooth powder, tooth polishes, tooth whiteners, breath fresheners, denture adhesives, and the like; facial and body hair bleach and the like. Other beauty aids that can contain the staged core-shell polymers of the invention and include, without limitation, sunless tanning applications containing artificial tanning accelerators, such as dihydroxyacetone (DHA), tyrosine, tyrosine esters and the like: skin depigmenting, whitening and lightening, formulations containing such active ingredients as kojic acid, hydroquinone, arbutin, fruital, vegetable or plant extracts, (lemon peel extract, chamomile, green tea, paper mulberry extract, and the like), ascorbyl acid derivatives ascorbyl palmitate, ascorbyl stearate, magnesium ascorbyl phosphate and the like).

The staged core-shell polymers of the invention are useful as suspending agents for particulates making them suitable for dermal cleansing products containing particulates, insoluble benefit agents, microabrasives, and abrasives and combinations thereof. Dermal cleansing products include shampoos, body washes, shower gels, bath gels, masks and skin cleansers.

Body Wash

In one aspect, a personal care composition in which the polymer of this invention is useful is a body wash. Typical components of a body wash, in addition to the staged core-shell polymer thickener and water are: at least one surfactant; a sufficient pH adjusting agent (base and/or acid) to attain a pH of from about 3.5 to about 7.5 in one aspect, from about 4.0 to about 6.5 in another aspect, and from about 5.0 to about 6.0 in a further aspect; and optional ingredients selected from the adjuvants, additives and benefit agents discussed above, and mixtures thereof, including benefit agents selected from silicones, pearlizing agents, vitamins, oils, fragrances, dyes, preservatives including acids, botanicals, exfoliating agents, insoluble gas bubbles, liposomes, microsponges, cosmetic beads and flakes. In one aspect, the surfactant is an anionic surfactant. In another aspect, the surfactant is a mixture of an anionic surfactant and an amphoteric surfactant, in optional combination with a non-ionic surfactant. In another aspect, the surfactant is a mixture of an anionic surfactant and an amphoteric surfactant, in optional combination with a cationic and/or a non-ionic surfactant. In one aspect, the anionic surfactant can be present in an amount ranging from about 5% to about 40% by weight, from about 6% to about 30% by weight in another aspect, and from 8% to about 25% by weight in a further aspect, based on the total weight of the body wash composition. When mixtures of anionic and amphoteric surfactants are used, the ratio of anionic surfactant:amphoteric surfactant can range from about 1:1 to about 15:1 in one aspect, from about 1.5:1 to about 10:1 in another aspect, from about 2.25:1 to about 9:1 in a further aspect, and from about 4.5:1 to about 7:1 in a still further aspect. The amount of the acrylic polymer blend(s) can range from about 0.5% to about 5% by weight in one aspect, from about 1% to about 3% by weight in another aspect, and from about 1.5% to about 2.5% by weight in a further aspect, based on the total weight of the body wash composition.

Body wash embodiments of the invention can be formulated as moisturizing body washes, antibacterial body washes, bath gels, shower gels, liquid hand soaps, body scrubs; bubble baths, facial scrubs, foot scrubs, and the like.

Shampoo Compositions

In one aspect, a personal care composition in which the polymer of this invention is useful is a shampoo. Typical components of a shampoo, in addition to the staged core-shell polymer thickener and water are: at least one surfactant; a sufficient pH adjusting agent (base and/or acid) to attain a pH of from about 3.0 to about 7.5 in one aspect, from about 3.5 to about 6.0 in another aspect, and from about 4.0 to about 5.5 in a further aspect; and optional ingredients selected from the adjuvants, additives and benefit agents discussed above, and mixtures thereof, including benefit agents selected from conditioning agents (e.g., silicones and/or cationic conditioning agents; small and/or large particle sized silicones), pearlizing agents, vitamins, oils, fragrances, dyes, preservatives including acids, botanicals, and insoluble gas bubbles, liposomes, and cosmetic beads and flakes, and anti-dandruff agents, and mixtures thereof. In one aspect, the surfactant is an anionic surfactant. In another aspect, the surfactant is a mixture of an anionic surfactant and an amphoteric surfactant, in optional combination with a cationic and/or a non-ionic surfactant. In one aspect, the anionic surfactant can be present in an amount ranging from about 5% to about 40% by weight, from about 6% to about 30% by weight in another aspect, and from 8% to about 25% by weight in a further aspect, based on the total weight of the shampoo composition. When mixtures of anionic and amphoteric surfactants are used, the ratio of anionic surfactant to amphoteric surfactant can range from about 1:1 to about 10:1 in one aspect, from about 2.25:1 to about 9:1 in another aspect, and from about 4.5:1 to about 7:1 in a further aspect. The amount of staged core-shell polymer can range from about 0.5% to about 5% by weight in one aspect, from about 1% to about 3% by weight in another aspect, and from about 1.5% to about 2.5% by weight in a further aspect, based on the total weight of the shampoo composition.

Shampoo embodiments of the invention can be formulated as 2-in-1 shampoos, baby shampoos, conditioning shampoos, bodifying shampoos, moisturizing shampoos, temporary hair color shampoos, 3-in-1 shampoos, anti-dandruff shampoos, hair color maintenance shampoos, acid (neutralizing) shampoos, medicated shampoos, and salicylic acid shampoos, and the like.

Liquid Fatty Acid Soap Based Cleansers

In one aspect, a personal care composition in which the polymer of this invention is useful is a fatty acid soap based cleanser. Typical components of a fatty acid based soap cleanser, in addition to the staged core-shell polymer thickener are: at least one fatty acid salt; an optional surfactant or mixture of surfactants; a sufficient pH adjusting agent (base and/or acid) to attain a pH of above 7 in one aspect, from about 7.5 to about 14 in another aspect, from about 8 to about 12 in still another aspect, and from about 8.5 to about 10 in a further aspect; and optional ingredients selected from the adjuvants, additives and benefit agents discussed above, and mixtures thereof, including benefit agents selected from silicones, humectants, pearlizing agents, vitamins, oils, fragrances, dyes, preservatives, botanicals, anti-dandruff agents, exfoliating agents, insoluble gas bubbles, liposomes, microsponges, cosmetic beads and flakes.

In one aspect, the fatty acid soaps are selected from at least one the fatty acid salt (e.g., sodium, potassium, ammonium) containing from about 8 to about 22 carbon atoms. In another aspect of the invention the liquid soap composition contains at least one fatty acid salt containing from about 12 to about 18 carbon atoms. The fatty acids utilized in the soaps can be saturated and unsaturated and can be derived from synthetic sources, as well as from the saponification of fats and natural oils by a suitable base (e.g., sodium, potassium and ammonium hydroxides). Exemplary saturated fatty acids include but are not limited to octanoic, decanoic, lauric, myristic, pentadecanoic, palmitic, margaric, steric, isostearic, nonadecanoic, arachidic, behenic, and the like, and mixtures thereof. Exemplary unsaturated fatty acids include but are not limited to the salts (e.g., sodium, potassium, ammonium) of myristoleic, palmitoleic, oleic, linoleic, linolenic, and the like, and mixtures thereof. The fatty acids can be derived from animal fat such as tallow or from vegetable oil such as coconut oil, red oil, palm kernel oil, palm oil, cottonseed oil, olive oil, soybean oil, peanut oil, corn oil, and mixtures thereof. The amount of fatty acid soap that can be employed in the liquid cleansing compositions of this embodiment ranges from about 1% to about 50% by weight in one aspect, from about 10% to about 35% by weight in another aspect, and from about 12% to 25% by weight in a further aspect of the invention, based on the weight of the total composition.

An optional anionic surfactant can be present in the soap composition in an amount ranging from about 1% to about 25% by weight in one aspect, from about 5% to about 20% by weight in another aspect, and from 8% to about 15% by weight in a further aspect, based on the weight of the total weight of the soap composition. Mixtures of anionic and amphoteric surfactants can be used. The ratio of anionic surfactant to amphoteric surfactant can range from about 1:1 to about 10:1 in one aspect, from about 2.25:1 to about 9:1 in another aspect, and from about 4.5:1 to about 7:1 in a further aspect.

In the foregoing soap embodiments of the invention, the amount of staged core-shell polymer can range from about 0.5% to about 5% by weight in one aspect, from about 1% to about 3% by weight in another aspect, and from about 1.5% to about 2.5% by weight in a further aspect, based on the total weight of the soap composition.

The liquid fatty acid soap based cleanser embodiments of the invention can be formulated as body washes, bath gels, shower gels, liquid hand soaps, body scrubs; bubble baths, facial scrubs, and foot scrubs, 2-in-1 shampoos, baby shampoos, conditioning shampoos, bodifying shampoos, moisturizing shampoos, temporary hair color shampoos, 3-in-1 shampoos, anti-dandruff shampoos, hair color maintenance shampoos, acid (neutralizing) shampoos, anti-dandruff shampoos, medicated shampoos, and salicylic acid shampoos, and the like.

Fixatives

The term “fixative” as applied to polymers encompasses the properties of film-formation, adhesion, or coating deposited on a surface on which the polymer is applied. The terms “hair styling, hair setting, and hair fixative” as commonly understood in the hair care arts, and as used herein, refer collectively to hair setting agents that are hair fixatives and film formers and which are topically applied to the hair to actively contribute to the ease of styling and/or holding of a hair set, and to maintain the restylability of the hair set. Hence, hair setting compositions include hair styling, hair fixative, and hair grooming products that conventionally are applied to the hair (wet or dry) in the form of gels, rinses, emulsions (oil-in-water, water-in-oil or multiphase), such as lotions and creams, pomades, sprays (pressurized or non-pressurized), spritzes, foams, such as mousses, shampoos, solids, such as sticks, semisolids and the like, or are applied from a hair setting aid having the hair setting composition impregnated therein or coated thereon, to leave the hair setting agent in contact on the hair for some period until removed, as by washing.

In one embodiment, hair setting compositions encompasses products comprising at least one staged core-shell polymer of the present invention and a fixative polymer as a hair setting agent. The product can be applied to the hair (wet or dry) before, during or after configuring the hair into the shape (curly or straight) desired, without limitation as to product form. The staged core-shell polymers of the present invention are useful in combination with commercially available auxiliary hair fixative polymers, such as nonionic, cationic, and amphoteric hair setting polymers, cationic conditioning polymers, and combinations thereof.

Conventional hair fixative and hair styling polymers include natural gums and resins and polymers of synthetic origin. Listings of commercially available hair fixative and conditioning fixative polymers can be readily found in the INCI Dictionary, on supplier websites, and in the trade literature. See, for example, the Polymer Encyclopedia published in Cosmetics & Toiletries®, 117(12), December 2002 (Allured Publishing Corporation, Carol Stream, Ill.), the relevant disclosures of which are incorporated herein by reference.

Suitable commercially available fixative polymers include, polyacrylates, polyvinyls, polyesters, polyurethanes, polyamides, polyquaterniums, modified cellulose, starches, and mixtures thereof. These polymers can be nonionic, anionic, cationic and amphoteric in nature and include without limitation one or more of polyoxyethylenated vinyl acetate/crotonic acid copolymers, vinyl acetate crotonic acid copolymers, vinyl methacrylate copolymers, monoalkyl esters of poly(methyl vinyl ether (PVM)/maleic acid (MA)), such as, for example, ethyl, butyl and isopropyl esters of PVM/MA copolymer, acrylic acid/ethyl acrylate/N-tert-butyl-acrylamide terpolymers, and poly (methacrylic acid/acrylamidomethyl propane sulfonic acid), acrylates copolymer, octylacrylamide/acrylates/butylaminoethyl methacrylate copolymer, acrylates/octylacrylamide copolymer, vinyl acetate (VA)/crotonates/vinyl neodeanoate copolymer, poly(N-vinyl acetamide), poly(N-vinyl formamide), corn starch modified, sodium polystyrene sulfonate, polyquaterniums such as, for example, Polyquaternium-4, Polyquaternium-11, Polyquaternium-24, Polyquaternium-28, Polyquaternium-29, Polyquaternium-32, Polyquaternium-34, Polyquaternium-37, Polyquaternium-39, Polyquaternium-44, Polyquaternium-46, Polyquaternium-47, Polyquarternium-55, Polyquaternium-69, Polyquaternium-87, polyether-1, polyurethanes, VA/acrylates/lauryl methacrylate copolymer, adipic acid/dimethylaminohydroxypropyl diethylene AMP/acrylates copolymer, methacrylol ethyl betaine/acrylates copolymer, polyvinylpyrrolidone (PVP), vinyl pyrrolidone (VP)/dimethylaminoethylmethacrylate copolymer, VP/methacrylamide/vinyl imidazole copolymer, VP/dimethylaminopropylamine (DMAPA) acrylates copolymer, VP/vinylcaprolactam/DMAPA acrylates copolymer, VP/dimethylaminoethylmethacrylate copolymer, VP/DMAPA acrylates copolymer, vinyl caprolactam/VP/dimethylaminoethyl methacrylate copolymer, VA/butyl maleate/isobornyl acrylate copolymer, VA/crotonates copolymer, acrylate/acrylamide copolymer, VA/crotonates/vinyl propionate copolymer, VP/vinyl acetate/vinyl propionate terpolymers, VA/crotonates, VP/vinyl acetate copolymer, VP/acrylates copolymer, VA/crotonic acid/vinyl proprionate, acrylates/acrylamide, acrylates/octylacrylamide, acrylates/hydroxyacrylates copolymer, acrylates/hydroxyesteracrylates copolymer, acrylates/stereth-20 methacrylate copolymer, tert-butyl acrylate/acrylic acid copolymer, diglycol/cyclohexanedimethanol/isophthalates/sulfoisophthalates copolymer, VA/butyl maleate and isobornyl acrylate copolymer, VA/alkylmaleate half ester/N-substituted acrylamide terpolymers, vinyl caprolactam/VP/methacryloamidopropyl trimethylammonium chloride terpolymer, methacrylates/acrylates copolymer/amine salt, polyvinylcaprolactam, hydroxypropyl guar, poly (methacrylic acid/acrylamidomethyl propane sulfonic acid (AMPSA), ethylenecarboxamide (EC)/AMPSA/methacrylic acid (MAA), poylurethane/acrylate copolymers and hydroxypropyl trimmonium chloride guar, acrylates copolymer, acrylates crosspolymer, AMP-acrylates/allyl methacrylate copolymer, polyacrylate-14, polyacrylate-2 crosspolymer, acrylates/lauryl acrylate/stearyl acrylate/ethylamine oxide methacrylate copolymer, methacryloyl ethyl betaines/methacrylates copolymer, polyurethane/acrylates copolymer, pyrrolidone carboxylic acid salt of chitosan, chitosan glycolate, cationic polygalactomannans, such as, for example, quaternized derivatives of guar, such as, for example, guar hydroxypropyl trimmonium chloride and hydroxypropyl guar hydroxypropyl trimmonium chloride, and quaternized derivatives of cassia, such as, for example, hydroxypropyl trimonium chloride cassia. Other suitable fixative polymers are disclosed in U.S. Pat. No. 7,205,271, the disclosure of which is herein incorporated by reference.

In one embodiment, an exemplary hair care composition comprises a staged core-shell polymer of the present invention and a fixative polymer in amounts effective to provide to the hair care composition a property, such as a hair fixative property, a hair conditioning property, a viscid property (thickening, rheology modifying), or a combination thereof. Optionally, the hair care composition can include one or more of an auxiliary hair conditioning agent, an auxiliary rheology modifying agent, solvents, propellants, and a combination thereof.

The fixative polymer typically comprises about 0.01% to about 25% by weight in one aspect, from about 0.1% to about 10% by weight in another aspect, and about 0.2% to about 5% by weight in a further aspect, of the total weight of the fixative composition.

Cosmeceuticals

In one cosmeceutical aspect, the staged core-shell polymers can be employed as a thickener for active skin treatment lotions and creams containing, as active ingredients, acidic anti-aging, anti-cellulite, and anti-acne agents, hydroxy carboxylic acids, such as alpha-hydroxy acid (AHA), beta-hydroxy acid (BHA), alpha-amino acid, alpha-keto acids (AKAs), and mixtures thereof. In one aspect, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, alpha-lipoic acid, salicylic acid, AHA salts and derivatives, such as arginine glycolate, ammonium glycolate, sodium glycolate, arginine lactate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxy propanoic acid, beta-hydroxybutyric acid, beta-phenyl lactic acid, beta-phenylpyruvic acid, and the like. Alpha-amino acids include, without being limited thereto, alpha-amino dicarboxylic acids, such as aspartic acid, glutamic acid, and mixtures thereof, sometimes employed in combination with fruit acid. AKAs include pyruvic acid. In some antiaging compositions, the acidic active agent may be retinoic acid, a halocarboxylic acid, such as trichloroacetic acid, an acidic antioxidant, such as ascorbic acid (vitamin C), a mineral acid, phytic acid, lysophosphatidic acid, and the like. Some acidic anti-acne actives, for example, can include salicylic acid, derivatives of salicylic acid, such as 5-octanoyl-salicylic acid, retinoic acid, and its derivatives, and benzoic acid.

A discussion of the use and formulation of active skin treatment compositions is in *COSMETICS & TOILETRIES*, C&T Ingredient Resource Series, "AHAs & Cellulite Products How They Work", published 1995, and "Cosmeceuticals", published 1998, both available from Allured Publishing Corporation, incorporated herein by reference. Compositions containing alpha-amino acids acidified with ascorbic acid are described in U.S. Pat. No. 6,197,317 B1, and a commercial cosmeceutical preparation utilizing these acids in an anti-aging, skin care regimen is sold under the tradename, AFAs, by exCel Cosmeceuticals (Bloomfield Hills, Mich.). The term "AFA", as described in the supplier's trade literature, was coined by the developer to describe the amino acid/vitamin C combination as Amino Fruit Acids and as the acronym for "Amino acid Filaggrin based Antioxidants."

Health Care

Health care embodiments in which the instant polymers can be included are medical products, such as topical and non-topical pharmaceuticals, and devices. In the formulation of pharmaceuticals, a polymer embodiment of the invention can be employed as a thickener and/or lubricant in such products as syrups, creams, pomades, gels, pastes, ointments, tablets, gel capsules, purgative fluids (enemas, emetics, colonics, and the like), suppositories, anti-fungal foams, eye products (ophthalmic products, such as eye drops, artificial tears, glaucoma drug delivery drops, contact lens cleaner, and the like), ear products (wax softeners, wax removers, otitis drug delivery drops, and the like), nasal products (drops, ointments, sprays, and the like), and wound care (liquid bandages, wound dressings, antibiotic creams, ointments, and the like), without limitation thereto.

Other health care embodiments relate to foot care products, such as keratolytic corn and callous removers, foot soaks, medicated foot products such as antifungal athlete's foot ointments, gels, sprays, and the like, as well as antifungal, anti-yeast, and antibacterial creams, gels, sprays, and ointments.

In addition, the instant polymers can be included in topical, transdermal, and non-topical pharmaceutical applications, and devices as thickeners, spreading aids, suspending agents, and film formers in skin protective sprays, creams, lotions, gels, and sticks for in the formulation of insect repellants, itch relief agents, antiseptic agents, disinfectants, sun blocks, sun screens, skin tightening and toning agents, and in wart removal compositions, and the like.

In another pharmaceutical aspect, the polymers of the invention can be employed in the manufacture of pharmaceutical dosage forms (e.g. tablets, caplets, capsules, and the like) for the controlled release and targeted delivery of active pharmacologically active ingredients and medicaments to the stomach and gut. They can be employed as pharmaceutical excipients such as binders, enteric coatings, film formers and controlled release agents. They can be used alone or in combination with other controlled release and/or enteric polymers known in the pharmaceutical arts.

This invention is illustrated by the following examples that are merely for the purpose of illustration and are not to be regarded as limiting the scope of the invention or the manner in which it can be practiced. Unless specifically indicated otherwise, parts and percentages are given by weight.

Methods

Molecular Weight Determination

The number average molecular weights referenced herein are measured by GPC using a PL-GPC 220 high temperature GPC instrument manufactured by Polymer Laboratories (Varian, Inc.). Approximately 0.02 g polymer sample is dissolved in 5 ml of dimethyl acetamide (DMAc), containing 250 ppm of butylated hydroxytoluene (BHT) and 0.05 molar $NaNO_3$. The test sample solution is gently shaken for about two hours and filtered by passing the sample solution through a 0.45 μm PTFE disposable disc filter. The chromatographic conditions are: Mobile phase: DMAc, with 250 ppm BHT and 0.05 m $NaNO_3$, 70° C., 1.0 ml/min. Sample size: 100 μl Column set: PLgel (Guard+2×Mixed-A), all 10 μm, in series. Waters Empower Pro LC/GPC software is used to analyze the results and to calculate $M_n$ of the core and shell polymer components of the invention.

Viscosity

Brookfield rotating spindle method (all viscosity measurements reported herein are conducted by the Brookfield method whether mentioned or not): The viscosity measurements are calculated in mPa·s, employing a Brookfield rotating spindle viscometer, Model RVT (Brookfield Engineering Laboratories, Inc.), at about 20 revolutions per minute (rpm), at ambient room temperature of about 20 to 25° C. (hereafter referred to as viscosity). Spindle sizes are selected in accordance with the standard operating recommendations from the manufacturer. Generally, spindle sizes are selected as follows:

| Spindle Size No. | Viscosity Range (mPa · s) |
|---|---|
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | >50,000 |

The spindle size recommendations are for illustrative purposes only. The artisan of ordinary skill in the art will select a spindle size appropriate for the system to be measured.

Yield Value

Yield Value, also referred to as Yield Stress, is defined as the initial resistance to flow under stress. It is measured by the Brookfield Yield Value (BYV) Extrapolation Method using a Brookfield viscometer (Model RVT) at ambient room temperature of about 20 to 25° C. The Brookfield viscometer is used to measure the torque necessary to rotate a spindle through a liquid sample at speeds of 0.5 to 100 rpm. Multiplying the torque reading by the appropriate constant for the spindle and speed gives the apparent viscosity. Yield Value is an extrapolation of measured values to a shear rate of zero. The BYV is calculated by the following equation:

$$BYV, dyn/cm^2=(\eta_{\alpha 1}-\eta_{\alpha 2})/100$$

where $\eta_{\alpha 1}$ and $\eta_{\alpha 2}$=apparent viscosities obtained at two different spindle speeds (0.5 rpm and 1.0 rpm, respectively). These techniques and the usefulness of the Yield Value measurement are explained in Technical Data Sheet Number 244 (Revision: 5/98) from Noveon Consumer Specialties of Lubrizol Advanced Materials, Inc., herein incorporated by reference.

Clarity

The clarity (turbidity) of a composition is determined in Nephelometric Turbidity Units (NTU) employing a nephelometric turbidity meter (Mircro 100 Turbidimeter, HF Scientific, Inc.) at ambient room temperature of about 20 to 25° C. Distilled water (NTU=0) is utilized as a standard. Six dram screw cap vials (70 mm×25 mm) are filled almost to the top with test sample and centrifuged at 100 rpm until all bubbles are removed. Upon centrifugation, each sample vial is wiped with tissue paper to remove any smudges before placement in the turbidity meter. The sample is placed in the turbidity meter and a reading is taken. Once the reading stabilizes the NTU value is recorded. The vial is given one-quarter turn and another reading is taken and recorded. This is repeated until four readings are taken. The lowest of the four readings is reported as the turbidity value. Compositions having an NTU value of about 50 or greater were judged hazy or turbid.

Suspension Stability Test

Suspension Testing Procedure: The ability of a polymer system to suspend active and/or aesthetically pleasing insoluble oily and particulate materials is important from the standpoint of product efficacy and appeal. A six dram vial (approximately 70 mm high×25 mm in diameter) is filled to the 50 mm point with a bath gel test formulation. Each sample vial is centrifuged to remove any trapped air bubbles contained in the formulation. Cosmetic beads (e.g., Lipopearl™ gelatin capsules; average diameter 500-3000 microns) are weighed into the centrifuged sample (1.0 wt. % based on the weight of the total composition) and stirred gently with a wooden stick until they are uniformly dispersed throughout the bath gel sample. The position of approximately 10 of the beads within each sample vial is noted by drawing a circle around the bead with black marker pen on the outer glass surface of the vial and photographed to establish the initial position of the beads within the gel. The vials are placed in a 45° C. oven to age for a 12 week period. The bead suspension properties of each sample is monitored on a daily basis. The suspension results are visually ranked using a scale of 3 to 0 where: 3 indicates no noticeable settling/rise relative to the initial bead position in the gel; 2 indicates slight settling/rise or less than approximately ¼ drop/rise in distance relative to the initial bead position in the gel; 1 indicates greater than ¼ drop/rise to ½ drop/rise in distance relative to the initial position in the bath gel; and 0 indicates greater than ½ drop/rise in distance relative to the initial position of the bead in the bath gel. A rating of 0 or 1 designates that a sample failed, and a rating of 2 or 3 indicates that the sample passed.

Abbreviation and Trade Name Ingredient List

The following ingredients are utilized in the examples of the present invention:

| Monomers | |
|---|---|
| AA | Acrylic acid |
| ACE | ACE ™ Hydroxyl acrylate monomer is the reaction product of acrylic acid with Cardura ™. Cardura is the glycidyl ester of VERSATIC ™ acid 10, a highly branched saturated carboxylic acid containing 10 carbon atoms |
| nBA | n-Butyl Acrylate |
| tBAM | t-butyl acrylamide |
| EA | Ethyl Acrylate |
| 2-EHA | 2-Ethylhexyl Acrylate |
| HEMA | Hydroxyethyl Methacrylate |
| MA | Methyl Acrylate |
| MAA | Methacrylic Acid |
| NVP | N-vinyl pyrrolidone |
| STY | Styrene |
| TEGDMA | Triethyleneglycol Dimethacrylate (crosslinker) |
| TMPDAE | Trimethylolpropane Diallyl ether (crosslinker) |
| TMPTA | Trimethylolpropane Triacrylate (crosslinker) |
| VND | Vinyl neodecanoate |
| **Components** | |
| Aculyn ™ 38 | INCI Name: Acrylates/Vinyl Neodecanoate Crosspolymer (an emulsion copolymer of vinyl neodecanoate and one or more monomers of acrylic acid, methacrylic acid or one of their simple esters crosslinked with an allyl ether of trimethylolpropane or pentaerythritol), Rohm and Haas Company |
| Carbopol ® Aqua SF-1 | INCI Name: Acrylates Copolymer (an emulsion copolymer of two or more monomers consisting of acrylic acid, methacrylic acid or one of their simple esters), Lubrizol Advanced Materials, Inc. |
| Ceteath-20 | Ethoxylated-20 Cetyl Alcohol - 20 moles of ethylation |
| Chembetaine ™ CAD | Cocamidopropyl Betaine (amphoteric surfactant), Lubrizol Advanced Materials, Inc. |
| Chembetaine ™ CGF | Cocamidopropyl Betaine (amphoteric surfactant - glycerin free), Lubrizol Advanced Materials, Inc. |
| Chembetaine ™ LEC | INCI Name: Lauramidopropyl Betaine (amphoteric surfactant), Lubrizol Advanced Materials, Inc. |
| Chemonic ™ SI-7 | PEG-7 Glyceryl Soyate (nonionic surfactant), Lubrizol Advanced Materials, Inc. |
| Chemoryl ™ SFB-10SK | INCI Name: Disodium Laureth Sulfosuccinate (and) Sodium Cocoyl Isethionate (and) Cocamidopropyl Betaine (sulfate and amide free surfactant blend), Lubrizol Advanced Materials, Inc. |
| Chemoxide ™ CAW | INCI Name: Cocamidopropylamine Oxide (amine oxide surfactant), Lubrizol Advanced Materials, Inc. |
| Dow Corning ® 2-8194 Silicone | INCI Name: Amodimethicone and Trideceth-12 and Cetrimonium Chloride (microemulsion of amine functional silicone polymers), Dow Corning |
| Ethal SA-20 | INCI Name: Steareth-20, Ethox Chemicals, LLC |
| Florabeads ™ Gypsy Rose | INCI Name: Jojoba Esters (exfoliating agent pigmented with Red 30 (and) Talc), International Flora Technologies, Ltd. |
| Florabeads ™ Sonora Sand | INCI Name: Jojoba Esters (exfoliating agent pigmented with iron oxides, Red 30 (and) Talc, $TiO_2$, Yellow 5 Lake), International Flora Technologies, Ltd. |

-continued

| | |
|---|---|
| Florasun ® 90 | INCI Name: *Helianthus Annuus* (sunflower oil), International Flora Technologies, Ltd. |
| Foamaster ® DF-160L | Mineral Oil Based Defoamer, Cognis Corporation |
| Geogard ® Ultra | INCI Name: Gluconolatone (and) Sodium Benzoate, (preservative), Lonza Inc |
| Glucam ™ E-10 | INCI Name: Methyl Gluceth-10 (nonionic surfactant/humectant), Lubrizol Advanced Materials, Inc. |
| Hycar7 2671 | Acrylic Latex Binder, Lubrizol Advanced Materials, Inc. |
| Jaguar Excel | INCI Name: Guar Hydroxypropyltrimonium Chloride (quaternized quar gum), Rhodia Inc. |
| Lebermuth No. 50-8001-30 | Fragrance Oil (apple fresh green), The Lebermuth Company, Inc. |
| Lebermuth No. 90-3000-62 | Fragrance Oil (tangerine grapefruit), The Lebermuth Company, Inc. |
| Lipopearl ™ 0091 Beads | Pigmented Cosmetic Beads of Gelatin and Cellulose Gum containing Tridecyl Stearate, Tridecyl Trimellitate, Chromium Hydroxide Green, Mica, Titanium Dioxide, Tocopheryl Acetate, and Vitamin E, Lipo Technologies Inc. |
| Lipopearl ™ 0293 Beads | Pigmented Cosmetic Beads of Gelatin and Cellulose Gum containing Tridecyl Stearate, Tridecyl Trimellitate, Neopentyl Glycol, Mica, Titanium Dioxide, Tocopheryl Acetate, and Vitamin E, Lipo Technologies Inc. |
| Liposphere ™ 0031 | Pigmented Cosmetic Beads containing personal care benefit agents (Dimethicone, Neopentyl Glycol), Lipo Technologies Inc. |
| Merquat ® Plus | Polyquaternium-39 (cationic conditioning polymer; a terpolymer of acrylic acid, diallyl dimethyl ammonium chloride and acrylamide), Nalco Company |
| Neolone ® 950 | Methylisothiazolinone (preservative), Rohm and Haas Company |
| N-Hance ® 3000 | INCI Name: Guar Hydroxypropyltrimonium Chloride (quaternized quar gum), Ashland Inc. (Ashland Aqualon Functional Ingredients) |
| Phenonip | Blend of phenoxyethanol, methylparaben, ethylparaben, propylparaben, butylparaben and isobutylparaben, (antibacterial), Clariant Corpoaration-Nipa Laboratories |
| Printrite ® 595 | Acrylic Latex Binder, Lubrizol Advanced Materials, Inc. |
| Rheocare ™ TTA | INCI Name: Acrylates Copolymer (an emulsion copolymer of two or more monomers consisting of acrylic acid, methacrylic acid or one of their simple esters), Cognis Corporation |
| Stereath-20 | Ethoxylated stearyl alcohol containing 20 moles of ethoxylation |
| Sulfochem ™ ALS | Ammonium Lauryl Sulfate (anionic surfactant), Lubrizol Advanced Materials, Inc. |
| Sulfochem ™ AOS | Sodium C14-15 Olefin Sulfonate (anionic surfactant), Lubrizol Advanced Materials, Inc. |
| Sulfochem ™ ALS-K | Ammonium Lauryl Sulfate (anionic surfactant preserved with Kathon ® CG preservative from Rohm and Haas Company), Lubrizol Advanced Materials, Inc. |
| Sulfochem ™ EA-3 | Ammonium Lauryl Ether Sulfate - 3 moles of ethoxylation (anionic surfactant), Lubrizol Advanced Materials, Inc. |
| Sulfochem ™ ES-2 CWK | Sodium Lauryl Ether Sulfate - 2 moles of ethoxylation (anionic surfactant preserved with Kathon ® CG preservative from Rohm and Haas Company), Lubrizol Advanced Materials, Inc. |
| Sulfochem ES-2K | Sodium Lauryl Ether Sulfate - 2 moles of ethoxylation (anionic surfactant preserved with Kathon ® CG preservative from Rohm and Haas Company), Lubrizol Advanced Materials, Inc. |
| Sulfochem ™ ES-70 | Sodium Lauryl Ether Sulfate - 2 moles of ethoxylation (anionic surfactant), Lubrizol Advanced Materials, Inc. |
| Sulfochem ™ SLS | Sodium Lauryl Sulfate (anionic surfactant), Lubrizol Advanced Materials, Inc. |
| Tween 20 | Polysorbate 20 (solubilizer), Croda Inc |
| Unispheres NTL-2312 | INCI Name: Mannitol (and) Cellulose (and) Hydroxypropyl Methylcellulose (pigmented with chromium hydroxide green and loaded with vitamin E), Induchem AG |
| Versene ™ 220 | Tetrasodium Ethylenediaminetetraacetate Tetrahydrate (chelating agent), Dow Chemical |
| Zema ™ Propanediol | Bio-based 1,3-propanediol, DuPont, Tate & Lyle |

Example 1

Two Stage Polymers

Into an agitator equipped first (feed) reactor containing 68.6 grams of deionized water (D.I.) and 6.67 grams of sodium lauryl sulfate (30% active in water wt./wt.), 130.4 grams of ethyl acrylate and 69 grams of methacrylic acid are added under nitrogen atmosphere and mixed at 500 rpm to form a monomer emulsion. To an agitator equipped second reactor are added 1,340 grams of deionized water and 3.17 grams of sodium lauryl sulfate (30% active in water wt./wt.). The contents of the second reactor are heated with mixing agitation (200 rpm) under a nitrogen atmosphere. When the contents of the second reactor reaches a temperature of approximately 84° C., 27.0 grams of ammonium persulfate solution (2.0% aqueous solution wt./wt.) is injected into the heated surfactant solution. The monomer emulsion from the feed reactor is gradually metered (9.37 g/min.) into the second reactor over a period of about 30 minutes at a reaction temperature maintained at approximately 85° C. and allowed to react in a first stage polymerization reaction to form linear core polymer particles of ethyl acrylate/methacrylic acid copolymer. Following the initial addition of the monomer emulsion into the second reactor, the second stage monomer emulsion is prepared in the feed reactor by adding 274.4 grams of deionized water (D.I), 26.67 grams of sodium lauryl sulfate (30% active in water wt./wt.), 521 grams of ethyl acrylate, 276 grams of methacrylic acid, and 3.0 grams of trimethylolpropane triacrylate. The monomer emulsion containing the added trimethylolpropane triacrylate is then metered into the second reactor over a period of 120 minutes at a controlled rate (7.5 g/min.) at a temperature maintained at approximately 85° C. and polymerized in the presence of the linear core polymer particles in a second stage reaction to form a crosslinked polymer shell (over the core polymer particles) comprising polymerized ethyl acrylate/methacrylic acid/trimethylolpropane triacrylate copolymer. With the emulsion monomer feed, 60 grams of ammonium persulfate (0.37% aqueous solution wt./wt.) is simultaneously metered into the reaction mixture in the second reactor and the temperature of the reaction is maintained at about 85° C. for an additional two and half hours to complete polymerization. The resulting polymer emulsion product is cooled to room temperature, discharged from the reactor and recovered. The core and shell monomer components are set forth in Tables 1 and 1A, respectively, and the polymer stage compositional information is presented in Table 1C.

Example 2

Into an agitator equipped first (feed) reactor containing 68.6 grams of deionized water (D.I.) and 6.67 grams of sodium lauryl sulfate (30% active in water wt./wt.), 5.0 grams of Ethal SA 20, 130.4 grams of ethyl acrylate and 69 grams of methacrylic acid are added under nitrogen atmosphere and mixed at 500 rpm to form a monomer emulsion. To an agitator equipped second reactor are added 1340 grams of deionized water and 3.17 grams of sodium lauryl sulfate (30% active in water wt./wt.). The contents of the second reactor are heated with mixing agitation (200 rpm) under a nitrogen atmosphere. When the contents of the second reactor reaches a temperature of approximately 84° C., 27.0 grams of an ammonium persulfate solution (2.0% aqueous solution wt./wt.) is injected into the heated surfactant solution. The monomer emulsion from the feed reactor is gradually metered at a feed rate of 1.87 g/min. into the second reactor over a period of 30 minutes at a reaction temperature maintained at approximately 85° C. The monomer emulsion is reacted in a first stage polymerization to form linear core polymer particles of ethyl acrylate/methacrylic acid copolymer.

Following the initial addition of the monomer emulsion into the second reactor, the second stage monomer emulsion is prepared in the feed reactor by adding 274.4 grams of deionized water (D.I.), 26.67 grams of sodium lauryl sulfate (30% active in water wt./wt.), 20.0 grams of Ethal SA 20, 521.6 grams of ethyl acrylate and 276 grams of methacrylic acid and 3.0 grams of trimethylolpropane triacrylate. The monomer emulsion containing the added trimethylolpropane triacrylate is then metered into the second reactor over a period of 120 minutes at a controlled rate at a temperature maintained at approximately 85° C. With the second stage emulsion monomer feed, 0.37% ammonium persulfate solution (aqueous solution wt./wt.) is simultaneously metered at 0.67 ml/min. into the reaction mixture in the second reactor. The monomer emulsion containing the crosslinking monomer is polymerized in the presence of the linear core polymer particles in the second stage reaction to form a crosslinked polymer shell (over the core polymer particles). The temperature of the reaction is maintained at about 85° C. for an additional two and half hours to complete the polymerization. The resulting polymer emulsion product is cooled to room temperature, discharged from the reactor and recovered. The core and shell monomer components are set forth in Tables 1 and 1A, respectively, and the polymer stage compositional information is presented in Table 1C.

Example C-1

Comparative

An acrylic based emulsion polymer having a crosslinked core and linear shell identified as polymer C-1 is polymerized from the components set forth in Table 1. The emulsion polymerization procedure set forth in Example 2 was followed except that a crosslinked core polymer is synthesized in the first stage reaction followed by the synthesis of a linear polymer shell. In this example, 10% of the monomer emulsion prepared in the feed reactor as set forth in Example 2 is metered into the second reactor over a time period of 6 minutes at a temperature maintained at 85° C. and at a feed rate of 24 ml/min. 3.0 grams of a crosslinking monomer (TMPTA) is then added to the second reactor and mixed for 10 minutes to obtain homogeneous monomer emulsion. 27.0 grams of ammonium persulfate (2.0% aqueous solution wt./wt.) is injected into the reactor with agitation and polymerized to form a crosslinked core particle. After a 10 minute hold, the second stage comonomer emulsion (except the cross-linker) as set forth in Example 2 is metered at 10.54 g/ml into the second reactor over a 2 hour period at a temperature maintained at 85° C. The second stage monomer emulsion containing no crosslinker is polymerized in the presence of the crosslinked polymer core particles. The shell polymer is devoid of a crosslinking monomer component. The resulting polymer emulsion product is cooled to room temperature, discharged from the reactor and recovered.

Example C-2

Comparative

An acrylic based linear emulsion polymer identified as polymer C-2 is polymerized from the components set forth in Table 1. The polymer is synthesized as set forth in Example 2, except that the polymerization is terminated following the first stage reaction and recovered.

Example C-3

Comparative

An acrylic based crosslinked emulsion polymer designated as polymer C-3 is polymerized from the components set forth in Table 1. The crosslinking monomer is TMPTA. The polymer is synthesized as set forth in Example 2 except that the polymerization is terminated following the first stage reaction and recovered.

Examples 2, 3, 3a, 3b, 5, 7 to 14 and 16 to 19

Two Stage Polymers

Two stage core-shell polymers are polymerized from the components set forth in Tables 1 and 1A in accordance with the procedures set forth in Example 2. Polymer stage compositional information is presented in Table 1C.

The polymer of Example 9a is evaluated to determine its particle morphology. Spherical particles of core-shell morphology are observed by transmission electron microscopy (TEM) using ruthenium staining which has an affinity for styrene. The polymer of Example 9A comprises a styrene rich core stage relative to the shell stage which is devoid of styrene. To obtain the TEM image, a small capillary tube is used to aliquot a sample (approximately 5 μl) of the polymer emulsion into approximately 5 ml of D.I. water. Approximately 10 μl of the diluted sample is placed on a carbon coated Formvar TEM grid. The grid is placed on a screen suspended over a vaporizing solution of ruthenium and sodium hypochlorite (0.05 g of ruthenium added to 10 ml sodium hypochlorite (6% aqueous wt./wt.). The grid is contacted with the vapor for approximately 1.5 hours, allowed to dry and the stained polymer sample is observed under a Phillips CM12 transmission electron microscope at an acceleration voltage of 120 kV at 100K resolution. The TEM image is set forth in FIG. 4.

Figure 4:
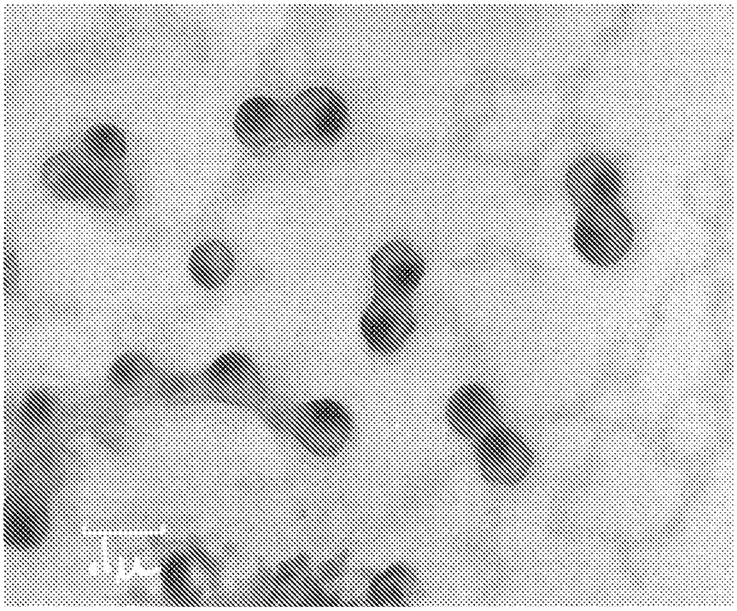
FIG. 4 shows a transmission electron micrograph (TEM) image of a staged core-shell polymer of the invention.

In FIG. 4 is seen numerous polymer particles which are visible as agglomerated spheres having a dark (ruthenium stained—styrene rich) central core region surrounded by a grey (unstained—devoid of styrene) outer shell region.

Example 4

Multi-Stage Polymerization

A three stage polymer is made as follows: Into an agitator equipped first (feed) reactor containing 34.3 grams of deionized water (D.I.) and 3.3 grams of sodium lauryl sulfate (30% active in water wt./wt.), 2.5 grams of Ethal SA-20, 65.1 grams of ethyl acrylate and 34.5 grams of methacrylic acid are added under nitrogen atmosphere and mixed at 500 rpm to form a monomer emulsion. To an agitator equipped second reactor are added 600 grams of deionized water and 1.27 grams of sodium lauryl sulfate (30% active in water wt./wt.). The contents of the second reactor are heated with mixing agitation (200 rpm) under a nitrogen atmosphere. When the contents of the second reactor reaches a temperature of approximately 84° C., 11.0 grams of an ammonium persulfate solution (2.0% aqueous solution wt./wt.) is injected into the heated surfactant solution. The monomer emulsion from the feed reactor (maintained at approximately 85° C.) is gradually metered at a feed rate of 0.94 g/min. into the second reactor over a period of 15 minutes. The monomer emulsion is reacted in a first stage polymerization to form linear core polymer particles of ethyl acrylate/methacrylic acid copolymer.

Following the initial addition of the monomer emulsion into the second reactor, a second stage monomer emulsion is prepared in the feed reactor by adding 171.5 grams of deionized water (D.I.), 16.67 grams of sodium lauryl sulfate (30% active in water wt./wt.), 12.5 grams of Ethal SA-20, 325.5 grams of ethyl acrylate and 172.5 grams of methacrylic acid, and 1.50 grams of trimethylolpropane triacrylate (TMPTA). The monomer emulsion containing the added TMPTA (maintained at approximately 85° C.) is metered into the second reactor over a period of 75 minutes at a controlled rate. With the second stage emulsion monomer feed, 0.25% ammonium persulfate solution (aqueous solution wt./wt.) is simultaneously metered at 0.67 ml/min. into the reaction mixture contained in the second reactor. The second stage monomer emulsion is polymerized in the presence of the linear core polymer particles in the second stage reaction to form a crosslinked polymer shell (over the core polymer particles).

Following the second stage polymerization reaction, a third stage monomer emulsion is prepared in the feed reactor by adding 137.2 grams of deionized water (D.I.), 13.33 grams of sodium lauryl sulfate (30% active in water wt./wt.), 10.0 grams of Ethal SA-20, 325.5 grams of ethyl acrylate, 260.4 grams of methacrylic acid, and 1.60 grams of TMPTA. In a third stage reaction, the monomer emulsion containing the higher level of TMPTA (maintained at approximately 85° C.) is metered into the second reactor over a period of 60 minutes at a constant feed rate. Along with the emulsion monomer feed, 0.25% ammonium persulfate solution (aqueous solution wt./wt.) is simultaneously metered at 0.67 ml/min. into the reaction mixture. The monomer emulsion is polymerized in the presence of the two stage linear core/crosslinked shell polymer particles obtained in the second stage to form a second crosslinked polymer shell (over the two stage core-shell polymer particles) with an increased crosslinked gradient zone. The temperature of the reaction is maintained at about 85° C. for an additional two and half hours to complete the polymerization. The resulting polymer emulsion product is cooled to room temperature, discharged from the reactor and recovered. The multistage monomer components and amounts are identified in Tables 1, 1A, 1B, respectively, and polymer stage compositional information is presented in Table 1C.

Examples 6 and 15

Multi-Staged Polymerization

Multi-staged core-shell polymers are polymerized from the components set forth in Tables 1,1A and 1B in accordance with the procedures and conditions set forth in Example 4. Table 1C presents polymer stage compositional information.

TABLE 1

(First Stage Monomer Components[1])

| Ex. No. | EA | nBA | 2-EHA | ACE | VND | NVP | STY | tBAM | HEMA | MAA | TMPTA |
|---|---|---|---|---|---|---|---|---|---|---|---|
| C-1 | 65.2 | — | — | — | — | — | — | — | — | 34.5 | 0.3 |
| C-2 | 65.5 | — | — | — | — | — | — | — | — | 34.5 | — |
| C-3 | 65.1 | — | — | — | — | — | — | — | — | 34.5 | 0.4 |
| 1 | 65.4 | — | — | — | — | — | — | — | — | 34.6 | — |
| 2 | 65.4 | — | — | — | — | — | — | — | — | 34.6 | — |
| 3 | 65.4 | — | — | — | — | — | — | — | — | 34.6 | — |
| 3a | 65.4 | — | — | — | — | — | — | — | — | 34.6 | |
| 3b | 65.4 | — | — | — | — | — | — | — | — | 34.6 | |
| 4 | 65.4 | — | — | — | — | — | — | — | — | 34.6 | — |
| 5 | 70.4 | — | — | — | — | — | — | — | — | 29.6 | — |
| 6 | 65.5 | — | — | — | — | — | — | — | — | 34.5 | — |
| 7 | 60.4 | — | — | — | 5.0 | — | — | — | — | 34.6 | — |
| 8 | 60.4 | — | — | — | — | 5.0 | — | — | — | 34.6 | — |

TABLE 1-continued

| (First Stage Monomer Components[1]) | | | | | | | | | | |
|---|---|---|---|---|---|---|---|---|---|---|
| Ex. No. | EA | nBA | 2-EHA | ACE | VND | NVP | STY | tBAM | HEMA | MAA | TMPTA |
| 9 | 62.4 | — | — | — | — | — | 3.0 | — | — | 34.6 | — |
| 9a | 62.4 | — | — | — | — | — | 3.0 | — | — | 34.6 | — |
| 10 | 62.4 | — | — | — | — | — | — | 3.0 | — | 34.6 | — |
| 11 | 60.4 | — | — | 5.0 | — | — | — | — | — | 34.6 | — |
| 12 | 55.5 | 5.2 | — | — | — | — | — | — | — | 39.3 | — |
| 13 | 52.5 | — | 5.3 | — | — | — | — | — | — | 42.2 | — |
| 14 | 59.6 | 5.5 | — | — | — | — | — | — | — | 34.9 | — |
| 15 | 49.8 | 5.0 | — | — | — | — | — | — | — | 45.2 | — |
| 16 | 65.1 | — | — | — | — | — | — | — | — | 34.9 | — |
| 17 | 65.4 | — | — | — | — | — | — | — | — | 34.6 | — |
| 18 | 60.4 | — | — | — | — | — | — | — | 5.0 | 34.6 | — |
| 19 | 64.9 | — | — | — | — | — | — | — | 10.0 | 25.1 | — |

[1]All monomer components are expressed in wt. % of the total monomer mixture for the stage.

TABLE 1A

| (Second Stage Monomer Components) | | | | | | | | | | | | | | |
|---|---|---|---|---|---|---|---|---|---|---|---|---|---|---|
| Ex. No. | EA | MA | nBA | 2-EHA | ACE | VND | NVP | STY | tBAM | HEMA | MAA | AA | TMPTA | TMPDAE |
| C-1 | 65.4 | — | — | — | — | — | — | — | — | — | 34.6 | — | — | — |
| C-2 | — | — | — | — | — | — | — | — | — | — | — | — | — | — |
| C-3 | — | — | — | — | — | — | — | — | — | — | — | — | — | — |
| 1 | 65.2 | — | — | — | — | — | — | — | — | — | 34.5 | — | 0.3 | — |
| 2 | 65.2 | — | — | — | — | — | — | — | — | — | 34.5 | — | 0.3 | — |
| 3 | 65.1 | — | — | — | — | — | — | — | — | — | 34.5 | — | 0.4 | — |
| 3a | 65.1 | — | — | — | — | — | — | — | — | — | 34.5 | — | 0.4 | — |
| 3b | 65.1 | — | — | — | — | — | — | — | — | — | 34.5 | — | 0.4 | — |
| 4 | 65.1 | — | — | — | — | — | — | — | — | — | 34.6 | — | 0.3 | — |
| 5 | 70.15 | — | — | — | — | — | — | — | — | — | 29.5 | — | 0.35 | — |
| 6 | 65.17 | — | — | — | — | — | — | — | — | — | 34.53 | — | 0.3 | — |
| 7 | 60.2 | — | — | — | — | 5.0 | — | — | — | — | 34.5 | — | 0.3 | — |
| 8 | 60.2 | — | — | — | — | — | 5.0 | — | — | — | 34.5 | — | 0.3 | — |
| 9 | 62.2 | — | — | — | — | — | — | 3.0 | — | — | 34.5 | — | 0.3 | — |
| 9a | 65.2 | — | — | — | — | — | — | — | — | — | 34.5 | — | 0.3 | — |
| 10 | 62.2 | — | — | — | — | — | — | — | 3.0 | — | 34.5 | — | 0.3 | — |
| 11 | 60.2 | — | — | — | 5.0 | — | — | — | — | — | 34.5 | — | 0.3 | — |
| 12 | 53.7 | 5.0 | 5.0 | — | — | — | — | — | — | — | 36.0 | — | 0.3 | — |
| 13 | 49.7 | 5.0 | — | 5.0 | — | — | — | — | — | — | 40.0 | — | 0.3 | — |
| 14 | 54.6 | 5.0 | 5.0 | — | — | — | — | — | — | — | 32.0 | 3.0 | 0.3 | 0.1 |
| 15 | 49.65 | — | 5.0 | — | — | — | — | — | — | — | 45.0 | — | 0.35 | — |
| 16 | 54.6 | 5.0 | 5.0 | — | — | — | — | — | — | — | 32.0 | 3.0 | 0.3 | 0.1 |
| 17 | 65.1 | — | — | — | — | — | — | — | — | — | 34.5 | — | 0.3 | 0.1 |
| 18 | 60.2 | — | — | — | — | — | — | — | — | 5.0 | 34.5 | — | 0.3 | — |
| 19 | 64.7 | — | — | — | — | — | — | — | — | 10.0 | 25.0 | — | 0.3 | — |

[1]All monomer components are expressed in wt. % of the total monomer mixture for the stage.

TABLE 1B

| (Third Stage Monomer Components) | | | | | |
|---|---|---|---|---|---|
| Ex. No. | EA | nBA | MAA | TMPTA | TEGDMA |
| C-1 | — | — | — | — | — |
| C-2 | — | — | | — | — |
| C-3 | — | — | | — | — |
| 1 | — | — | | — | — |
| 2 | — | — | | — | — |
| 3 | — | — | | — | — |
| 4 | 65.1 | — | 34.5 | 0.4 | — |
| 5 | — | — | | — | — |
| 6 | 65.15 | — | 34.5 | 0.3 | 0.05 |
| 7 | — | — | — | — | — |
| 8 | — | — | — | — | — |
| 9 | — | — | — | — | — |
| 10 | — | — | — | — | — |
| 11 | — | — | — | — | — |

TABLE 1B-continued

| (Third Stage Monomer Components) | | | | | |
|---|---|---|---|---|---|
| Ex. No. | EA | nBA | MAA | TMPTA | TEGDMA |
| 12 | — | — | — | — | — |
| 13 | — | — | — | — | — |
| 14 | — | — | — | — | — |
| 15 | 49.55 | 5.0 | 45.0 | 0.35 | 0.1 |
| 16 | — | — | — | — | — |
| 17 | — | — | — | — | — |
| 18 | — | — | — | — | — |
| 19 | — | — | — | — | — |

[1]All monomer components are expressed in wt. % of the total monomer mixture for the stage.

TABLE 1C

| (Polymer Stage Components) | | | | |
|---|---|---|---|---|
| Ex. No. | Polymer Type | Wt. % Core | Wt. % Shell (second stage) | Wt. % Shell (third stage) |
| C-1 | X-linked[1] core/linear shell | 10 | 90 | — |
| C-2 | linear | 100 | — | — |
| C-3 | X-linked | 100 | — | — |
| 1 | linear core/X-linked shell | 20 | 80 | — |
| 2 | linear core/X-linked shell | 20 | 80 | — |
| 3 | linear core/X-linked shell | 20 | 80 | — |
| 3a | linear core/X-linked shell | 50 | 50 | — |
| 3b | linear core/X-linked shell | 60 | 40 | — |
| 4 | linear core/X-linked $2^{nd}$ stage/X-linked $3^{rd}$ stage | 10 | 50 | 40 |
| 5 | linear core/X-linked shell | 25 | 75 | — |
| 6 | linear core/X-linked $2^{nd}$ stage/X-linked $3^{rd}$ stage | 10 | 50 | 40 |
| 7 | linear core/X-linked shell | 20 | 80 | — |
| 8 | linear core/X-linked shell | 20 | 80 | — |
| 9 | linear core/X-linked shell | 20 | 80 | — |
| 9a | linear core/X-linked shell | 20 | 80 | — |
| 10 | linear core/X-linked shell | 20 | 80 | — |
| 11 | linear core/X-linked shell | 20 | 80 | — |
| 12 | linear core/X-linked shell | 20 | 80 | — |
| 13 | linear core/X-linked shell | 20 | 80 | — |
| 14 | linear core/X-linked shell | 20 | 80 | — |
| 15 | linear core/X-linked $2^{nd}$ stage/X-linked $3^{rd}$ stage | 10 | 10 | 80 |
| 16 | linear core/X-linked shell | 20 | 80 | — |
| 17 | linear core/X-linked shell | 20 | 80 | — |
| 18 | linear core/X-linked shell | 20 | 80 | — |
| 19 | linear core/X-linked shell | 20 | 80 | — |

[1]X-linked = crosslinked

Example 20

The staged core-shell polymers of Examples 1, 2, 3a, 6, 9b, 12, and 18 are separately formulated into a clear body wash cleansing composition comprising a blend of an anionic and amphoteric surfactant. The formulation components are set forth in Table 2. Each component (except component nos. 12, 13, and 14) is added to a mixing vessel in the order listed in the table. Components 12, 13, and 14 are formulated into the body wash samples during the testing procedure described below. The solubilizer (component 8) and fragrance (component 9) are premixed before addition to the vessel. The components are blended under mild agitation until a homogeneous body wash master batch formulation is obtained. Control polymers C-1, C-2, and C-3 (30% active polymer solids) are identically formulated as above. The initial pH of each formulation is measured and recorded (Table 3).

TABLE 2

| (Clear Body Wash Formulation) | | | |
|---|---|---|---|
| | Component | Amount (wt. %) | Function |
| 1 | D.I. Water | q.s. to 100 | Diluent |
| 2 | Polymer (30% active polymer solids) | 8.00 | Rheology Modifier |
| 3 | Sulfochem ™ ES-2 CWK Surfactant (26% active) | 40.00 | Detersive Surfactant |
| 4 | Chembetaine ™ CAD Surfactant (35% active) | 6.70 | Amphoteric Surfactant |
| 5 | Merquat ® Plus Polymer (10% active) | 2.10 | Conditioning Polymer |
| 6 | Tetrasodium EDTA | 0.05 | Chelating Agent |
| 7 | Phenonip ® | 0.50 | Antibacterial |
| 8 | Tween 20 | 0.50 | Fragrance Solubilizer |
| 9 | Fragrance | 0.50 | Fragrance |
| 10 | FD&C Blue No. 1 | 1.85 | Dye |
| 11 | FD&C Yellow No. 6 | 0.85 | Dye |
| 12 | NaOH (18% aqueous wt./wt.) | q.s. to pH | pH adjusting agent |
| 13 | Citric Acid (50% aqueous wt./wt.) | q.s. to pH | pH adjusting agent |
| 14 | Lipopearl ™ 0293 Beads | 1.0 | Vitamin E Delivery Beads |

The pH of each of the body wash master batch formulations is then sequentially increased with NaOH (component 12) to pH values of approximately 6.0 and 6.5, respectively, and then sequentially reduced (via back-acid addition) with citric acid (component 13) to pH values of approximately 6.0, 5.5, and 4.5, respectively. At each pH value, 100 g and 20 g aliquots of each master batch body wash formulation is transferred into 4 oz. jars and 6 dram vials, respectively, and centrifuged to remove any entrained air bubbles. The sample jars and vials containing the centrifuged formulations are capped and held for 24 hrs. after which rheology and clarity property measurements are made. Viscosity and yield value measurements are carried out on the 100 g samples and turbidity measurements are completed on the 20 g samples. The data is presented in Table 3.

TABLE 3

| (Viscosity and Clarity Performance of Body Wash Formulation) | | | | | | | | | | | |
|---|---|---|---|---|---|---|---|---|---|---|---|
| Target pH | Polymer | C-1 | C-2 | C-3 | 1 | 2 | 3a | 6 | 9a | 12 | 18 |
| Initial pH | pH (actual) | 5.45 | 5.55 | 5.53 | 5.36 | 5.40 | 5.53 | 5.47 | 5.44 | 5.38 | 5.46 |
| | Viscosity (mPa · s) | 2,060 | 2,330 | 3,870 | 4,100 | 3,950 | 4,000 | 3,940 | 3,430 | 3,750 | 3,720 |
| | Yield Value (dyn/cm$^2$) | 36 | 14 | 104 | 236 | 142 | 98 | 170 | 148 | 94 | 146 |
| | Turbidity (NTU) | 70.1 | 12.3 | 33 | 156 | 28.1 | 21.6 | 29.4 | 75 | 13.7 | 29.4 |
| | | | | | add base | | | | | | |
| 6.0 | pH (actual) | 6.04 | 6.06 | 6.04 | 6.02 | 6.03 | 6.07 | 6.11 | 5.98 | 6.08 | 6.01 |
| | Viscosity (mPa · s) | 1,180 | 810 | 2,920 | 4,700 | 3,180 | 2,910 | 3,200 | 3,250 | 2,500 | 2,920 |

TABLE 3-continued (Viscosity and Clarity Performance of Body Wash Formulation)

| Target pH | Polymer | C-1 | C-2 | C-3 | 1 | 2 | 3a | 6 | 9a | 12 | 18 |
|---|---|---|---|---|---|---|---|---|---|---|---|
| | Yield Value (dyn/cm$^2$) | 12 | 4 | 82 | 260 | 118 | 60 | 132 | 132 | 66 | 114 |
| | Turbidity (NTU) | 42.5 | 5.75 | 22.1 | 29.0 | 16.3 | 11.7 | 16.6 | 46.1 | 10.1 | 19.1 |
| 6.5 | pH (actual) | 6.55 | 6.56 | 6.53 | 6.53 | 6.53 | 6.58 | 6.61 | 6.53 | 6.63 | 6.53 |
| | Viscosity (mPa · s) | 1,700 | 1,080 | 2,880 | 3,900 | 3,170 | 3,600 | 3,050 | 3,230 | 3,220 | 2,620 |
| | Yield Value (dyn/cm$^2$) | 10 | 6 | 48 | 128 | 74 | 40 | 74 | 62 | 42 | 56 |
| | Turbidity (NTU) | 13.5 | 5.83 | 8.68 | 6.63 | 6.10 | 8.40 | 7.14 | 45.2 | 7.34 | 12.40 |
| | | | | | add acid | | | | | | |
| 6.0 | pH (actual) | 6.03 | 6.03 | 6.08 | 5.93 | 5.99 | 6.09 | 6.09 | 6.04 | 6.11 | 6.02 |
| | Viscosity (mPa · s) | 1,700 | 1,080 | 2,890 | 5,700 | 3,610 | 3,430 | 3,680 | 3,580 | 2,930 | 3,340 |
| | Yield Value (dyn/cm$^2$) | 18 | 4 | 78 | 308 | 132 | 66 | 148 | 114 | 70 | 122 |
| | Turbidity (NTU) | 43.6 | 5.83 | 23.0 | 36.3 | 17.6 | 12.2 | 18.3 | 25.6 | 11.5 | 19.4 |
| 5.5 | pH (actual) | 5.55 | 5.53 | 5.60 | 5.50 | 5.48 | 5.45 | 5.49 | 5.52 | 5.61 | 5.51 |
| | Viscosity (mPa · s) | 2,970 | 3,600 | 3,930 | 6,600 | 4,900 | 4,960 | 4,950 | 4,760 | 4,020 | 4,120 |
| | Yield Value (dyn/cm$^2$) | 28 | 14 | 106 | 348 | 162 | 90 | 194 | 156 | 98 | 158 |
| | Turbidity (NTU) | 52.7 | 6.46 | 31.3 | 37.7 | 16.8 | 13.4 | 18.7 | 24.6 | 15 | 24.3 |
| 4.5 | pH (actual) | 4.59 | 4.55 | 4.60 | 4.52 | 4.51 | 4.62 | 4.45 | 4.55 | 4.60 | 4.55 |
| | Viscosity (mPa · s) | 4,020 | 5,700 | 5,100 | 8,050 | 6,000 | 6,050 | 6,250 | 5,900 | 5,750 | 5,050 |
| | Yield Value (dyn/cm$^2$) | 42 | 28 | 130 | 412 | 200 | 112 | 238 | 192 | 136 | 184 |
| | Turbidity (NTU) | 53.1 | 3.54 | 27.3 | 30.0 | 12.1 | 7.42 | 15.1 | 24.9 | 9 | 20.2 |

From the combined rheology and turbidity data it is evident that body wash compositions formulated with the staged linear core/crosslinked shell polymers of the invention exhibit superior combined rheology and turbidity properties (at pH≤6) when compared to control polymer C-1 having a crosslinked core and linear shell or the single stage polymers C-2 and C-3 which are linear and crosslinked, respectively. The polymers of the invention demonstrate overall better yield values indicating better suspension properties.

Example 21

The body wash samples of Example 20 that contain Polymer Nos. C-1, C-2, 1, 2, and 6 at pH 4.5 (in 6 dram vials), are subsequently evaluated for their ability to suspend cosmetic beads at 45° C. for a duration of 12 weeks. Bath gel formulations containing control polymers C-1 and C-2 failed after 2 days in the aging oven. Polymers 1, 2, and 6 passed following 12 weeks in the aging oven.

TABLE 4

(12 Week Suspension Stability)

| Polymer No. | Pass | Fail |
|---|---|---|
| C-1 | No | Yes |
| C-2 | No | Yes |
| 1 | Yes | No |
| 2 | Yes | No |
| 6 | Yes | No |

Example 22

Physical blends of single stage crosslinked control polymer C-3 and linear control polymer C-2 and are prepared in the following blend ratios (C-3/C-2 wt./wt.): 80:20; 50:50; 40:60; and 20:80. The blends are prepared from polymer emulsions equivalent to a use level of 2.4 wt. % active polymer solids. Each blend is formulated into body wash master batches in accordance with the procedures, components and amounts set forth in Example 20. Body wash master batches formulated with 100:0 C-3 polymer and 0:100 C-2 polymer are included for comparative purposes. The pH of each master batch blend is sequentially increased with NaOH to pH values of approximately 6.0 and 6.5, respectively, and then sequentially reduced with citric acid (via back-acid addition) to pH values of approximately 6.0, 5.5, and 4.5, respectively. At each pH value, 100 g and 20 g aliquots of each master batch body wash formulation is transferred into 4 oz. jars and 6 dram vials, respectively, and centrifuged to remove any entrained air bubbles. The sample jars and vials containing the centrifuged formulations are capped and held for 24 hrs. after which rheology and clarity property measurements are made. The viscosity, yield value, and turbidity properties for base addition to pH 6.0 and acid addition to pH 6.0, 5.5, and 4.5 are measured and recorded in Table 5 (data for base addition to pH 6.5 is not recorded).

TABLE 5

(Viscosity and Clarity Performance of Polymer Blends)

| Target | | Polymer Blend Ratios (C-3:C-2 wt/wt.) | | | | | |
|---|---|---|---|---|---|---|---|
| pH | Properties | 100:0 | 80:20 | 50:50 | 40:60 | 20:80 | 0:100 |
| Initial | pH (initial) | 5.53 | 5.52 | 5.48 | 5.48 | 5.53 | 5.55 |
| | Viscosity (mPa · s) | 3,870 | 3,090 | 2,580 | 2,510 | 2,450 | 2,330 |
| | Yield Value (dyn/cm$^2$) | 104 | 58 | 32 | 26 | 18 | 14 |
| | Turbidity (NTU) | 32.5 | 32.3 | 28.6 | 26.3 | 19.9 | 12.3 |
| | | | add base | | | | |
| 6.0 | pH (actual) | 6.04 | 6.04 | 6.00 | 5.99 | 5.98 | 6.06 |
| | Viscosity (mPa · s) | 2,920 | 2,200 | 1,470 | 1,240 | 1,010 | 810 |
| | Yield Value (dyn/cm$^2$) | 82 | 36 | 14 | 8 | 6 | 4 |
| | Turbidity (NTU) | 22.1 | 25.1 | 22.2 | 20.3 | 15.0 | 5.75 |
| 6.5 | | Properties not measured | | | | | |
| | | | add acid | | | | |
| 6.0 | pH (actual) | 6.08 | 6.01 | 5.96 | 6.02 | 5.98 | 6.03 |
| | Viscosity (mPa · s) | 2,890 | 2,160 | 1,900 | 1,540 | 1,290 | 1,080 |
| | Yield Value (dyn/cm$^2$) | 78 | 32 | 12 | 10 | 10 | 4 |
| | Turbidity (NTU) | 23.0 | 29.3 | 26.0 | 20.9 | 16.4 | 5.83 |
| 5.5 | pH (actual) | 5.60 | 5.52 | 5.51 | 5.51 | 5.48 | 5.53 |
| | Viscosity (mPa · s) | 3,930 | 3,280 | 3,250 | 3,600 | 3,780 | 3,600 |
| | Yield Value (dyn/cm$^2$) | 106 | 50 | 24 | 28 | 22 | 14 |
| | Turbidity (NTU) | 31.3 | 35.1 | 27.3 | 24.8 | 17.9 | 6.46 |
| 4.5 | pH (actual) | 4.60 | 4.51 | 4.42 | 4.44 | 4.46 | 4.55 |
| | Viscosity (mPa · s) | 5,100 | 4,150 | 4,390 | 5,910 | 5,850 | 5,700 |
| | Yield Value (dyn/cm$^2$) | 130 | 66 | 36 | 30 | 20 | 28 |
| | Turbidity (NTU) | 27.3 | 36.9 | 31.6 | 28.4 | 20.3 | 3.54 |

When compared to the staged linear core/crosslinked shell polymers in Table 3 above, the data show that physical blends of linear and crosslinked polymers have inferior combined rheology and turbidity properties across the pH values tested in body wash compositions.

Example 23

The staged core-shell polymers of Examples 1, 2, 4, 7, 8, 9, and 10 are each formulated into a clear bath gel cleansing composition comprising a sodium based anionic surfactant and an amphoteric surfactant. A food grade preservative, sodium benzoate, is added in place of alkyl parabens. The formulation components are set forth in Table 6. Components 1 through 11 are added to a vessel with mixing in the order listed in the table. Components 12, 13, and 14 are added to the bath gel formulations during the testing procedure described below. The fragrance (component 7) and solubilizer (component 8) are premixed before addition to the vessel. The components are blended under gentle agitation until a homogeneous bath gel master batch mixture is obtained. Bath gel master batches containing commercially available control polymers, C-4 (Rheocare™ TTA) and C-5 (Carbopol® Aqua SF-1) are identically formulated (2.4 wt. % active polymer solids) as above.

TABLE 6

(Clear Bath Gel Formulated With Food Grade Preservative)

| | Component | Amount (wt. %) | Function |
|---|---|---|---|
| 1 | D.I. Water | q.s. to 100 | Diluent |
| 2 | Polymer (30% active polymer solids) | 8.00 | Rheology Modifier |
| 3 | Sulfochem ™ ES-2 CWK Surfactant (28% active) | 40.00 | Detersive Surfactant |

TABLE 6-continued (Clear Bath Gel Formulated With Food Grade Preservative)

| | Component | Amount (wt. %) | Function |
|---|---|---|---|
| 4 | Chembetaine ™ CAD Surfactant (35% active) | 6.70 | Amphoteric Surfactant |
| 5 | Merquat ® Plus Polymer | 2.10 | Conditioning Polymer |
| 6 | Tetrasodium EDTA | 0.05 | Chelating Agent |
| 7 | Fragrance | 0.50 | Fragrance |
| 8 | Tween 20 | 0.50 | Fragrance Solubilizer |
| 9 | FD&C Blue No. 1 | 1.85 | Dye |
| 10 | FD&C Yellow No. 6 | 0.85 | Dye |
| 11 | NaOH (18%) | q.s. to pH 6.5 | pH Adjusting Agent |
| 12 | Citric Acid (50% aqueous wt./wt.) | q.s. to pH | pH Adjusting Agent |
| 13 | Sodium Benzoate | 0.50 | Preservative |
| 14 | Lipopearl ™ Beads | 1.0 | Vitamin E Delivery Vehicle |

The pH of each master batch formulation is adjusted to 6.5 with NaOH (component 11), and then sequentially reduced with citric acid (component 12) to pH values of approximately 5.5, 5.0, and 4.0, respectively. Sodium benzoate (component 13) is added to each sample adjusted to pH 5.0 before additional citric acid is added to achieve the final pH value of 4.0. At each pH value, 100 g and 20 g aliquots of each master batch bath gel formulation is transferred into 4 oz. jars and 6 dram vials, respectively, and centrifuged to remove any entrained air bubbles. The sample jars and vials containing the centrifuged aliquots are capped and held for 24 hrs. at ambient room temperature, after which rheology and clarity property measurements are made. The viscosity, yield value, and turbidity properties for each pH adjusted sample are measured and recorded in Table 7.

TABLE 7

| (Viscosity and Clarity Performance of Bath Gel Formulation) | | | | | | | | | |
|---|---|---|---|---|---|---|---|---|---|
| | Polymer No. | | | | | | | | |
| Properties | 1 | 2 | 4 | 7 | 8 | 9 | 10 | C-4 | C-5 |
| Turbidity (NTU) @ pH 6.5 | 3.0 | 4.9 | 5.3 | 2.88 | 5.36 | 2.03 | 4.11 | 22.9 | 12.0 |
| Turbidity (NTU) @ pH 5.5 | 33.0 | 13 | 17 | 14.1 | 13.2 | 12.8 | 41.1 | 96.2 | 67 |
| Turbidity (NTU) @ pH 5.0 | 30.0 | 12 | 16 | 14.7 | 13.1 | 12.5 | 11.1 | 96.0 | 74 |
| Turbidity (NTU) @ pH 4.0 | 31.0 | 12.7 | 17 | 19.5 | 12.2 | 15 | 14.2 | 120 | 89 |
| Viscosity (mPa · s) @ pH 4.0 | 10,980 | 9,000 | 10,720 | 5,140 | 5,620 | 8,500 | 6,460 | 19,600 | 9,660 |
| Yield Value ($dyn/cm^2$) @ pH 4.0 | 476 | 220 | 368 | 86 | 168 | 236 | 142 | 620 | 508 |

Into the formulation samples that are back-acid treated to pH 4.0, Lipopearl™ beads 1.0 wt. %, based on the weight of the total composition) are added. The samples are tested pursuant to the suspension testing procedure protocol described above.

The staged core-shell acrylate polymers of this invention deliver excellent clarity at pH values below 6 in sodium based surfactant formulations containing an acid preservative. In contrast, the commercial Control Polymers C-4 and C-5 are hazy or opaque (higher NTU values) at pH values below 6 in the same formulation. All formulations (including the commercial control polymers C-4 and C-5) have good bead suspension properties at 45° C. for 12 weeks.

Example 24

The staged core-shell polymers of Examples 1, 2, and 4 are separately formulated into a clear conditioning shampoo composition comprising an ammonium based anionic surfactant, an amphoteric surfactant and a subsequently added pearlizing agent. A food grade preservative, sodium benzoate, is utilized as a preservative. Commercially available Control Polymers, C-4 (Rheocare™ TTA) and C-5 (Carbopol® Aqua SF-1) are identically formulated (1.5 wt. % active polymer solids). The formulation is prepared from the components listed in Table 8.

TABLE 8

| (Clear Conditioning Shampoo With Added Pearlizing Agent) | | | |
|---|---|---|---|
| | Component | Amount (wt. %) | Function |
| 1 | D.I. Water | q.s. to 100 | Diluent |
| 2 | Polymer (30% active polymer solids) | 5.00 | Rheology Modifier |
| 3 | Sulfochem ™ ALS-K Surfactant (30% active) | 25.00 | Detersive Surfactant |
| 4 | Sulfochem ™ EA-3 Surfactant (27% active) | 15.00 | Detersive Surfactant |
| 5 | Chemonic ™ SI-7 Surfactant | 4.00 | Non-Ionic Surfactant |
| 6 | Dow Corning ® 2-8194 Silicone Microemulsion | 2.00 | Conditioning Agent |

TABLE 8-continued

| (Clear Conditioning Shampoo With Added Pearlizing Agent) | | | |
|---|---|---|---|
| | Component | Amount (wt. %) | Function |
| 7 | Fragrance | 0.50 | Fragrance |
| 8 | NaOH (18% aqueous wt./wt.) | q.s. to pH 6.5 | pH Adjusting Agent |
| 9 | Citric Acid (50% aqueous wt./wt.) | q.s. to pH 4.5 | pH Adjusting Agent |
| 10 | Sodium Benzoate | 0.50 | Preservative |
| 11 | D.I. Water | 10.00 | Diluent |
| 12 | Mica (gold tinted) | 0.20 | Pearlizing Agent |

Components 1 through 4 are added to a vessel in the order listed in the table and mixed under slow agitation until homogeneous. The pH of each formulation is adjusted to approximately 6.5 with NaOH (component 8), and then components 5 to 7 are added to each batch and homogeneously mixed. The pH of each batch is then sequentially reduced with citric acid (component 9) to pH values of approximately 5.5, 5.0, and 4.0, respectively. Sodium benzoate (component 10) is added to each sample at pH 5.0 before additional citric acid is added to achieve a final pH value of 4.0. At each pH value, a 20 g sample of each batch formulation is transferred into separate 6 dram vials. The vials are capped, centrifuged to remove any trapped air bubbles contained in the formulation and held at ambient room temperature for 24 hrs., after which turbidity property measurements are taken. In addition, viscosity and yield properties are measured for the final sample (pH 4.0). The data is presented in Table 9.

TABLE 9

| (Viscosity and Clarity Performance of Conditioning Shampoo) | | | | | |
|---|---|---|---|---|---|
| | Polymer No. | | | | |
| Properties | 1 | 2 | 4 | C-4 | C-5 |
| Turbidity (NTU) @ pH 6.5 | 220 | 143 | 121 | 193 | 206 |
| Turbidity (NTU) @ pH 5.5 | 36 | 30 | 15 | 117 | 38 |

TABLE 9-continued (Viscosity and Clarity Performance of Conditioning Shampoo)

| Properties | Polymer No. 1 | 2 | 4 | C-4 | C-5 |
|---|---|---|---|---|---|
| Turbidity (NTU) @ pH 5.0 | 42 | 29 | 17 | 126 | 58 |
| Turbidity (NTU) @ pH 4.0 | 40 | 18 | 14 | 100 | 61 |
| Viscosity (mPa · s) @ pH 4.0 | 2,670 | 2,940 | 2,960 | 2,900 | 3,350 |
| Yield Value (dyn/cm$^2$) @ pH 4.0 | 72 | 52 | 66 | 56 | 100 |

To demonstrate that the polymers of the invention can stabilize a pearlized conditioning shampoo, a pearlizing agent (component 12) is added to D.I. water (component 11) and uniformly dispersed. The dispersion is then added to the conditioning shampoo samples previously back-acid adjusted to pH 4.0 and mixed until a homogeneous pearlized formulation is attained. Each of the pearlized conditioning shampoo samples are tested and evaluated pursuant to the suspension testing procedure protocol described above.

The staged core-shell acrylate polymers deliver excellent clarity properties at pH values below 6 in ammonium based surfactant formulations containing silicone microemulsion. In contrast, all the commercial control polymers (C-4, and C-5) are either hazy or opaque (higher NTU values) at pH values below 6 in the same formulation. All formulations exhibit good pearlizing agent suspension at 45° C. for 3 months.

Example 25

The staged core-shell polymers of Examples 2 and 4 are formulated into a pearlized conditioning shampoo composition comprising a cationic polymer conditioning agent and a silicone conditioning agent. A food grade preservative, sodium benzoate, is utilized as a preservative. The formulation is prepared from the components listed in Table 10.

TABLE 10

(Pearlized Conditioning Shampoo)

| | Component | Amount (wt. %) | Function |
|---|---|---|---|
| 1 | D.I. Water | q.s. to 100 | Diluent |
| 2 | Polymer (30% active polymer solids) | 5.00 | Rheology Modifier |
| 3 | Sulfochem ™ ALSK Surfactant (30% active) | 25.00 | Detersive Surfactant |
| 4 | Sulfochem ™ EA-3 Surfactant (27% active) | 15.00 | Detersive Surfactant |
| 5 | Jaguar Excel (2.0% solution) | 15.00 | Cationic Conditioning Agent |
| 6 | Chemonic ™ SI-7 Surfactant | 4.00 | Non-Ionic Surfactant |
| 7 | Dow Corning ® 2-8194 Silicone Microemulsion | 2.00 | Conditioning Agent |
| 8 | Fragrance | 0.50 | Fragrance |
| 9 | NaOH (18% aqueous wt./wt.) | q.s. to pH 6.5 | pH Adjusting Agent |
| 10 | Citric Acid (50% aqueous wt./wt.) | q.s. to pH 4.0 | pH Adjusting Agent |
| 11 | Sodium Benzoate | 0.50 | Preservative |
| 12 | D.I. Water | 10.00 | Diluent |
| 13 | Mica (gold tinted) | 0.20 | Pearlizing Agent |

The components are formulated as set forth in Example 24 above, except that a cationic conditioning polymer (component 5) is utilized in addition to the silicone conditioning agent (component 7). Commercially available Control Polymer, C-5 (Carbopol® Aqua SF-1), is identically formulated (1.5 wt. % active polymer solids) as in Example 24. The pH of the polymer formulations are immediately adjusted with NaOH (component 9) to 6.5, and then sequentially downward with citric acid (component 10) to 5.5, 5.0 and 4.0 as in the previous example, except that 0.5 wt. % NaCl (based on the weight of the total formulation components) is added to one set of the samples adjusted to pH 4.0. For comparison, a second set of samples is evaluated without added NaCl. Viscosity and turbidity values are measured after pH adjustment. The viscosity and clarity performance data for each of the evaluated samples is set forth in Table 11.

TABLE 11

(Viscosity and Clarity Performance)

| Properties | 2 | 4 | C-5 |
|---|---|---|---|
| Turbidity (NTU) @ pH 6.5 | 194.0 | 200.0 | 353.0 |
| Turbidity (NTU) @ pH 5.5 | 74.2 | 62.1 | 179.0 |
| Turbidity (NTU) @ pH 5.0 | 69.1 | 57.7 | 181.0 |
| Turbidity (NTU) @ pH 4.0 (NaCl) | 47.2 | 49.2 | 128.0 |
| Viscosity (mPa · s) @ pH 6.5 | 4,870 | 4,350 | 3,500 |
| Viscosity (mPa · s) @ pH 4.0 (w/o NaCl) | 8,600 | 7,500 | 7,180 |
| Viscosity (mPa · s) @ pH 4.0 (with NaCl) | 12,000 | 11,450 | 12,060 |

To demonstrate that the polymers of the invention can stabilize a pearlized conditioning shampoo, a pearlizing agent (component 13) is added to D.I. water (component 12) and uniformly dispersed. The dispersion is then added to the conditioning shampoo samples previously back-acid adjusted to pH 4.0 and mixed until a homogeneous pearlized formulation is attained. Each of the pearlized conditioning shampoo samples are tested and evaluated pursuant to the suspension testing procedure protocol described above.

The staged core-shell acrylate polymers of the invention deliver excellent clarity properties at pH values below 6 in ammonium based surfactant formulations containing a conditioning package comprising a cationic polymer and a silicone conditioning agent. The polymers of the invention maintain good clarity properties even after the addition of an alkali metal salt such as NaCl. The commercial control polymer (C-5) while delivering good rheological properties provides formulations that are either hazy or opaque (higher NTU values) at pH values below 6. All formulations exhibit good pearlizing agent suspension at 45° C. for 3 months.

The cationic polymer can be replaced by and/or blended with other synthetic monomeric or polymeric cationic conditioners and/or the amount present in the formulation can be adjusted to maximize synergy with the inventive polymers. Also, the silicone microemulsion conditioning agent can be substituted with larger sized particles in the emulsion if desired.

Example 26

A soap based shower gel composition is formulated from the components are set forth in the Table 12.

TABLE 12

(Soap Based Shower Gel)

| | | Component | Amount (wt. %) | Function |
|---|---|---|---|---|
| Part A | 1 | Deionized Water | q.s. to 100 | Diluent |
| | 2 | Potassium Hydroxide (87.5% aqueous wt./wt.) | 6.60 | Neutralizer |
| Part B | 3 | Deionized Water | q.s. to 100 | Diluent |
| | 4 | Glycerin | 6.00 | Humectant |
| | 5 | Lauric Acid | 12.00 | Fatty Acid |
| | 6 | Myristic Acid (1499) | 6.50 | Fatty Acid |
| | 7 | Palmitic Acid (1698) | 1.50 | Fatty Acid |
| | 8 | Polymer No. 2 (30% active polymer solids) | 7.0 | Rheology Modifier |
| Part C | 9 | Mineral Oil, Type #26 (24-28 mm2/s) | 10.00 | Emollient |
| | 10 | Propylene Glycol | 2.00 | Humectant |
| | 11 | Neolone ® 950 | 0.05 | Preservative |

Part A is prepared by dissolving potassium hydroxide in D.I. water and heating the composition to 80° C. Part B is separately prepared by adding glycerin and the fatty acids (components 5, 6, and 7) to D.I. water and mixing until the fatty acids fully melt. Once the fatty acids melt and are homogeneously mixed, polymer no. 2 is added to the mixture. Part A is slowly added to Part B under agitation while the temperature is maintained at 80° C. The Part AB composition is mixed for 30 to 60 minutes. Upon attaining a homogeneous mixture, the Part AB composition is allowed to cool at ambient room temperature (20-21° C.). Mineral oil (component 9) is added to the AB composition at a temperature of about 60-70° C. Upon further cooling to 40° C., components 10 and 11 are added and uniformly mixed into the formulation. The formulation is allowed to cool under gentle agitation until ambient room temperature is reached. After 24 hrs. the following physical data is recorded: pH=9.4; viscosity (spindle no. 4 @ 20 rpm)=6000 mPa·s; and yield value=60 dyn/$cm^2$.

While this example exemplifies the in situ saponification of the fatty acid(s) with a base, a pre-neutralized fatty acid salt can also be employed in the formulation of the cleansing formulation. In addition, high clarity soap based shower gel can also be made without the mineral oil component.

Example 27

A pearlized soap/surfactant blend based shower gel composition is formulated from the components are set forth in the Table 13.

TABLE 13

(Soap/Surfactant Blend Based Shower Gel)

| | | Component | Amount (wt. %) | Function |
|---|---|---|---|---|
| Part A | 1 | Deionized Water | q.s. to 100 | Diluent |
| | 2 | Potassium Hydroxide (91.5% aqueous wt./wt.) | 4.35 | Neutralizer |
| Part B | 3 | Deionized Water | 25.42 | Diluent |
| | 4 | Glycerin | 8.00 | Humectant |
| | 5 | Lauric Acid | 7.20 | Fatty Acid |
| | 6 | Myristic Acid | 2.40 | Fatty Acid |
| | 7 | Palmitic Acid | 2.40 | Fatty Acid |
| | 8 | Polymer No. 2 (30% active polymer solids) | 7.0 | Rheology Modifier |
| Part C | 9 | Sulfochem ES-2K (26.1% active) | 15.00 | Detersive Surfactant |
| | 10 | Chembetaine ™ CAD (35% active) | 12.88 | Amphoteric Surfactant |
| | 11 | Neolone ® 950 | 0.05 | Preservative |
| | 12 | Liposphere ™ 0031 Beads | 0.15 | Cosmetic Bead Containing Moisturizer |
| | 13 | Lipopearl ™ 0091 Beads | 0.15 | Cosmetic Bead Containing Moisturizer |
| | 14 | Citric Acid (50% aqueous wt./wt.) | 0.5 | pH Adjusting Agent |

Part A is prepared by dissolving potassium hydroxide in D.I. water and heating the composition to 80° C. Part B is separately prepared by adding glycerin and polymer no. 2 to D.I. water under mixing. The fatty acids (components 5, 6, and 7) are added to Part B, which is heated to 80° C. and mixed until the fatty acids fully melt. Once the fatty acids melt and are homogeneously mixed, Part A is slowly added to Part B under agitation while maintaining the temperature at 80° C. The Part AB composition is mixed for 30 to 60 minutes. Upon attaining a homogeneous mixture, the Part AB composition is allowed to cool at ambient room temperature (20-21° C.). The surfactant package (components 9 and 10) is added in the order listed to the AB composition under agitation and mixed until uniform. Upon further cooling to 40° C., components 11 through 14 are added in order and uniformly mixed into the formulation. The formulation is allowed to cool under gentle agitation until ambient room temperature is reached. After 24 hrs. the following physical data is recorded: pH=9.5; viscosity (spindle no. 4 @ 20 rpm)=2500 mPa·s; and turbidity=7.7 NTU.

Example 28

A high oil containing moisturizing body wash containing a food preservative is formulated from the components and procedure set forth below. Commercially available Control Polymers, C-4 (Rheocare™ TTA) and C-5 (Carbopol® Aqua SF-1) are identically formulated (2 wt. % active polymer solids). A formulation blank (no active rheology modifying polymer) is also prepared.

TABLE 14

(Moisturizing Body Wash)

| | | Component | Amount (wt. %) | Function |
|---|---|---|---|---|
| Part A | 1 | Deionized Water | q.s. to 100 | Diluent |
| | 2 | Versene ™ 220 (Tetrasodium EDTA) | 0.05 | Chelating Agent |
| | 3 | Sulfochem ™ ALS Surfactant (30% active), | 15.00 | Detersive Surfactant |
| | 4 | Sulfochem ™* EA-3 (27% active) | 25.00 | Detersive Surfactant |
| Part B | 5 | Florasun ® 90 Sunflower Oil | 18.00 | Conditioner/ Emollient |
| | 6 | Polymer No. 2 (30% active polymer solids) | 6.60 | Rheology Modifier |

TABLE 14-continued

| (Moisturizing Body Wash) | | | | |
|---|---|---|---|---|
| | | Component | Amount (wt. %) | Function |
| Part C | 7 | N-Hance ® 3000 | 0.30 | Cationic Conditioner |
| | 8 | Glycerine 99.7% USP | 5.00 | Humectant |
| Part D | 9 | NaOH (18% aqueous wt./wt.) | 1.50 | pH Adjusting Agent |
| Part E | 10 | Sodium Benzoate | 0.50 | Preservative |
| | 11 | Citric Acid (100%) | 0.25 | pH Adjusting Agent |
| | 12 | Chembetaine ™ CGF (35% active) | 5.0 | Amphoteric Surfactant |

The body wash is formulated in accordance with the following procedure:

1) Combine Part A components and mix until uniform. Adjust mixing speed to keep foaming to a minimum;

2) Add Part B components in the listed order to Part A with mixing and mix until uniform;

3) In a separate vessel, pre-mix Part C components and add to Part AB and mix until uniform;

4) Add Part D (NaOH) to Part ABC and increase mixing speed as needed to maintain a good vortex; and 5) Add Part E components one at a time in the order listed to Part ABCD with good mixing in between additions. Increase mixing speed as needed to maintain mixing vortex.

The high oil content body wash formulations are evaluated for Brookfield viscosity (spindle no. 6 @ 20 rpm), and visually evaluated for texture and phase separation (after 1 week, 2 weeks, and 8 weeks). The results are set forth in the table below. Separation is herein defined as the visible existence of 2 or more distinct layers or phases of any component in the formulation, including but not limited to insoluble matter, soluble matter, oily substances, and the like. For the phase stability ranking: (0=phase separation; 1=no phase separation).

TABLE 15

| Polymer No. | Active Polymer Solids | Viscosity (mPa · s) | Texture | Phase Stability 1 wk. | 2 wk. | 8 wk. |
|---|---|---|---|---|---|---|
| Blank | 0 | 19,590 | — | 0 | 0 | 0 |
| C-4 | 2.0 | 11,440 | Smooth | 1 | 1 | 1 |
| C-5 | 2.0 | 13,360 | Smooth | 1 | 1 | 1 |
| 2 | 2.0 | 14,910 | Smooth | 1 | 1 | 1 |

Example 29

A sulfate free bath gel is formulated from the components listed in the table below. Polymer Nos. 2 and 4 are utilized as the rheology modifying component. Commercially available Control C-5 is identically formulated for comparison purposes.

TABLE 16

| (Sulfate Free Bath Gel) | | | |
|---|---|---|---|
| | Components | Amount (wt. %) | Function |
| 1 | Deionized Water | q.s. to 100 | Diluent |

TABLE 16-continued

| (Sulfate Free Bath Gel) | | | |
|---|---|---|---|
| | Components | Amount (wt. %) | Function |
| 2 | Polymer No. 2 (30% active polymer solids) | 8.0 | Rheology Modifier |
| 3 | NaOH (18% aqueous wt./wt.) | q.s. to pH | pH Adjusting Agent |
| 4 | Chemoryl ™ SFB-10SK Surfactant Blend (32% active) | 30.0 | Mild Detersive Surfactant Blend (sulfate free) |
| 5 | Cocamidopropyl Betaine (38% active) | 8.0 | Amphoteric Detersive Surfactant |
| 6 | Sodium Benzoate | 0.5 | Preservative |
| 7 | Citric Acid (50% aqueous wt./wt.) | q.s. to pH | pH Adjusting Agent |

The test polymer (component 2) is added to D.I. water (component 1) in a glass beaker and mixed gently. The pH of the formulation is adjusted with NaOH (component 3) to 6.5 and then the surfactants (component 4) and (component 5) are added to the contents of the beaker and mixed until homogeneous. An aliquot of the bath gel formulation is transferred to a 6 dram vial for pH and turbidity measurements. The pH of the bath gel contents of the beaker is adjusted to 5.5 with citric acid (component 7). An aliquot of the pH adjusted bath gel composition is transferred to a 6 dram vial for turbidity determination. The pH of the bath gel in the beaker is again adjusted with citric acid (component 7) to 5.0 and another aliquot of the pH adjusted bath gel is transferred to a 6 dram vial for turbidity testing. The recipe amount of sodium benzoate is added to the bath gel in the beaker (previously adjusted to pH 5.0), and a final pH adjustment is made with citric acid (component 7) to achieve a pH of 4.0. After this final pH adjustment, 24 hrs. viscosity properties and yield value properties are measured. The data for rheology and turbidity measurements are reported in Table 17.

TABLE 17

| Properties | Polymer No. 2 | 4 | C-5 |
|---|---|---|---|
| Turbidity (NTU) @ pH 6.5 | 5.65 | 8.59 | 52.1 |
| Turbidity (NTU) @ pH 5.5 | 27.2 | 38.7 | 204 |
| Turbidity (NTU) @ pH 5.0 | 31.6 | 42.7 | 221 |
| Viscosity (mPa · s) @ pH 4.0 | 15,150 | 10,200 | 8,000 |
| Yield Value (dyn/cm$^2$) @ pH 4.0 | 360 | 360 | 380 |

In low pH formulations, the polymers of the invention exhibit significantly better rheology and clarity properties compared to a commercial acrylates copolymer standard.

Example 30

This example demonstrates the formulation of a facial scrub composition containing Polymer No. 2. The formulation components are listed in Table 18.

TABLE 18

| (Facial Scrub) | | | |
|---|---|---|---|
| | Component | Amount (wt. %) | Function |
| 1 | Deionized Water | q.s. to 100 | Diluent |
| 2 | Disodium EDTA | 0.05 | Chelating Agent |

TABLE 18-continued (Facial Scrub)

| | Component | Amount (wt. %) | Function |
|---|---|---|---|
| 3 | Polymer No. 2 (33.6% active polymer solids) | 6.72 | Rheology Modifier |
| 4 | Sulfochem ™AOS Surfactant (40% active), | 7.575 | Detersive Surfactant |
| 5 | NaOH (18% aqueous wt./wt.) | q.s. to pH | pH Adjusting Agent |
| 6 | Chemoryl ™ SFB-10SK Surfactant (32% Active) | 31.70 | Amphoteric Surfactant |
| 7 | Tween 20 | 1.0 | Solubilizer |
| 8 | Lebermuth Fragrance Oil (No. 90-3000-62) | 0.45 | Fragrance |
| 9 | Glucam ™ E-10 Methyl Glucoside | 0.50 | Nonionic Surfactant/ Humectant |
| 10 | Geogard ® Ultra (sodium benzoate) | 1.00 | Preservative |
| 11 | Chembetaine LEC (35% active) | 8.00 | Amphoteric Surfactant |
| 12 | Citric Acid (50% aqueous wt./wt.) | q.s. to pH | pH Adjusting Agent |
| 13 | Florabeads ™ Jojoba 28/60 Sonora Sand | 0.10 | Exfoliating Agent |
| 14 | Florabeads ™ Jojoba 28/60 Gypsy Rose | 0.10 | Exfoliating Agent |

The facial scrub is formulated in accordance with the following procedure:

1) With gentle mixing add disodium EDTA (component 2) to D.I. water (component 1) warmed to 30 to 40° C. until the disodium EDTA is fully dissolved;

2) Add Polymer No. 2 (component 3) to the mixture until fully dispersed and then add the detersive surfactant (component 4) and continue mixing until homogeneous;

3) Under continuous stirring, neutralize the formulation with NaOH (component 5) to raise the pH of the formulation in the range of 6.6 to 6.8;

4) Add the amphoteric surfactant (component 6) and mix until homogeneous;

5) In a separate container pre-blend Polysorbate 20 (component 7) and the fragrance oil (component 8) and add the blend to the formulation and mix until homogeneous;

6) Add the nonionic surfactant/humectant, the preservative, and the amphoteric surfactant (components 9, 10, and 11, respectively) in the order listed and mix until homogeneous;

7) Adjust the pH to 5.3 to 5.4 with citric acid (component 12) and add the exfoliating agents (components 13 and 14) and mix until homogeneous.

Example 31

This example illustrates the formulation of a facial scrub containing the cosmeceutical agent, salicylic acid. The formulation components are listed in Table 19.

TABLE 19

(Facial Scrub)

| | Component | Amount (wt. %) | Function |
|---|---|---|---|
| 1 | Deionized Water | q.s. to 100 | Diluent |
| 2 | Disodium EDTA | 0.050 | Chelating Agent |
| 3 | Polymer No. 2 (33.6% active polymer solids) | 6.72 | Rheology Modifier |
| 4 | Sulfochem ™AOS Surfactant (40% active), | 22.50 | Detersive Surfactant |
| 5 | NaOH (18% aqueous wt./wt.) | q.s. to pH | pH Adjusting Agent |
| 6 | Chembetaine ™ CAD Surfactant (35% active) | 5.70 | Amphoteric Surfactant |
| 7 | Lebermuth Fragrance Oil (No. 50-8001-30) | 0.40 | Fragrance |
| 8 | Deionized Water | 12.53 | Diluent |
| 9 | Zema ™ propanediol | 2.00 | Diluent |
| 10 | Sulfochem ™AOS Surfactant (40% active), | 7.50 | Detersive Surfactant |
| 11 | Salicylic Acid | 2.00 | Cosmeceutical |
| 12 | Chembetaine ™ CAD Surfactant (35% active) | 5.70 | Amphoteric Surfactant |
| 13 | Glucam ™ E-10 Methyl Glucoside | 0.50 | Nonionic Surfactant/ Humectant |
| 14 | Geogard ® Ultra (sodium benzoate) | 1.00 | Preservative |
| 15 | Citric Acid (50% aqueous wt./wt.) | q.s. to pH | pH Adjusting Agent |
| 16 | Unispheres ™ NLT-2312 Cosmetic Beads | 0.20 | Cosmeceutical/ Exfolient |

The facial scrub is formulated as follows:

1) With gentle mixing add disodium EDTA (component 2) to D.I. water (component 1) warmed to 30 to 40° C. until the disodium EDTA is fully dissolved;

2) Add Polymer No. 2 (component 3) to the mixture until fully dispersed and then add the detersive surfactant (component 4) and continue mixing until homogeneous;

3) Under continuous stirring, neutralize the formulation with NaOH (component 5) to raise the pH of the formulation in the range of 6.6 to 6.8;

4) In a separate container pre-blend the amphoteric surfactant (component 6) and the fragrance oil (component 7) and add the pre-blend to the master batch formulation and mix until homogeneous;

5) In a separate vessel pre-blend D.I. water (component 8), propane diol (component 9), anionic surfactant (component 10), salicylic acid (component 11), amphoteric surfactant (component 12) and the nonionic surfactant/humectant component 13) and mix until uniform;

6) Add the pre-blend to the master batch formulation and mix until homogeneous;

7) Add sodium benzoate (component 14) and adjust the pH to 4.0 to 4.4 with citric acid (component 15);

8) Add the exfoliating agent (component 16) and mix until homogeneous.

Example 32

The following example demonstrates a liquid dishwashing cleanser formulated with a polymer of the invention. The formulation components are set forth in Table 20.

TABLE 20

(Liquid Dishwashing Cleanser)

| | Components | Amount (wt. %) | Function |
|---|---|---|---|
| 1 | D.I. Water | q.s. to 100 | Diluent |
| 2 | Polymer No. 2 (2.0 wt. % active solids) | 7.0 | Rheology Modifier |

TABLE 20-continued (Liquid Dishwashing Cleanser)

| | Components | Amount (wt. %) | Function |
|---|---|---|---|
| 3 | Sulfochem ™ SLS Surfactant (30% active) | 37.39 | Surfactant |
| 4 | Sulfochem ™ ES-70 Surfactant (70% active) | 12.05 | Surfactant |
| 5 | Chemoxide ™ CAW Surfactant (30% active) | 3.11 | Surfactant |
| 6 | Geogard ® Ultra (sodium benzoate) | 1.0 | Preservative |
| 7 | NaOH (18% aqueous wt./wt.) | q.s. to pH | pH Adjusting Agent |
| 8 | Citric Acid (50% aqueous wt./wt.) | q.s. to pH | pH Adjusting Agent |

The dish washing liquid is formulated as in accordance with the following procedure:

1) Into a beaker equipped with a magnetic stir bar, add the polymer (component 2) to D.I. water (component 1) and mix under slow agitation (200 rpm);

2) Add surfactants (components 3, 4, and 5) in order listed to the beaker and adjust stirring rate to avoid excessive foam generation;

3) Add preservative (component 6) and mix until uniform and homogeneous;

4) Adjust the pH of the composition with NaOH (component 7) and/or citric acid (component 8) to pH 5.5; and optionally 5) Add fragrance or color, as desired.

Example 33

This example demonstrates that good rheological properties and adequate product clarity are obtainable by reducing the pH of surfactant compositions comprising the staged core-shell polymers of the invention and a food grade preservative without neutralizing the polymer with an additional alkaline pH adjusting agent. The surfactant composition is formulated from the components listed in Table 21.

TABLE 21

(Thickened Acidified Surfactant Composition)

| | Component | Amount (wt. %) | Function |
|---|---|---|---|
| 1 | D.I. Water | q.s. to 100 | Diluent |
| 2 | Polymer No. 3(33.7% active polymer solids) | 7.42 | Rheology Modifier |
| 3 | Sulfochem ™ ES-2 CWK Surfactant (28% active) | 40.00 | Detersive Surfactant |
| 4 | Chembetaine ™ CAD Surfactant (35% active) | 6.70 | Amphoteric Surfactant |
| 5 | Sodium Benzoate | 0.25 | Preservative |
| 6 | Citric Acid (50% aqueous wt./wt.) | q.s. to pH | pH Adjusting Agent |

Components 1 through 5 are added to a vessel in the order listed in the table and mixed under slow agitation until a uniform master batch formulation is obtained. The initial pH of the formulation is measured and recorded. The pH of the formulation is sequentially reduced to approximately 5.0 and 4.5 with citric acid (component 6). At each pH value, 100 g and 20 g aliquots of the master batch formulation is transferred into 4 oz. jars and 6 dram vials, respectively, and centrifuged to remove any entrained air bubbles. The sample jars and vials containing the centrifuged formulations are capped and held for 24 hrs. after which rheology and clarity property measurements are made. Viscosity and yield value measurements are carried out on the 100 g samples and turbidity measurements are completed on the 20 g samples. The data is presented in Table 22.

TABLE 22

| | pH (Initial) | pH (5.0) | pH (4.5) |
|---|---|---|---|
| pH Value | 5.54 | 4.96 | 4.57 |
| Viscosity (mPa · s) | 3,340 | 3,810 | 3,930 |
| Yield Value (dyn/cm$^2$) | 132 | 142 | 146 |
| Turbidity (NTU) | 16.4 | 28.7 | 43 |

Example 34

This example illustrates the use of a staged core-shell polymer as a thickener in a textile print paste (Ex. 34A) and in a textile coating formulation (Ex. 34B), at the active polymer weight % indicated in Table 23.

TABLE 23

(Textile Treatment Compositions)

| | Component | Example 34A | Example 34B |
|---|---|---|---|
| 1 | D.I. Water | q.s. to 100% | q.s. to 100% |
| 2 | Polymer No. 2 | 1.5 (wt. % active solids) | 0.76 (wt. % active solids) |
| 3 | Ammonium hydroxide (28% active) to pH | pH 9.7 | pH 8.5 |
| 4 | Printrite ® 595 Binder | 5.0 | — |
| 5 | Hycar ® 2671 Binder | — | 41.86 |
| 6 | Pigment | 5.0 | — |
| 7 | Foamaster ® DF-160L Defoamer | — | 0.25 |
| 8 | Ammonium Nitrate (25% aqueous wt./wt.) | — | 0.45 |

What is claimed is:

1. An acrylic based staged core-shell polymer composition comprising from about 5% to about 60% by weight of an acrylic based linear core polymer and from about 95% to about 40% by weight of an acrylic based crosslinked shell polymer, wherein I) said linear core polymer is polymerized from a monomer selected from:

a) from about 10% to about 80% by weight of at least one carboxylic acid monomer comprising acrylic acid, methacrylic acid, itaconic acid, fumaric acid, crotonic acid, aconitic acid, or maleic acid, or combinations thereof;

b) from about 90% to about 20% by weight of at least one $C_1$ to $C_5$ alkyl ester and/or at least one $C_1$ to $C_5$ hydroxyalkyl ester of acrylic acid or methacrylic acid; and optionally c) from about 1% to about 35% by weight of at least one α,β-ethylenically unsaturated monomer selected from a monomer represented by the formulas:

$CH_2{=}C(R)C(O)OR^1$, i)

wherein R is selected from hydrogen or methyl; and $R^1$ is selected from $C_6$-$C_{10}$ alkyl, $C_6$ to $C_{10}$ hydroxyalkyl, $—(CH_2)_2OCH_2CH_3$, and $—(CH_2)_2C(O)OH$ $CH_2{=}C(R)X$, ii)

wherein R is hydrogen or methyl; and X is selected from $—C_6H_5$, —CN, $—C(O)NH_2$, $—NC_4H_6O$, —C(O)NHC $(CH_3)_3$, —$C(O)N(CH_3)_2$, —$C(O)NHC(CH_3)_2(CH_2)_4CH_3$, and —$C(O)NHC(CH_3)_2CH_2S(O)(O)OH$;

$CH_2$═$CHOC(O)R^1$, iii)

wherein $R^1$ is linear or branched $C_1$-$C_{18}$ alkyl; and $CH_2$═$C(R)C(O)OAOR^2$, iv)

wherein A is a divalent radical selected from —$CH_2CH(OH)CH_2$— and —$CH_2CH(CH_2OH)$—, R is selected from hydrogen or methyl, and $R^2$ is an acyl residue of a linear or branched, saturated or unsaturated $C_{10}$ to $C_{22}$ fatty acid; and wherein II) said crosslinked shell polymer is polymerized from a monomer selected from;

a1) from about 10% to about 80% by weight of at least one carboxylic acid monomer comprising acrylic acid, methacrylic acid, itaconic acid, fumaric acid, crotonic acid, aconitic acid, or maleic acid, or combinations thereof;

b1) from about 90% to about 15% by weight of at least one $C_1$ to $C_5$ alkyl ester and/or at least one $C_1$ to $C_5$ hydroxyalkyl ester of acrylic acid or methacrylic acid;

c1) from about 0.01% to about 5% by weight of at least one crosslinking monomer; and optionally d1) from about 1% to about 35% by weight of at least one α,β-ethylenically unsaturated monomer selected from formulas i) to iv) above.

2. A composition of claim 1 further comprising:

A) at least one surfactant selected from anionic, zwitterionic or amphoteric, cationic, or nonionic surfactant, and combinations thereof; and B) water.

3. A composition of claim 2 wherein the pH of said composition ranges from about 0.5 to about 14.

4. A composition of claim 2 wherein the pH of said composition ranges from about 2 to about 7.

5. A composition of claim 2 wherein the pH of said composition ranges from about 3 to about 6.

6. A composition of claim 1 further comprising:

A) at least one surfactant selected from anionic and a zwitterionic or amphoteric, surfactant, and combinations thereof;

B) at least one acid base preservative; and

C) water.

7. A composition of claim 6 further comprising a pH adjusting agent selected from at least one alkalinity adjusting agent, at least one acidity adjusting agent, and combinations thereof.

8. A composition of claim 7, wherein the pH of said composition ranges from about 0.5 to about 6.

9. A composition of claim 7 wherein the pH of said composition ranges from about 2 to about 5.5.

10. A composition of claim 7 wherein the pH of said composition ranges from about 3 to about 5.

11. A composition of claim 1 further comprising:

A) at least one component selected from surfactants, hair and skin conditioning agents, emollients, emulsifiers, auxiliary rheology modifiers, thickening agents, vitamins, hair growth promoters, self-tanning agents, sunscreens, skin lighteners, anti-aging compounds, anti-wrinkle compounds, anti-cellulite compounds, anti-acne compounds, anti-dandruff agents, anti-inflammatory compounds, analgesics, antiperspirant agents, deodorant agents, hair fixatives, particulates, abrasives, moisturizers, antioxidants, keratolytic agents, anti-static agents, foam boosters, hydrotropes, solublizing agents, chelating agents, antimicrobial agents, antifungal agents, pH adjusting agents, chelating agents, buffering agents, botanicals, hair colorants, oxidizing agents, reducing agents, propellants, insoluble components, thermochromic dyes, hair and skin bleaching agents, pigments, anticaries, anti-tartar agents, antiplaque agents, solvents, preservatives; and combinations thereof; and B) water.

12. An acrylic based staged core-shell polymer comprising from about 5% to about 60% by weight of an acrylic based linear first stage polymer and from about 95% to about 40% by weight of at least one acrylic based outer stage polymer, wherein at least one of said at least one acrylic based outer stage polymers must be crosslinked; said linear core polymer is polymerized in a first stage polymerization reaction from a monomer composition comprising:

a) from about 10% to about 80% by weight of at least one carboxylic acid monomer comprising acrylic acid, methacrylic acid, itaconic acid, fumaric acid, crotonic acid, aconitic acid, maleic acid, and salts thereof, and combinations thereof;

b) from about 90% to about 20% by weight of at least one $C_1$ to $C_5$ alkyl ester and/or at least one $C_1$ to $C_5$ hydroxyalkyl ester of acrylic acid or methacrylic acid; and optionally c) from about 1% to about 35% by weight of at least one α,β-ethylenically unsaturated monomer selected from a monomer represented by the formulas:

$CH_2$═$C(R)C(O)OR^1$, i)

wherein R is selected from hydrogen or methyl; and $R^1$ is selected from $C_6$-$C_{10}$ alkyl, $C_6$ to $C_{10}$ hydroxyalkyl, —$(CH_2)_2OCH_2CH_3$, and —$(CH_2)_2C(O)OH$ and salts thereof;

$CH_2$═$C(R)X$, ii)

wherein R is hydrogen or methyl; and X is selected from —$C_6H_5$, —CN, —$C(O)NH_2$, —$NC_4H_6O$, —$C(O)NHC(CH_3)_3$, —$C(O)N(CH_3)_2$, —$C(O)NHC(CH_3)_2(CH_2)_4CH_3$, and —$C(O)NHC(CH_3)_2CH_2S(O)(O)OH$ and salts thereof;

$CH_2$═$CHOC(O)R^1$, iii)

wherein $R^1$ is linear or branched $C_1$-$C_{18}$ alkyl; and $CH_2$═$C(R)C(O)OAOR^2$, iv)

wherein A is a divalent radical selected from —$CH_2CH(OH)CH_2$— and —$CH_2CH(CH_2OH)$—, R is selected from hydrogen or methyl, and $R^2$ is an acyl residue of a linear or branched, saturated or unsaturated $C_{10}$ to $C_{22}$ fatty acid; wherein said first stage monomer composition is free of any crosslinking monomers; and wherein at least one of said at least one outer stage polymers is polymerized from a monomer composition comprising:

a1) from about 10% to about 80% by weight of at least one carboxylic acid monomer comprising acrylic acid, methacrylic acid, itaconic acid, fumaric acid, crotonic acid, aconitic acid maleic acid, and salts thereof, and combinations thereof;

b1) from about 90% to about 15% by weight of at least one $C_1$ to $C_5$ alkyl ester and/or at least one $C_1$ to $C_5$ hydroxyalkyl ester of acrylic acid or methacrylic acid;

c1) from about 0.01% to about 5% by weight of at least one crosslinking monomer; and optionally d1) from about 1% to about 35% by weight of at least one α,β-ethylenically unsaturated monomer selected from formulas i) to iv) above.

13. The polymer of claim 12, wherein said monomer composition in said first stage polymerization reaction comprises an auxiliary emulsifier selected from an ethoxylated $C_{10}$ to $C_{22}$ fatty alcohol.

14. The polymer of claim 13, wherein said monomer composition in said at least one of said at least one outer stage polymerization reaction(s) comprises an auxiliary emulsifier selected from an ethoxylated $C_{10}$ to $C_{22}$ fatty alcohol.

15. A method for making an acrylic based staged core-shell polymer, said method comprising:

I) polymerizing a first stage monomer composition in the absence of a crosslinking monomer to obtain a first stage linear polymer, said first stage monomer composition comprising:

a) from about 10% to about 80% by weight of at least one carboxylic acid monomer comprising acrylic acid, methacrylic acid, itaconic acid, fumaric acid, crotonic acid, aconitic acid, maleic acid, and salts thereof, and combinations thereof;

b) from about 90% to about 20% by weight of at least one $C_1$ to $C_5$ alkyl ester and/or at least one $C_1$ to $C_5$ hydroxyalkyl ester of acrylic acid or methacrylic acid; and optionally c) from about 1% to about 35% by weight of at least one α,β-ethylenically unsaturated monomer selected from a monomer represented by the formulas:

$CH_2{=}C(R)C(O)OR^1$, i)

wherein R is selected from hydrogen or methyl; and $R^1$ is selected from $C_6$-$C_{10}$ alkyl, $C_6$ to $C_{10}$ hydroxyalkyl, $-(CH_2)_2OCH_2CH_3$, and $-(CH_2)_2C(O)OH$ and salts thereof;

$CH_2{=}C(R)X$, ii)

wherein R is hydrogen or methyl; and X is selected from $-C_6H_5$, $-CN$, $-C(O)NH_2$, $-NC_4H_6O$, $-C(O)NHC(CH_3)_3$, $-C(O)N(CH_3)_2$, $-C(O)NHC(CH_3)_2(CH_2)_4CH_3$, and $-C(O)NHC(CH_3)_2CH_2S(O)(O)OH$ and salts thereof;

$CH_2{=}CHOC(O)R^1$, iii)

wherein $R^1$ is linear or branched $C_1$-$C_{18}$ alkyl; and $CH_2{=}C(R)C(O)OAOR^2$, iv)

wherein A is a divalent radical selected from $-CH_2CH(OH)CH_2-$ and $-CH_2CH(CH_2OH)-$, R is selected from hydrogen or methyl, and $R^2$ is an acyl residue of a linear or branched, saturated or unsaturated $C_{10}$ to $C_{22}$ fatty acid; followed by II) polymerizing at least one second stage monomer composition in the presence of said first stage polymer particle to obtain a crosslinked second stage polymer, said second stage monomer composition comprising:

a1) from about 10% to about 80% by weight of at least one carboxylic acid monomer comprising acrylic acid, methacrylic acid, itaconic acid, fumaric acid, crotonic acid, aconitic acid, maleic acid, and salts thereof, and combinations thereof;

b1) from about 90% to about 15% by weight of at least one $C_1$ to $C_5$ alkyl ester and/or at least one $C_1$ to $C_5$ hydroxyalkyl ester of acrylic acid or methacrylic acid;

c1) from about 0.01% to about 5% by weight of at least one crosslinking monomer; and optionally d1) from about 1% to about 35% by weight of at least one α,β-ethylenically unsaturated monomer selected from formulas i) to iv) above.

16. The method of claim 15, wherein said monomer composition in said first stage monomer composition comprises an auxiliary emulsifier selected from an ethoxylated $C_{10}$ to $C_{22}$ fatty alcohol.

17. The method of claim 16, wherein said second stage monomer composition comprises an auxiliary emulsifier selected from an ethoxylated $C_{10}$ to $C_{22}$ fatty alcohol.

18. A method for thickening an aqueous composition comprising a staged core-shell acrylic polymer comprising: adding to said aqueous composition a pH adjusting agent selected from an acidic material, an alkaline material, and mixtures thereof, wherein said core-shell polymer comprises: from about 5% to about 60% by weight of an acrylic based linear core polymer and from about 95% to about 40% by weight of an acrylic based crosslinked shell polymer, wherein I) said linear core polymer is polymerized from a monomer selected from:

a) from about 10% to about 80% by weight of at least one carboxylic acid monomer comprising acrylic acid, methacrylic acid, itaconic acid, fumaric acid, crotonic acid, aconitic acid, maleic acid, and salts thereof, and combinations thereof;

b) from about 90% to about 20% by weight of at least one $C_1$ to $C_5$ alkyl ester and/or at least one $C_1$ to $C_5$ hydroxyalkyl ester of acrylic acid or methacrylic acid; and optionally c) from about 1% to about 35% by weight of at least one α,β-ethylenically unsaturated monomer selected from a monomer represented by the formulas:

$CH_2{=}C(R)C(O)OR^1$, i)

wherein R is selected from hydrogen or methyl; and $R^1$ is selected from $C_6$-$C_{10}$ alkyl, $C_6$ to $C_{10}$ hydroxyalkyl, $-(CH_2)_2OCH_2CH_3$, and $-(CH_2)_2C(O)OH$ and salts thereof;

$CH_2{=}C(R)X$, ii)

wherein R is hydrogen or methyl; and X is selected from $-C_6H_5$, $-CN$, $-C(O)NH_2$, $-NC_4H_6O$, $-C(O)NHC(CH_3)_3$, $-C(O)N(CH_3)_2$, $-C(O)NHC(CH_3)_2(CH_2)_4CH_3$, and $-C(O)NHC(CH_3)_2CH_2S(O)(O)OH$ and salts thereof;

$CH_2{=}CHOC(O)R^1$, iii)

wherein $R^1$ is linear or branched $C_1$-$C_{18}$ alkyl; and $CH_2{=}C(R)C(O)OAOR^2$, iv)

wherein A is a divalent radical selected from $-CH_2CH(OH)CH_2-$ and $-CH_2CH(CH_2OH)-$, R is selected from hydrogen or methyl, and $R^2$ is an acyl residue of a linear or branched, saturated or unsaturated $C_{10}$ to $C_{22}$ fatty acid; and wherein II) said crosslinked shell polymer is polymerized from a monomer selected from;

a1) from about 10% to about 80% by weight of at least one carboxylic acid monomer comprising acrylic acid, methacrylic acid, itaconic acid, fumaric acid, crotonic acid, aconitic acid, maleic acid, and salts thereof, and combinations thereof;

b1) from about 90% to about 15% by weight of at least one $C_1$ to $C_5$ alkyl ester and/or at least one $C_1$ to $C_5$ hydroxyalkyl ester of acrylic acid or methacrylic acid;

c1) from about 0.01% to about 5% by weight of at least one crosslinking monomer; and optionally d1) from about 1% to about 35% by weight of at least one α,β-ethylenically unsaturated monomer selected from formulas i) to iv) above.

19. A method of claim 18, wherein said aqueous composition includes a surfactant.

20. A method of claim 19, wherein said surfactant is selected from an anionic surfactant, an amphoteric surfactant, a nonionic, a cationic, and mixtures thereof.

21. A method of claim 19, wherein said surfactant is selected from at least one anionic surfactant, at least one amphoteric surfactant, and mixtures thereof.

22. A method of claim 19, wherein an alkaline pH adjusting agent is added to said composition.

23. A method of claim 19, wherein an acidic pH adjusting agent is added to said composition.

24. A method of claim 19, wherein an alkaline and an acidic pH adjusting agent is added to said composition.

25. A method of claim 24, wherein said alkaline pH adjusting agent is added to said composition before said acidic pH adjusting agent is added.

26. A method of claim 25 wherein, the pH of said composition is adjusted with said alkaline pH adjusting agent to about 0.5 to about 2 pH units above the initial pH of the composition and subsequently reducing the alkaline adjusted pH of the composition by adding said acidic pH adjusting agent in a sufficient amount to obtain a final pH value ranging from about 3.5 to about 5.5.

27. A method of claim 26 wherein the initial pH of said composition is at least about 5.0.

28. An composition of claim 1, wherein said monomers a) and a1) are selected from acrylic acid, methacrylic acid, or combinations thereof, and said monomers b) and b1) are selected from ethyl acrylate.

29. A composition of claim 2, wherein said monomers a) and a1) are selected from acrylic acid, methacrylic acid, or combinations thereof, and said monomers b) and b1) are selected from ethyl acrylate.

30. A composition of claim 6, wherein said monomers a) and a1) are selected from acrylic acid, methacrylic acid, or combinations thereof, and said monomers b) and b1) are selected from ethyl acrylate.

31. A composition of claim 11, wherein said monomers a) and a1) are selected from acrylic acid, methacrylic acid, or combinations thereof, and said monomers b) and b1) are selected from ethyl acrylate.

32. A composition of claim 12, wherein said monomers a) and a1) are selected from acrylic acid, methacrylic acid, or combinations thereof, and said monomers b) and b1) are selected from ethyl acrylate.

33. A method of claim 15, wherein said monomers a) and a1) are selected from acrylic acid, methacrylic acid, or combinations thereof, and said monomers b) and b1) are selected from ethyl acrylate.

34. A method of claim 18, wherein said monomers a) and a1) are selected from acrylic acid, methacrylic acid, or combinations thereof, and said monomers b) and b1) are selected from ethyl acrylate.

35. A composition of claim 2, wherein said at least one surfactant is selected from alkyl sulfates, alkyl ether sulfates, alkyl sulphonates, alkaryl sulfonates, a-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof, betaines, sultaines, and alkyl amphocarboxylates.

36. A composition of claim 35, wherein said at least one surfactant is selected from sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, fatty acid soaps, lauryl betaine, coco betaine, cocohexadecyl dimethylbetaine, cocoamidopropyl betaine, cocoamidopropylhyrdoxy sultaine, or mixtures thereof.

37. A composition of claim 6, wherein said at least one surfactant is selected from alkyl sulfates, alkyl ether sulfates, alkyl sulphonates, alkaryl sulfonates, a-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof, betaines, sultaines, and alkyl amphocarboxylates.

38. A composition of claim 37, wherein said at least one surfactant is selected from sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, fatty acid soaps, lauryl betaine, coco betaine, cocohexadecyl dimethylbetaine, cocoamidopropyl betaine, cocoamidopropylhyrdoxy sultaine, or mixtures thereof.

39. A composition of claim 11, wherein said surfactant is selected from alkyl sulfates, alkyl ether sulfates, alkyl sulphonates, alkaryl sulfonates, a-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof, betaines, sultaines, and alkyl amphocarboxylates.

40. A composition of claim 39, wherein said surfactant is selected from sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, fatty acid soaps, lauryl betaine, coco betaine, cocohexadecyl dimethylbetaine, cocoamidopropyl betaine, cocoamidopropylhyrdoxy sultaine, or mixtures thereof.

41. A method of claim 20, wherein said surfactant is selected from alkyl sulfates, alkyl ether sulfates, alkyl sulphonates, alkaryl sulfonates, a-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof, betaines, sultaines, and alkyl amphocarboxylates.

42. A method of claim 41, wherein said surfactant is selected from sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, fatty acid soaps, lauryl betaine, coco betaine, cocohexadecyl dimethylbetaine, cocoamidopropyl betaine, cocoamidopropylhyrdoxy sultaine, or mixtures thereof.

* * * * *